United States Patent [19]
Paoletti et al.

[11] Patent Number: 5,744,141
[45] Date of Patent: Apr. 28, 1998

[54] FLAVIVIRUS RECOMBINANT POXVIRUS IMMUNOLOGICAL COMPOSITION

[75] Inventors: Enzo Paoletti, Delmar; Steven Elliot Pincus, East Greenbush, both of N.Y.

[73] Assignee: Virogenetics Corporation, Troy, N.Y.

[21] Appl. No.: 484,304

[22] Filed: Jun. 7, 1995

Related U.S. Application Data

[60] Division of Ser. No. 224,391, Apr. 7, 1994, Pat. No. 5,744,140, and a continuation-in-part of Ser. No. 105,483, Aug. 12, 1993, Pat. No. 5,494,807, which is a continuation of Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, abandoned, said Ser. No. 224,391, is a continuation of Ser. No. 729,800, Jul. 17, 1991, abandoned, which is a continuation-in-part of Ser. No. 714,687, Jun. 13, 1991, Pat. No. 5,514,375, which is a continuation-in-part of Ser. No. 711,429, Jun. 6, 1991, abandoned, which is a continuation-in-part of Ser. No. 567,960, Aug. 15, 1990, abandoned, said Ser. No. 714,687, is a continuation-in-part of Ser. No. 713,967, Jun. 11, 1991, abandoned, which is a continuation-in-part of Ser. No. 666,056, Mar. 7, 1991, abandoned.

[51] Int. Cl.$^6$ .............. A61K 39/285; A61K 39/295; C07K 14/18; C12N 7/01

[52] U.S. Cl. .............. 424/199.1; 424/184.1; 424/186.1; 424/204.1; 424/210.1; 424/212.1; 424/232.1; 435/235.1; 435/89; 435/70.1; 435/320.1

[58] Field of Search .............. 435/235.1, 89, 435/70.1, 320.1; 424/184.1, 186.1, 204.1, 199.1, 210.1, 218.1, 232.1

[56] References Cited

U.S. PATENT DOCUMENTS

| | | | |
|---|---|---|---|
| 5,021,347 | 6/1991 | Yasui et al. | 435/235.1 |
| 5,174,993 | 12/1992 | Paoletti | 424/89 |
| 5,494,807 | 2/1996 | Paoletti et al. | 435/69.3 |
| 5,514,375 | 5/1996 | Paoletti et al. | 424/199.1 |

OTHER PUBLICATIONS

Putnak et al., 1990, J. of Gen. Virol., vol. 71, pp. 1697-1702.
McCown et al., 1990, Am. J. Trop. Med. Hyg., vol. 42(5), pp. 491-499.
Alkhatib, G., and Briedis, D., Virol. 150, 479-490 (1986).
Bertholet, C., Drillien, R., and Wittek, R., Proc. Natl. Acad. Sci. 82, 2096-2100 (1985).
Brandt, W. E., J. Infect. Dis. 157, 1105-1111 (1988).
Bray, M., Zhao, B., Markoff, L., Eckels, K. H., Chanock, R. M., and Lai, C.-J., J. Virol. 63, 2853-2856 (1989).
Cane, P.A., and Gould, E.A., J. Gen. Virol. 70, 557-564 (1989).
Clarke, D. H., and Casals, J., Am. J. Trop., Med. Hyg. 7, 561-573 (1958).
Clewell, D.B., J. Bacteriol 110, 667-676 (1972).
Clewell, D.B. and Helinski, D.R., Proc. Natl. Acad. Sci. USA 62, 1159-1166 (1969).
Colinas, R. J., Condit, R. C., and Paoletti, E., Virus Research 18, 49-70 (1990).
D'Alessio, J.M., and Gerrard, G.F., Nucleic Acids Res. 16, 1999-2014 (1988).
Deubel, V., Kinney, R. M., Esposito, J. J., Cropp, C. B., Vorndam, A. V., Monath, T. P., and Trent, D., J. Gen. Virol. 69, 1921-1929 (1988).
Dubois, M.-F., Pourcel, C., Rousset, S., Chany, C., and Tiollais, P., Proc. Natl. Acad. Sci. USA 77, 4549-4553 (1980).
Eckels, K. H., Hetrick, F. M., and Russell, P. K. Infect. Immun. 11, 1053-1060 (1975).
Engelke, D. R., Hoener, P. A., and Collins, F. S., Proc. Natl. Acad. Sci. USA 85, 544-548 (1988).
Falgout, B., Chanock, R., and Lai, C.-J., J. Virol. 63, 1852-1860 (1989).
Fan, W., and Mason, P. W., Virol. 177, 470-476 (1990).
Gibson, C. A., Schlesinger, J. J., and Barrett, A. D. T. Vaccine 6, 7-9 (1988).
Goebel, S. J., Johnson, G. P., Perkus, M. E., Davis, S. W., Winslow, J. P., and Paoletti, E., Virology 179, 247-266 (1990a).
Goebel, S. J., Johnson, G. P., Perkus, M. E., Davis, S. W., Winslow, J. P., and Paoletti, E., Virology 179, 517-563 (1990b).
Gould, E. A., Buckley, A., Barrett, A. D. T., and Cammack, N., J. Gen. Virol. 67, 591-595 (1986).
Guo, P., Goebel, S., Davis, S., Perkus, M. E., Taylor, J., Norton, E., Allen, G., Lanquet, B., Desmettre, P., and Paoletti, E., J. Virol. 64, 2399-2406 (1990).
Guo, P., Goebel, S., Davis, S., Perkus, M. E., Languet, B., Desmettre, P., Allen, G., and Paoletti, E., J. Virol. 63, 4189-4198 (1989).
Haishi, S., Imai, H., Hirai, K., Igarashi, A., and Kato, S., Acta Virol. 33, 497-503 (1989).
Henchal, E. A., Henchal, L. S., and Schlesinger J. J., J. Gen. Virol. 69, 2101-2107 (1988).
Huang, C. H., Advances in Virus Research 27, 71-101 (1982).
Kaufman, B. M., Summers, P. L., Dubois, D. R., Cohen, W. H., Gentry, M. K., Timchak, R. L., Burke, D. S., and Eckels, K. H., Am. J. Trop. Med. Hyg. 41, 576-580 (1989).
Kaufman, B. M., Summers, P. L., Dubois, D. R., and Eckels, K. H., Am. J. Trop. Med. Hyg. 36, 427-434 (1987).

(List continued on next page.)

*Primary Examiner*—Marian C. Knode
*Assistant Examiner*—Ali Salimi
*Attorney, Agent, or Firm*—Frommer Lawrence & Haug LLP; William S. Frommer; Thomas J. Kowalski

[57] ABSTRACT

What is described is a recombinant poxvirus, such as vaccinia virus, fowlpox virus and canarypox virus, containing foreign DNA from flavivirus, such as Japanese encephalitis virus, yellow fever virus and Dengue virus. In a preferred embodiment, the recombinant poxvirus generates an extracellular particle containing flavivirus E and M proteins capable of inducing neutralizing antibodies, hemagglutination-inhibiting antibodies and protective immunity against flavivirus infection. What is also described is a vaccine containing the recombinant poxvirus for inducing an immunological response in a host animal inoculated with the vaccine.

17 Claims, 24 Drawing Sheets

OTHER PUBLICATIONS

Kieny, M.P., Lathe, R., Drillien, R., Spehner, D., Skory, S., Schmitt, P., Wiktor, T., Koprowski, H., and Lecocq, J.P., Nature (London) 312, 163–166 (1984).

Kimura–Kuroda, J., and Yasui, K., J. Immunol. 141, 3606–3610 (1988).

Knauf, V.C., and Nester, E.W., Plasmid 8, 45–54 (1982).

Kunkel, T. A., Proc. Natl. Acad. Sci. USA 82, 488–492 (1985).

Mandecki, W., Proc. Natl. Acad. Sci. USA 83, 7177–7181 (1986).

Maniatis, T., Fritsch, E. F., and Sambrook, J., Molecular Cloning, Cold Spring Harbor Laboratory, NY 545 pages (1986).

Mason, P. W., McAda, P. C., Dalrymple, J. M., Fournier, M. J., and Mason, T. L., Virol. 158, 361–372 (1987a).

Mason, P. W., McAda, P.C., Mason, T.L., and Fournier, M.J., Virol. 161, 262–267 (1987B).

Mason, P. W., Dalrymple, J. M., Gentry, M. K., McCown, J. M., Hoke, C. H., Burke, D. S., Fournier, M. J., and Mason, T. L., J. Gen. Virol. 70, 2037–2049 (1989).

Mason, P. W., Virol. 169, 354–364 (1989).

Mason, P. W., Pincus, S., Fournier, M. J., Mason, T. L., Shope, R. E., and Paoletti, E., Virol. 180, 294–305 (1991).

Matsuura, Y., Miyamoto, M., Sato, T., Morita, C., and Yasui, K., Virol. 173, 674–682 (1989).

McAda, P. C., Mason, P. W., Schmaljohn, C. S., Dalrymple, J. M., Mason, T. L., and Fournier, M. J., Virol. 158, 348–360 (1987).

Men, R., Bray, M., and Lai, C.J., J. Virol. 65, 1400–1407 (1991).

Monath, T. P., In "The Togaviridae and Flaviviridae", S. Schlesinger and M. J. Schlesinger, Eds., Plenum Press, New York/London, pp. 375–440 (1986).

Moriarty, A. M., Hoyer, B. H., Shih, J. W.–K., Gerin, J. L., and Hamer, D.H., Proc. Natl. Acad. Sci. USA 78, 2606–2610 (1981).

Nowak, T., Färber, P. M., Wengler, G. and Wengler, G., Virol. 169, 365–376 (1989).

Okayama, H., and Berg, P., Mol. Cell. Biol. 2, 161–170 (1982).

Panicali, D., and Paoletti, E., Proc. Natl. Acad. Sci. USA 79, 4927–4931 (1982).

Perkus, M. E., Goebel, S. J., Davis, S. W., Johnson, G. P., Limbach, K., Norton, E. K., and Paoletti, E., Virology 179, 276–286 (1990).

Perkus, M. E., Piccini, A., Lipinskas, B. R., and Paoletti, E., Science 229, 981–984 (1985).

Perkus, M. E., Limbach, K., and Paoletti, E., J. Virol. 63, 3829–3836 (1989).

Piccini, A., Perkus, M.E. and Paoletti, E., In Methods in Enzymology, vol. 153, eds. Wu, R., and Grossman, L., (Academic Press) pp. 545–563 (1987).

Repik, P.M., Dalrymple, J.M., Brandt, W.E., McCown, J.M., and Russell, P.K., Am. J. Trop. Med. Hyg. 32, 577–589 (1983).

Rice, C. M., Lenches, E.M., Eddy, S.R., Shin, S.J., Sheets, R.L., and Strauss, J.H., Science 229, 726–733 (1985).

Ruiz–Linares, A., Cahour, A., Despres, P., Girard, M., and Bouloy, M., J. Virol. 63, 4199–4209 (1989).

Russell, P. K., Brandt, W. E., and Dalrymple, J. M. In "The Togaviruses", R. W. Schlesinger, Ed., Academic Press, New York/London 18, 503–529 (1980).

Sanger, F., Nicklen, S., and Coulson, A. R., Proc. Natl. Acad. Sci. USA 74, 5463–5467 (1977).

Schlesinger, J. J., Brandriss, M. W., Cropp, C. B., and Monath, T. P., J. Virol. 60, 1153–1155 (1986).

Schlesinger, J. J., Brandriss, M. W., and Walsh, E. E., J. Immunol. 135, 2805–2809 (1985).

Schlesinger, J. J., Brandriss, M. W., and Walsh, E. E., J. Gen. Virol. 68, 853–857 (1987).

Shapira, S. K., Chou, J., Richaud, F. V. and Casadaban, M. J., Gene 25, 71–82 (1983).

Shapiro, D., Brandt, W. E., and Russell, P. K., Virol. 50, 906–911 (1972).

Shope, R. E., In "The Togaviruses", R. W. Schlesinger, ed., Academic Press, N.Y. pp. 47–82 (1980).

Tabor, S., and Richardson, C. C., Proc. Natl. Acad. Sci. USA 84, 4767–4771 (1987).

Tartaglia et l. Critical Reviews in Immunology. 10, 13–30 (1990).

Taylor, J., Weinberg, R., Kawaoka, Y., Webster, R.G., and Paoletti, E., Vaccine 6, 504–508 (1988a).

Taylor, J., Weinberg, R., Languet, B., Desmettre, P., and Paoletti, E., Vaccine 6, 497–503 (1988b).

Taylor, J., Pincus, S., Tartaglia, J., Richardson, C., Alkhatib, G., Briedis, D., Appel, M., Norton, E., and Paoletti, E., J. Virol. 65, in press (1991).

Tesh, R. B., and Duboise, S. M., Am. J. Trop. Med. Hyg. 36, 662–668 (1987).

Tiollais, P., Pourcel, C., and Dejean, A., Nature 317, 489–495 (1985).

Wengler, G., and Wengler, G., J. Virol. 63, 2521–2526 (1989a).

Wengler, G., and Wengler, G., J. Gen. Virol. 70, 987–992 (1989b).

Winkler, G., Randolph, V. B., Cleaves, G. R., Ryan, T. E., and Stollar, V., Virol. 162, 187–196 (1988).

Yasuda, A., Kimura–Kuroda, J., Ogimoto, M., Miyamoto, M., Sata, T., Sato, T., Takamura, C., Kurata, T., Kojima, A., and Yasui, K., J. Virol. 64, 2788–2795 (1990).

Yuen, L., and Moss, B., Proc. Natl. Acad. Sci. USA 84, 6417–6421 (1987).

Zhang, Y.–M., Hayes, E. P., McCarthy, T. C., Dubois, D. R., Summers, P. L., Eckels, K. H., Chanock, R. M., and Lai, C.–J., J. Virol. 62, 3027–3031 (1988).

Zhao, B., Prince, G., Horswood, R., Eckels, K., Summers, P., Chanock, R., and Lai, C.–J., J. Virol. 61, 4019–4022 (1987).

FIG. 2

```
         stop terminator
J3   5'-tga ttttat CGGCCG A    -3'
J4   3'-ACT AAAAATA GCCGGC TTCGA-5'
              Eag I  Hin dIII start
J1B  5'-TCGAG CCCGGG atg TGGCTCGCGGAGCTTGCCAGTTGTCATAGCCTGCGGCAGGAGCCATGAAGTTGTCAAATTTCCAGGGG A    -3'
J2B  3'-    C GGGCCC TAC ACCGAGCGCCTCGAACGGTCAACAGTATCGGACGCCTCCTGGTACTTCAACAGTTTAAAGGTCCCC TTCGA-5'
        Xho I  Sma I                                                                        Hin dIII start
J7   5'-GATCC ATGCATTCTAGA C    -3'
J8   3'-    G TACGTAAGATCT GGTAC-5'
        Bam HI              Nco I start
J9   5'-AGCTT CCCGGG atg CTTGGCAGTAACAACGGTC-3'
J10  3'-    A GGGCCC TAC GAACCGTCATTGTTGCCAG-5'
        Hin dIII Sam I stop terminator
J37  5'-AAAAACAACAAAAAGA tga ttttat CGGCCG A    -3'
J38  3'-TTTTTGTTGTTTTTCT ACT AAAAATA GCCGGC TTCGA-5'
                                    Eag I  Hin dIII
```

FIG. 3

CELL-ASSOCIATED NS1

| VIRUS: | JEV | | | vP650 | | | vP555 | | | vP658 | | | vP583 | | |
|---|---|---|---|---|---|---|---|---|---|---|---|---|---|---|---|
| GLYCOSIDASE: | M | H | F | M | H | F | M | H | F | M | H | F | M | H | F |

NS1'
NS1
dye

FIG. 5

EXTRACELLULAR NS1

| VIRUS: | JEV | | | vP650 | | | vP555 | | | vP658 | | | vP583 | | |
|---|---|---|---|---|---|---|---|---|---|---|---|---|---|---|---|
| GLYCOSIDASE: | M | H | F | M | H | F | M | H | F | M | H | F | M | H | F |

NS1'
NS1
dye

FIG. 6

CELL-ASSOCIATED E

| VIRUS: | JEV | | | vP650 | | | vP555 | | | vP658 | | | vP583 | | |
|---|---|---|---|---|---|---|---|---|---|---|---|---|---|---|---|
| GLYCOSIDASE: | M | H | F | M | H | F | M | H | F | M | H | F | M | H | F |

E dye

FIG. 7

EXTRACELLULAR E

| VIRUS: | JEV | | | vP650 | | | vP555 | | |
|---|---|---|---|---|---|---|---|---|---|
| GLYCOSIDASE: | M | H | F | M | H | F | M | H | F |

E dye

FIG. 8

FIG. 9 virion          SHA

IMMUNE RESPONSE

FIG. 10

```
   1 ATGACTAAAA AACCAGGAGG GCCCGGTAAA AACCGGGCTA TCAATATGCT GAAACGCGGC
  61 TTACCCCGCG TATTCCCACT AGTGGGAGTG AAGAGGGTAG TGATGAGCTT GTTGGACGGC
 121 AGAGGGCCAG TACGTTTCGT GCTGGCTCTT ATCACGTTCT TCAAGTTTAC AGCATTAGCC
 181 CCGACCAAGG CGCTTTTAGG CCGATGGAAA GCAGTGGAAA AGAGTGTGGC AATGAAACAT
 241 CTTACTAGTT TCAAACGAGA ACTCGGAACA CTCATTGACG CCGTGAACAA GCGGGGCAGA
 301 AAGCAAAACA AAAGAGGAGG AAATGAAGGC TCAATCATGT GGCTCGCGAG CTTGGCAGTT
 361 GTCATAGCCT GCGCAGGAGC CATGAAGTTG TCAAATTTCC AGGGGAAGCT TTTGATGACC
 421 GTCAACAACA CGGACATTGC AGACGTTATC GTGATTCCCA CCTCAAAAGG AGAGAACAGA
 481 TGTTGGGTCC GGGCAATCGA CGTCGGCTAC ATGTGTGAGG ACACTATCAC GTACGAATGT
 541 CCTAAGCTCA CCATGGGCAA TGATCCAGAG GACGTGGACT GTTGGTGTGA CAACCAAGAA
 601 GTCTACGTCC AATATGGACG GTGCACGCGG ACCAGGCATT CCAAGCGAAG CAGGAGATCC
 661 GTGTCGGTCC AAACACATGG GGAGAGTTCA CTAGTGAATA AAAAAGAGGC TTGGCTGGAT
 721 TCAACGAAAG CCACAGATA CCTCATGAAA ACTGAGAACT GGATCGTAAG GAATCCTGGC
 781 TATGCTTTCC TGGCGGCGAT ACTTGGCTGG ATGCTTGGCA GTAACAACGG TCAACGCGTG
 841 GTATTCACCA TCCTCCTGCT GTTGGTCGCT CCGGCTTACA GTTTCAACTG TCTGGGAATG
 901 GGCAATCGTG ACTTCATAGA AGGAGCCAGT GGAGCCACTT GGGTGGACTT GGTGCTAGAA
 961 GGAGACAGCT GCTTGACAAT TATGGCAAAC GACAAACCAA CATTGGACGT CCGCATGATC
1021 AACATCGAAG CTGTCCAACT TGCTGAGGTC AGAAGTTACT GCTATCATGC TTCAGTCACT
1081 GACATTTCGA CGGTGGCTCG GTGCCCCACG ACTGGAGAAG CTCACAACGA GAAGCGAGCT
1141 GATAGTAGCT ATGTGTGCAA ACAAGGCTTC ACTGATCGTG GGTGGGGCAA CGGATGTGGA
1201 CTTTTCGGGA AGGGAAGCAT TGACACATGT GCAAAATTCT CCTGCACCAG TAAGGCGATT
1261 GGGAGAACAA TCCAGCCAGA AAACATCAAA TACGAAGTTG GCATTTTTGT GCATGGAACC
1321 ACCACTTCGG AAAACCATGG GAATTATTCA GCGCAAGTTG GGGCGTCCCA GGCGGCAAAG
1381 TTTACAGTAA CACCCAATGC TCCTTCGATA ACCCTTAAAC TTGGTGACTA CGGAGAAGTC
1441 ACACTGGACT GTGAGCCAAG GAGTGGACTA AACACTGAAG CGTTTTACGT CATGACCGTG
1501 GGGTCAAAGT CATTTTTGGT CCACAGGGAA TGGTTTCATG ATCTCGCTCT CCCTTGGACG
1561 CCCCCTTCGA GCACAGCGTG GAGAAACAGA GAACTCCTCA TGGAATTTGA AGAGGCGCAC
1621 GCCACAAAAC AGTCCGTTGT TGCTCTTGGG TCACAGGAAG GAGGCCTCA TCAGGCGTTG
1681 GCAGGAGCCA TCGTGGTGGA GTACTCAAGC TCAGTGAAGT TAACATCAGG CCACCTAAAA
1741 TGCAGGCTGA AAATGGACAA ACTGGCTCTG AAAGGCACAA CCTATGGCAT GTGCACAGAA
1801 AAATTCTCGT TCGCGAAAAA TCCGGCGGAC ACTGGTCACG GAACAGTTGT CATTGAACTT
1861 TCCTACTCTG GGAGTGATGG CCCTTGCAAA ATTCCGATTG TCTCCGTTGC GAGCCTCAAT
1921 GACATGACCC CCGTCGGGCG GCTGGTGACA GTGAACCCCT TCGTCGCGAC TTCCAGCGCC
1981 AACTCAAAGG TGCTAGTCGA GATGGAACCC CCCTTCGGAG ACTCCTACAT CGTAGTTGGA
2041 AGGGGAGACA AGCAGATTAA CCACCATTGG CACAAGGCTG GAAGCACGCT GGGCAAAGCC
2101 TTTTCAACGA CTTTGAAGGG AGCTCAAAGA CTGGCAGCGT GGGCGACAC AGCCTGGGAC
2161 TTTGGCTCTA TTGGAGGGGT TTTCAACTCC ATAGGGAAAG CCGTTCACCA AGTGTTTGGT
2221 GGTGCCTTCA GAACACTCTT CGGGGGAATG TCTTGGATCA CACAAGGGCT AATGGGGGCC
2281 CTACTACTCT GGATGGGCGT TAACGCACGA GACCGATCAA TTGCTTTGGC CTTCTTAGCC
2341 ACAGGAGGTG TGCTCGTGTT CTTAGCGACC AATGTGCATG CTGACACTGG ATGTGCCATT
2401 GACATCACAA GAAAAGAGAT GAGGTGTGGA AGTGGCATCT TCGTGCACAA CGACGTGGAA
2461 GCCTGGGTGG ATAGGTATAA ATATTTGCCA GAAACGCCCA GATCCCTGGC GAAGATCGTC
2521 CACAAAGCGC ACAAGGAAGG CGTGTGCGGA GTCAGATCTG TCACCAGACT GGAGCACCAA
2581 ATGTGGGAAG CCGTACGGGA CGAATTGAAC GTCCTACTCA AAGAGAACGC AGTGGACCTC
2641 AGCGTGGTGG TGAACAAGCC CGTGGGGAGA TATCGCTCAG CCCCTAAACG CCTATCCATG
2701 ACGCAAGAGA AGTTTGAAAT GGGCTGGAAA GCATGGGGAA AAAGCATTCT CTATGCCCCG
2761 GAATTGGCTA ACTCCACATT TGTCGTAGAT GGACCTGAGA CAAAGGAATG CCCTGATGAG
2821 CACAGAGCTT GGAACAGCAT GCAAATCGAA GACTTCGGCT TGGCATCAC ATCAACCCGT
2881 GTGTGGCTGA AGATCAGAGA GGAGAGCACT GACGAGTGTG ATGGAGCGAT CATAGGCACG
2941 GCTGTCAAAG GACATGTGGC AGTCCATAGT GACTTGTCGT ACTGGATTGA GAGTCGCTAC
3001 AACGACACAT GGAAACTTGA GAGGGCAGTC TTTGGAGAGG TCAAATCTTG CACTTGGCCA
```

FIG. 17A

```
3061 GAGACACACA CCCTTTGGGG AGATGGTGTT GAGGAAAGTG AACTCATCAT TCCGCATACC
3121 ATAGCCGGAC CAAAAAGCAA GCACAATCGG AGGGAAGGGT ATAAGACACA AAACCAGGGA
3181 CCCTGGGACG AGAATGGTAT AGTCTTGGAC TTTGATTATT GCCCAGGGAC AAAAGTCACC
3241 ATTACAGAGG ATTGTGGCAA GAGAGGCCCT TCGGTCAGAA CCACTACTGA CAGTGGAAAG
3301 TTGATCACTG ACTGGGTCTG TCGCAGTTGC TCCCTTCCGC CCCTACGATT CCGGACAGAA
3361 AATGGCTGCT GGTACGGAAT GGAAATCAGA CCTGTCAGGC ATGATGAAAC AACACTCGTC
3421 AGATCACAGG TTGATGCTTT TAATGGTGAA ATGGTTGACC CTTTTCAGCT GGGCCTTCTG
3481 GTGATGTTTC TGGCCACCCA GGAGGTCCTT CGCAAGAGGT GGACGGCCAG ATTGACTATT
3541 CCCGCGGTTT TGGGGGCCCT ACTTGTGCTG ATGCTTGGGG GCATCACTTA CACTGATTTG
3601 GCGAGGTATG TGGTGCTAGT CGCTGCTGCT TTCGCAGAAG CCAACAGTGG AGGAGACGTG
3661 CTGCACCTTG CTTTGATTGC CGTTTTTAAG ATCCAACCAG CATTTCTAGT GATGAACATG
3721 CTTAGCACGA GATGGACGAA CCAAGAAAAC GTGGTTCTGG TCCTAGGGGC TGCCTTTTTT
3781 CAATTAGCCT CAGTAGATCT GCAAATAGGA GTCCACGGAA TCCTGAATGC CGCCGCTATA
3841 GCATGGATGA TTGTCCGAGC GATCACTTTC CCCACAACCT CCTCCGTCAC CATGCCAGTC
3901 TTAGCGCTTC TAACTCCGGG AATGAGGGCT CTATACCTAG ACACTTACAG AATCATCCTC
3961 CTCGTCATAG GGATTTGCTC CCTGCTGCAA GAGAGGAAAA AGACCATGGC AAAAAAGAAA
4021 GGAGCTGTAC TCTTGGGCTT AGCGCTCACA TCCACTGGAT GGTTCTCGCC CACCACTATA
4081 GCTGCCGGAC TAATGGTCTG CAACCCAAAC AAGAAGAGAG GGTGGCCAGC TACTGAGTTT
4141 TTGTCGGCAG TTGGATTGAT GTTTGCCATC GTAGGTGGTT TGGCCGAGTT GGATATTGAA
4201 TCCATGTCAA TACCCTTCAT GCTGGCAGGT CTTATGGCAG TGTCCTACGT GGTGTCAGGA
4261 AAAGCAACAG ATATGTGGCT TGAACGGGCC GCCGACATCA GCTGGGAGAT GGATGCTGCA
4321 ATCACAGGAA GCAGTCGGAG GCTGGATGTG AAGCTGGATG ATGACGGAGA TTTTCACTTG
4381 ATTGATGATC CCGGTGTTCC ATGGAAGGTC TGGGTCTTGC GCATGTCTTG CATTGGCTTA
4441 GCCGCCCTCA CGCCTTGGGC CATTGTTCCC GCCGCTTTTG GTTATTGGCT CACTTTAAAA
4501 ACAACAAAAA GA
```

FIG. 17B

```
JEV                  C      prM    E              NS1         NS2A  NS2B vP825                C      prM    E              NS1         NS2A vP555                       prM    E              NS1         NS2A
(vP908)
(vCP107)

vP829                       prM    E
(vP923)

```
3332 AGATCTTGCA CGTTACCCCC CCTACGTTTC AAAGGAGAAG ACGGGTGCTG GTACGGCATG
3392 GAAATCAGAC CAGTCAAGGA GAAGGAAGAG AACCTAGTTA AGTCAATGGT CTCTGCAGGG
3452 TCAGGAGAAG TGGACAGTTT TTCACTAGGA CTGCTATGCA TATCAATAAT GATCGAAGAG
3512 GTAATGAGAT CCAGATGGAG CAGAAAAATG CTGATGACTG AACATTGGC TGTGTTCCTC
3572 CTTCTCACAA TGGGACAATT GACATGGAAT GATCTGATCA GGCTATGTAT CATGGTTGGA
3632 GCCAACGCTT CAGACAAGAT GGGGATGGGA ACAACGTACC TAGCTTTGAT GGCCACTTTC
3692 AGAATGAGAC CAATGTTCGC AGTCGGGCTA CTGTTTCGCA GATTAACATC TAGAGAAGTT
3752 CTTCTTCTTA CAGTTGGATT GAGTCTGGTG GCATCTGTAG AACTACCAAA TTCCTTAGAG
3812 GAGCTAGGGG ATGGACTTGC AATGGGCATC ATGATGTTGA AATTACTGAC TGATTTTCAG
3872 TCACATCAGC TATGGGCTAC CTTGCTGTCT TTAACATTTG TCAAAACAAC TTTTTCATTG
3932 CACTATGCAT GGAAGACAAT GGCTATGATA CTGTCAATTG TATCTCTCTT CCCTTTATGC
3992 CTGTCCACGA CTTCTCAAAA AACAACATGG CTTCCGGTGT TGCTGGGATC TCTTGGATGC
4052 AAACCACTAA CCATGTTTCT TATAACAGAA AACAAATCT GGGGAAGGAA AAGCTGGCCT
4112 CTCAATGAAG GAATTATGGC TGTTGGAATA GTTAGCATTC TTCTAAGTTC ACTTCTCAAG
4172 AATGATGTGC CACTAGCTGG CCCACTAATA GCTGGAGGCA TGCTAATAGC ATGTTATGTC
4232 ATACCTGGAA GCTCGGCCGA TTTATCACTG GAGAAAGCGG CTGAGGTCTC CTGGGAAGAA
4292 GAAGCAGAAC ACTCTGGTGC CTCACACAAC ATACTAGTGG AGGTCCAAGA TGATGGAACC
4352 ATGAAGATAA AGGATGAAGA GAGAGATGAC ACACTCACCA TTCTCCTCAA AGCAACTCTG
4412 CTAGCAATCT CAGGGGTATA CCCAATGTCA ATACCGGCGA CCCTCTTTGT GTGGTATTTT
4472 TGGCAGAAAA AAAAACAGAG ATCAGGAGTG CTATGGGACA CACCCAGCCC TCCAGAAGTG
4532 GAAAGAGCAG TCCTTGATGA TGGCATTTAT AGAATTCTCC AAAGAGGATT GTTGGGCAGG
4592 TCTCAAGTAG GAGTAGGAGT TTTTCAAGAA GGCGTGTTCC ACACAATGTG GCACGTCACC
4652 AGGGGAGCTG TCCTCATGTA CCAAGGGAAG AGACTGGAAC CAAGTTGGGC CAGTGTTAAA
4712 AAAGACTTGA TCTCATATGG AGGAGGTTGG AGGTTTCAAG GATCCTGGAA CGCGGGAGAA
4772 GAAGTGCAGG TGATTGCTGT TGAACCGGGG AAGAACCCCA AAAATGTACA GACAGCGCCG
4832 GGTACCTTCA AGACCCCTGA AGGCGAAGTT GGAGCCATAG CTCTAGACTT TAAACCCGGC
4892 ACATCTGGAT CTCCTATCGT GAACAGAGAG GGAAAAATAG TAGGTCTTTA TGGAAATGGA
4952 GTGGTGACAA CAAGTGGTAC CTACGTCAGT GCCATAGCTC AAGCTAAAGC ATCACAAGAA
5012 GGGCCTCTAC CAGAGATTGA GGACGAGGTG TTTAGGAAAA GAAACTTAAC AATAATGGAC
5072 CTACATCCAG GATCGGGAAA AACAAGAAGA TACCTTCCAG CCATAGTCCG TGAGGCCATA
5132 AAAAGAAAGC TGCGCACGCT AGTCTTAGCT CCCACACAGAG TTGTCGCTTC TGAAATGGCA
5192 GAGGCGCTCA AGGGAATGCC AATAAGGTAT CAGACAACAG CAGTGAAGAG TGAACACACG
5252 GGAAAGGAGA TAGTTGACCT TATGTGTCAC GCCACTTTCA CTATGCGTCT CCTGTCTCCT
5312 GTGAGAGTTC CAAGGATAA TATGATTATC ATGGATGAAG CACATTTCAC CGATCCAGCC
5372 AGCATAGCAG CCAGAGGGTA TATCTCAACC CGAGTGGGTA TGGGTGAAGC AGCTGCGATT
5432 TTCATGACAG CCACTCCCCC CGGATCGGTG GAGGCCTTTC CACAGAGCAA TGCAGTTATC
5492 CAAGATGAGG AAAGAGACAT TCCTGAAAGA TCATGGAACT CAGGCTATGA CTGGATCACT
5552 GATTTCCCAG GTAAACAGT CTGGTTTGTT CCAAGCATCA AATCAGGAAA TGACATTGCC
5612 AACTGTTTAA GAAAGAATGG GAAACGGGTG GTCCAATTGA GCAGAAAAAC TTTTGACACT
5672 GAGTACCAGA AAACAAAAAA TAACGACTGG GACTATGTTG TCACAACAGA CATATCCGAA
5732 ATGGGAGCAA ACTTCCGAGC CGACAGGGTA ATAGACCCGA GGCGGTGCCT GAAACCGGTA
5792 ATACTAAAAG ATGGCCCAGA GCGTGTCATT CTAGCCGGAC CGATGCCAGT GACTGTGTAC
5852 GCCGCCCAGA GGAGACGAAG AATTGGAAGG AACCAAAATA AGGAAGGCGA TCAGTATATT
5912 TACATGGGAC AGCCTCTAAA CAATGATGAG GACCACGCCC ATTGGACAGA AGCAAAAATG
5972 CTCCTTGACA ACATAAACAC ACCAGAAGGG ATTATCCCAG CCCTCTTTGA GCCGGAGAGA
6032 GAAAAGAGTG CAGCAATAGA CGGGGAATAC AGACTACGGG GTGAAGCGAG GAAAACGTTC
6092 GTGGAGCTCA TGAGAAGAGG AGATCT
```

FIG. 20

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTATGACAA TAAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT CAGAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGGTGTTGA GAGACGACTA CAAAATAGTG
1021 AAAGATCTGT TGAAGAATAA CTATGTAAAC AATGTTCTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAAGCTG TTAATCGATC ATGGAGCTGA TGTAAACTCT TTAACTATTG
2581 CTAAAGATAA TCTTATTAAA AAAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAATAGGA TGTAAGAACT TACTAGAATG TTTTATCAAT AATGATATGA ATACAGTATC
2821 TAGGGCTATA AACAATGAAA CGATTAAAAA TTATAAAAAT CATTTCCCTA TATATAATAC
2881 GCTCATAGAA AAATTCATTT CTGAAAGTAT ACTAAGCACG AATTATTGG ATGGAGTTAT
2941 AAATTCTTTT CAAGGATTCA ATAATAAATT GCCTTACGAG ATTCAGTACA TTATACTGGA
3001 GAATCTTAAT AACCATGAAC TAAAAAAAAT TTTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

FIG. 22

```
   1 AGATATTTGT TAGCTTCTGC CGGAGATACC GTGAAAATCT ATTTTCTGGA AGGAAAGGGA
  61 GGTCTTATCT ATTCTGTCAG CAGAGTAGGT TCCTCTAATG ACGAAGACAA TAGTGAATAC
 121 TTGCATGAAG GTCACTGTGT AGAGTTCAAA ACTGATCATC AGTGTTTGAT AACTCTAGCG
 181 TGTACGAGTC CTTCTAACAC TGTGGTTTAT TGGCTGGAAT AAAAGGATAA AGACACCTAT
 241 ACTGATTCAT TTTCATCTGT CAACGTTTCT CTAAGAGATT CATAGGTATT ATTATTACAT
 301 CGATCTAGAA GTCTAATAAC TGCTAAGTAT ATTATTGGAT TTAACGCGCT ATAAACGCAT
 361 CCAAAACCTA CAAATATAGG AGAAGCTTCT CTTATGAAAC TTCTTAAAGC TTTACTCTTA
 421 CTATTACTAC TCAAAAGAGA TATTACATTA ATTATGTGAT GAGGCATCCA ACATATAAAG
 481 AAGACTAAAG CTGTAGAAGC TGTTATGAAG AATATCTTAT CAGATATATT AGATGCATTG
 541 TTAGTTCTGT AGATCAGTAA CGTATAGCAT ACGAGTATAA TTATCGTAGG TAGTAGGTAT
 601 CCTAAAATAA ATCTGATACA GATAATAACT TTGTAAATCA ATTCAGCAAT TTCTCTATTA
 661 TCATGATAAT GATTAATACA CAGCGTGTCG TTATTTTTTG TTACGATAGT ATTTCTAAAG
 721 TAAAGAGCAG GAATCCCTAG TATAATAGAA ATAATCCATA TGAAAAATAT AGTAATGTAC
 781 ATATTTCTAA TGTTAACATA TTTATAGGTA AATCCAGGAA GGGTAATTTT TACATATCTA
 841 TATACGCTTA TTACAGTTAT TAAAAATATA CTTGCAAACA TGTTAGAAGT AAAAAAGAAA
 901 GAACTAATTT TACAAAGTGC TTTACCAAAA TGCCAATGGA AATTACTTAG TATGTATATA
 961 ATGTATAAAG GTATGAATAT CACAAACAGC AAATCGGCTA TTCCCAAGTT GAGAAACGGT
1021 ATAATAGATA TATTTCTAGA TACCATTAAT AACCTTATAA GCTTGACGTT TCCTATAATG
1081 CCTACTAAGA AAACTAGAAG ATACATACAT ACTAACGCCA TACGAGAGTA ACTACTCATC
1141 GTAAACTAC TGTTGCTAAC AGTGACACTG ATGTTATAAC TCATCTTTGA TGTGGTATAA
1201 ATGTATAATA ACTATATTAC ACTGGTATTT TATTTCAGTT ATATACTATA TAGTATTAAA
1261 AATTATATTT GTATAATTAT ATTATTTATAT TCAGTGTAGA AAGTAAAATA CTATAAATAT
1321 GTATCTCTTA TTTATAACTT ATTAGTAAAG TATGTACTAT TCAGTTATAT TGTTTTATAA
1381 AAGCTAAATG CTACTAGATT GATATAAATG AATATGTAAT AAATTAGTAA TGTAGTATAC
1441 TAATATTAAC TCACATTATG AATACTACTA ATCACGAAGA ATGCAGTAAA ACATATGATA
1501 CAAACATGTT AACAGTTTTA AAAGCCATTA GTAATAAACA GTACAATATA ATTAAGTCTT
1561 TACTTAAAAA AGATATTAAT GTTAATAGAT TATTAACTAG TTATTCTAAC GAAATATATA
1621 AACATTTAGA CATTACATTA TGTAATATAC TTATAAACTG TGCAGCAGAC ATAAACATTA
1681 TAGATAAGAA CAATCGTACA CCGTTGTTTT ATGCGGTAAA GAATAGATGAT TATGATATGG
1741 TTAAACTCCT ATTAAAAAAT GGCGCGAATG TAAATTTACA AGATAGTATA GGATATTCAT
1801 GTCTTCACAT CGCAGGTATA CATAAGTAGTA ACATAGAAAT AGTAGATGCA TTGATATCAT
1861 ACAAACCAGA TTTAAACTCC CGCGATTGGG TAGGTAGAAC ACCGCTACAT ATCTTCGTGA
1921 TAGAATCTAA CTTTGAAGCT GTGAAATTAT TATTAAAGTC AGGTGCATAT GTAGGTTTGA
1981 AAGACAAATG TAAGCATTTT CCTATACACC ATTCTGTAAT GAAATTAGAT CACTTAATAT
2041 CAGGATTGTT ATTAAAATAT GGAGCAAATC CAAATACAAT TAACGGCAAT GGAAAAACAT
2101 TATTAAGCAT TGCTGTAACA TCTAATAATA CACTACTGGT AGAACAGCTG CTGTTATATG
2161 GAGCAGAAGT TAATAATGGT GGTTATGATG TTCCAGCTCC TATTATATCC GCTGTCAGTG
2221 TTAACAATTA TGATATTGTT AAGATACTGA TACATAATGG TGCGAATATA AATGTATCCA
2281 CGGAAGATGG TAGAACGTCT TTACATACAG CTATGTTTTG GAATAACGCT AAAATAATAG
2341 ATGAGTTGCT TAACTATGGA AGTGACATAA ACAGCGTAGA TACTTATGGT AGAACTCCGT
2401 TATCTTGTTA TCGTAGCTTA AGTTATGATA TCGCTACTAA ACTAATATCA CGTATCATTA
2461 TAACAGATGT CTATCGTGAA GCACCAGTAA ATATCAGCGG ATTTATAATT AATTTAAAAA
2521 CTATAGAAAA TAATGATATA TTCAAATTAA TTAAGATGA TTGTATTAAA GAGATAAACA
2581 TACTTAAAAG TATAACCCTT AATAAATTTC ATTCATCTGA CATATTTATA CGATATAATA
2641 CTGATATATG TTTATTAACG AGATTTATTC AACATCCAAA GATAATAGAA CTAGACAAAA
2701 AACTCTACGC TTATAAATCT ATAGTCAACG AGAGAAAAAT CAAAGCTACT TACAGGTATT
2761 ATCAAATAAA AAAAGTATTA ACTGTACTAC CTTTTTCAGG ATATTTCTCT ATATTGCCGT
2821 TTGATGTGTT AGTATATATA CTTGAATTCA TCTATGATAA TAATATGTTG GTACTTATGA
2881 GAGCGTTATC ATTAAAATGA AATAAAAAGC ATACAAGCTA TTGCTTCGCT ATCGTTACAA
2941 AATGGCAGGA ATTTTGTGTA AACTAAGCCA CATACTTGCC AATGAAAAAA ATAGTAGAAA
3001 GGATACTATT TTAATGGGAT TAGATGTTAA GGTTCCTTGG GATTATAGTA ACTGGGCATC
```

FIG. 24A

```
3061 TGTTAACTTT TACGACGTTA GGTTAGATAC TGATGTTACA GATTATAATA ATGTTACAAT
3121 AAAATACATG ACAGGATGTG ATATTTTTCC TCATATAACT CTTGGAATAG CAAATATGGA
3181 TCAATGTGAT AGATTTGAAA ATTTCAAAAA GCAAATAACT GATCAAGATT TACAGACTAT
3241 TTCTATAGTC TGTAAAGAAG AGATGTGTTT TCCTCAGAGT AACGCCTCTA AACAGTTGGG
3301 AGCGAAAGGA TGCGCTGTAG TTATGAAACT GGAGGTATCT GATGAACTTA GAGCCCTAAG
3361 AAATGTTCTG CTGAATGCGG TACCCTGTTC GAAGGACGTG TTTGGTGATA TCACAGTAGA
3421 TAATCCGTGG AATCCTCACA TAACAGTAGG ATATGTTAAG GAGGACGATG TCGAAAACAA
3481 GAAACGCCTA ATGGAGTGCA TGTCCAAGTT TAGGGGGCAA GAAATACAAG TTCTAGGATG
3541 GTATTAATAA GTATCTAAGT ATTTGGTATA ATTTATTAAA TAGTATAATT ATAACAAATA
3601 ATAAATAACA TGATAACGGT TTTTATTAGA ATAAAATAGA GATAATATCA TAATGATATA
3661 TAATACTTCA TTACCAGAAA TGAGTAATGG AAGACTTATA AATGAACTGC ATAAAGCTAT
3721 AAGGTATAGA GATATAAATT TAGTAAGGTA TATACTTAAA AAATGCAAAT ACAATAACGT
3781 AAATATACTA TCAACGTCTT TGTATTTAGC CGTAAGTATT TCTGATATAG AAATGGTAAA
3841 ATTATTACTA GAACACGGTG CCGATATTTT AAAATGTAAA AATCCTCCTC TTCATAAAGC
3901 TGCTAGTTTA GATAATACAG AAATTGCTAA ACTACTAATA GATTCTGGCG CTGACATAGA
3961 ACAGATACAT TCTGGAAATA GTCCGTTATA TATTTCTGTA TATAGAAACA ATAAGTCATT
4021 AACTAGATAT TTATTAAAAA AAGGTGTTAA TTGTAATAGA TTCTTTCTAA ATTATTACGA
4081 TGTACTGTAT GATAAGATAT CTGATGATAT GTATAAAATA TTTATAGATT TTAATATTGA
4141 TCTTAATATA CAAACTAGAA ATTTTGAAAC TCCGTTACAT TACGCTATAA AGTATAAGAA
4201 TATAGATTTA ATTAGGATAT TGTTAGATAA TAGTATTAAA ATAGATAAAA GTTTATTTTT
4261 GCATAAACAG TATCTCATAA AGGCACTTAA AAATAATTGT AGTTACGATA TAATAGCGTT
4321 ACTTATAAAT CACGGAGTGC CTATAAACGA ACAAGATGAT TTAGGTAAAA CCCCATTACA
4381 TCATTCGGTA ATTAATAGAA GAAAAGATGT AACAGCACTT CTGTTAAATC TAGGAGCTGA
4441 TATAAACGTA ATAGATGACT GTATGGGCAG TCCCTTACAT TACGTCGTTT CACGTAACGA
4501 TATCGAAACA ACAAAGACAC TTTTAGAAAG AGGATCTAAT GTTAATGTGG TTAATAATCA
4561 TATAGATACC GTTCTAAATA TAGCTGTTGC ATCTAAAAAC AAAACTATAG TAAACTTATT
4621 ACTGAAGTAC GGTACTGATA CAAAGTTGGT AGGATTAGAT AAACATGTTA TTCACATAGC
4681 TATAGAAATG AAAGATATTA ATATACTGAA TGCGATCTTA TTATATGGTT GCTATGTAAA
4741 CGTCTATAAT CATAAAGGTT TCACTCCTCT ATACATGGCA GTTAGTTCTA TGAAAACAGA
4801 ATTTGTTAAA CTCTTACTTG ACCACGGTGC TTACGTAAAT GCTAAAGCTA AGTTATCTGG
4861 AAATACTCCT TTACATAAAG CTATGTTATC TAATAGTTTT AATAATATAA AATTACTTTT
4921 ATCTTATAAC GCCGACTATA ATTCTCTAAA TAATCACGGT AATACGCCTC TAACTTGTGT
4981 TAGCTTTTTA GATGACAAGA TAGCTATTAT GATAATATCT AAAATGATGT TAGAAATATC
5041 TAAAAATCCT GAAATAGCTA ATTCAGAAGG TTTTATAGTA AACATGGAAC ATATAACAG
5101 TAATAAAGA CTACTATCTA TAAAAGAATC ATGCGAAAAA GAACTAGATG TTATAACACA
5161 TATAAAGTTA AATTCTATAT ATTCTTTTAA TATCTTTCTT GACAATAACA TAGATCTTAT
5221 GGTAAAGTTC GTAACTAATC CTAGAGTTAA TAAGATACCT GCATGTATAC GTATATATAG
5281 GGAATTAATA CGGAAAAATA AATCATTAGC TTTTCATAGA CATCAGCTAA TAGTTAAAGC
5341 TGTAAAAGAG AGTAAGAATC TAGGAATAAT AGGTAGGTTA CCTATAGATA TCAAACATAT
5401 AATAATGGAA CTATTAAGTA ATAATGATTT ACATTCTGTT ATCACCAGCT GTTGTAACCC
5461 AGTAGTATAA AGTGATTTTA TTCAATTACG AAGATAAACA TTAAATTTGT TAACAGATAT
5521 GAGTTATGAG TATTTAACTA AAGTTACTTT AGGTACAAAT AAAATATTAT GTAATATAAT
5581 AGAAAATTAT CTTGAGTCTT CATTTCCATC ACCGTCTAAA TTTATTATTA AAACCTTATT
5641 ATATAAGGCT GTTGAGTTTA GAAATGTAAA TGCTGTAAAA AAATATTAC AGAATGATAT
5701 TGAATATGTT AAAGTAGATA GTCATGGTGT CTCGCCTTTA CATATTATAG CTATGCCTTC
5761 AAATTTTTCT CTCATAGACG TGAACATGTA TTCAGAATTT ACGAGTTAGT AATGAAATTA GTAATAGACT
5821 TCAAAAATCT AAAGATAGTA ACGAATTTCA ACGAGTTAGT CTACTAAGGA CAATTATAGA
5881 ATATGGTAAT GATAGTGATA TTAATAAGTG TCTAACATTA GTAAAAACGG ATATACAGAG
5941 TAACGAAGAG ATAGATATTA TAGATCTTTT GATAAATAAA GGAATAGATA TAAATATTAA
6001 AGACGATTTA GGAAACACAG CTTTGCATTA CTCGTGTGAT TATGCTAAGG GATCAAAGAT
6061 AGCTAAAAAG TTACTAGATT GTGGAGCAGA TCCTAACATA GTTAATGATT TAGGTGTTAC
```

FIG. 24B

```
6121 ACCACTAGCG TGTGCCGTTA ATACTTGCAA CGAGATACTA GTAGATATTC TGTTAAATAA
6181 TGATGCGAAT CCTGATTCAT CTTCCTCATA TTTTTTAGGT ACTAATGTGT TACATACAGC
6241 CGTAGGTACC GGTAATATAG ATATTGTAAG ATCTTTACTT ACGGCTGGTG CCAATCCTAA
6301 TGTAGGAGAT AAATCTGGAG TTACTCCTTT GCACGTTGCT GCAGCTGATA AAGACAGTTA
6361 TCTGTTAATG GAGATGCTAC TAGATAGCGG GGCAGATCCA AATATAAAAT GCGCAAACGG
6421 TTTTACTCCT TTGTTTAATG CAGTATATGA TCATAACCGT ATAAAGTTAT TATTTCTTTA
6481 CGGGGCTGAT ATCAATATTA CTGACTCTTA CGGAAATACT CCTCTTACTT ATATGACTAA
6541 TTTTGATAAT AAATATGTAA ATTCAATAAT TATCTTACAA ATATATCTAC TTAAAAAAGA
6601 ATATAACGAT GAAAGATTGT TTCCACCTGG TATGATAAAA AATTTAAACT TTATAGAATC
6661 AAACGATAGT CTTAAAGTTA TAGCTAAAAA GTGTAATTCG TTAATACGCT ATAAGAAAAA
6721 TAAAGACATA GATGCAGATA ACGTATTATT GGAGCTTTTA GAGGAAGAGG AAGAAGATGA
6781 AATAGACAGA TGGCATACTA CATGTAAAAT ATCTTAAATA GTAATTAAAT CATTGAAATA
6841 TTAACTTACA AGATGATCGA GGTCACTTAT TATACTCTTT AATAATGGGT ACAAAGAGTA
6901 TTCATACGTT AGTTAAATCT AACGATGTAA TACGTGTTCG TGAATTAATA AAGGATGATA
6961 GATGTTTGAT AAATAAAAGA AATAGAAGAA ATCAGTCACC TGTATATATA GCTATATACA
7021 AAGGACTTTA TGAAATGACT GAAATGTTAT TGCTAAATAA TGCAAGTCTA GATACTAAAA
7081 TACCTTCTTT AATTATAGCA GCTAAAAATA ATGACTTACC TATGATAAAA TTATTGATAC
7141 AATACGGGGC AAAATTAAAT GATATTTATT TAAGGGACAC AGCATTAATG ATAGCTCTCA
7201 GAAATGGTTA CCTAGATATA GCTGAATATT TACTTTCATT AGGAGCAGAA TTTGTTAAAT
7261 ACAGACATAA GGTAATATAT AAATATCTAT CAAAAGATGC GTATGAATTA CTTTTTAGAT
7321 TTAATTATGA CGTTAATATA ATAGATTGAG A
```

FIG. 24C

FLAVIVIRUS RECOMBINANT POXVIRUS IMMUNOLOGICAL COMPOSITION

This application is a division of U.S. application Ser. No. 08/224,391 filed Apr. 7, 1994, now U.S. Pat. No. 5,744,140, which in turn is a continuation of U.S. application Ser. No. 07/629,800 filed Jul. 17, 1991, now abandoned which in turn is a continuation-in-part of U.S. application Ser. No. 07/714, 687 filed Jun. 13, 1991, now U.S. Pat. No. 5,514,375, which in turn is a continuation-in-part of U.S. application Ser. No. 07/711,429 filed Jun. 6, 1991 now abandoned, which in turn is a continuation-in-part of U.S. application Ser. No. 07/567, 960 filed Aug. 15, 1990, which is now abandoned. Application Ser. No. 07/714,687 is also a continuation-in-part of application Ser. No. 07/713,967, filed Jun. 11, 1991, now abandoned, which in turn is a continuation-in-part of application Ser. No. 07/666,056, filed Mar. 7, 1991, now abandoned. This application is also a continuation-in-part of application Ser. No. 08/105,483, filed Aug. 12, 1993, now U.S. Pat. No. 5,494,807, which in turn is a continuation of application Ser. No. 847,951, filed Mar. 6, 1992, now abandoned, which is a continuation-in-part of application Ser. No. 07/713,967, filed Jun. 11, 1991, now abandoned, which in turn is a continuation-in-part of application Ser. No. 07/666,056, filed Mar. 7, 1991, now abandoned, in favor of continuation application Ser. No. 08/036,217, filed Mar. 24, 1993, now U.S. Pat. No. 5,364,773.

FIELD OF THE INVENTION

The present invention relates to a modified poxvirus and to methods of making and using the same. More in particular, the invention relates to recombinant poxvirus, which virus expresses gene products of a flavivirus gene, and to vaccines which provide protective immunity against flavivirus infections.

Several publications are referenced in this application. Full citation to these references is found at the end of the specification preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted.

Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1986).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The family Flaviviridae comprises approximately 60 arthropod-borne viruses that cause significant public health problems in both temperate and tropical regions of the world (Shope, 1980; Monath, 1986). Although some highly successful inactivated vaccines and live-attenuated vaccines have been developed against some of these agents, there has been a recent surge in the study of the molecular biology of flaviviruses in order to produce recombinant vaccines to the remaining viruses, most notably dengue (Brandt, 1988).

Flavivirus proteins are encoded by a single long translational open reading frame (ORF) present in the positive-strand genomic RNA. The genes encoding the structural proteins are found at the 5' end of the genome followed by the nonstructural glycoprotein NS1 and the remaining nonstructural proteins (Rice et al., 1985). The flavivirus virion contains an envelope glycoprotein, E, a membrane protein, M, and a capsid protein, C. In the case of Japanese encephalitis virus (JEV), virion preparations usually contain a small amount of the glycoprotein precursor to the membrane protein, prM (Mason et al., 1987a). Within JEV-infected cells, on the other hand, the M protein is present almost exclusively as the higher molecular weight prM protein (Mason et al., 1987a; Shapiro et al., 1972).

Studies that have examined the protective effect of passively administered monoclonal antibodies (MAbs) specific for each of the three flavivirus glycoproteins (prM, E, NS1) have demonstrated that immunity to each of these antigens results in partial or complete protection from lethal viral challenge. Monoclonal antibodies to E can provide protection from infection by Japanese encephalitis virus (JEV) (Kimura-Kuroda et al., 1988; Mason et al., 1989), dengue type 2 virus (Kaufman et al., 1987) and yellow fever virus (YF) (Gould et al., 1986). In most cases, passive protection has been correlated with the ability of these E MAbs to neutralize the virus in vitro. Recently, Kaufman et al. (1989) have demonstrated that passive protection can also be produced with prM MAbs that exhibit weak or undetectable neutralizing activity in vitro. The ability of structural protein specific MAbs to protect animals from infection is consistent with the conventional hypothesis that structural protein antibodies attenuate viral infection by blocking virus binding to target cells. Passive protection experiments using MAbs to the NS1 protein of yellow fever virus (Schlesinger et al., 1985; Gould et al., 1986) and dengue type 2 virus (Henchal et al., 1988) have demonstrated that antibodies to this nonstructural glycoprotein can protect animals from lethal viral infection. Since these MAbs do not exhibit viral binding properties, their protection is presumably mediated by some less conventional mechanism of attenuation of viral infection (Gibson et al., 1988).

Additional support for the ability of NS1 immunity to protect the host from infection comes from direct immunization experiments in which NS1 purified from either yellow fever virus-infected cells (Schlesinger et al., 1985, 1986) or dengue type 2 virus-infected cells (Schlesinger et al., 1987) induced protective immunity from infection with the homologous virus.

Although significant progress has been made in deriving the primary structure of these three flavivirus glycoprotein antigens, less is known about their three-dimensional structure. The ability to produce properly folded, and possibly correctly assembled, forms of these antigens may be important for the production of effective recombinant vaccines. In the case of NS1-based vaccines, dimerization of NS1 (Winkler et al., 1988) may be required to elicit the maximum protective response. For the E protein, correct folding is probably required for eliciting a protective immune response since E protein antigens produced in $E.\ coli$ (Mason et al., 1989) and the authentic E protein prepared under denaturing conditions (Wengler et al., 1989b) failed to induce neutralizing antibodies. Correct folding of the E protein may require the coordinated synthesis of the prM protein, since these proteins are found in heterodimers in the cell-associated forms of West Nile virus (Wengler et al., 1989a). The proper folding of E and the assembly of E and prM into viral particles may require the coordinated synthesis of the NS1 protein, which is coretained in an early compartment of the secretory apparatus along with immature forms of E in JEV-infected cells (Mason, 1989).

Attempts to produce recombinant flavivirus vaccines based on the flavivirus glycoproteins has met with some success, although protection in animal model systems has not always correlated with the predicted production of neutralizing antibodies (Bray et al., 1989; Deubel et al., 1988; Matsuura et al., 1989; Yasuda et al., 1990; Zhang et al., 1988; Zhao et al., 1987).

Yasuda et al. (1990) reported a vaccinia recombinant containing the region of JEV encoding 65 out of the 127 amino acids of C, all of prM, all of E, and 59 out of the 352 amino acids of NS1. Haishi et al. (1989) reported a vaccinia recombinant containing Japanese encephalitis sequences encoding 17 out of the 167 amino acids of prM, all of E and 57 out of the 352 amino acids of NS1.

Deubel et al. (1988) reported a vaccinia recombinant containing the dengue-2 coding sequences for all of C, all of prM, all of E and 16 out of the 352 amino acids of NS1.

Zhao et al. (1987) reported a vaccinia recombinant containing the dengue-4 coding sequences for all of C, all of prM, all of E, all of NS1, and all of NS2A. Bray et al. (1989) reported a series of vaccinia recombinants containing the dengue-4 coding sequences for (i) all of C, all of prM and 416 out of the 454 amino acids of E, (ii) 15 out of the 167 amino acids of prM and 416 out of the 454 amino acids of E, (iii) 18 amino acids of influenza A virus hemagglutinin and 416 out of the 454 amino acids of E, and (iv) 71 amino acids of respiratory syncytial virus G glycoprotein and 416 out of the 454 amino acids of E.

Despite these attempts to produce recombinant flavivirus vaccines, the proper expression of the JEV E protein by the vaccinia recombinants has not been satisfactorily obtained. Although Haishi et al. (1989) demonstrated cytoplasmic expression of JEV E protein by their vaccinia recombinant, the distribution was different from that observed in JEV infected cells. Yasuda et al. (1990) detected expression of JEV E protein by their vaccinia recombinant on the cell surface. Recombinant viruses that express the prM and E protein protected mice from approximately 10 $LD_{50}$ of challenge virus. Yasuda et al. (1990) elicited anti-JEV immune responses as well as protection but reactivity to a panel of E specific monoclonal antibodies exhibited differences from the reactivity observed in JEV infected cells.

Dengue type 2 structural proteins have been expressed by recombinant vaccinia viruses (Deubel et al., 1988). Although these viruses induced the synthesis of the structural glycoprotein within infected cells, they neither elicited detectable anti-dengue immune responses nor protected monkeys from dengue infection. Several studies also have been completed on the expression of portions of the dengue type 4 structural and nonstructural proteins in vaccinia virus (Bray et al., 1989; Falgout et al., 1989; Zhao et al., 1987). Interestingly, a recombinant that contained the entire 5' end of the viral ORF extending from C to NS2A under the control of the P7.5 early-late promoter produced intracellular forms of prM, E, and NS1 but failed to induce the synthesis of extracellular forms of any of the structural proteins, even though a form of NS1 was released from cells infected with this recombinant virus (Bray et al., 1989; Zhao et al., 1987). Additional recombinant viruses that contained several forms of the dengue type 4 E gene with or without other structural protein genes have also been examined (Bray et al., 1989). Although several of these recombinant viruses were able to induce protection, they neither produced extracellular forms of E nor induced neutralizing antibodies. A dengue-vaccinia recombinant expressing a C-terminally truncated E protein gene induced the synthesis of an extracellular form of E and provided an increasing level of resistance to dengue virus encephalitis in inoculated mice (Men et al., 1991).

It can thus be appreciated that provision of a flavivirus recombinant poxvirus which produces properly processed forms of flavivirus proteins, and of vaccines which provide protective immunity against flavivirus infections, would be a highly desirable advance over the current state of technology.

OBJECTS OF THE INVENTION

It is therefore an object of this invention to provide recombinant poxviruses, which viruses express properly processed gene products of flavivirus, and to provide a method of making such recombinant poxviruses.

It is an additional object of this invention to provide for the cloning and expression of flavivirus coding sequences in a poxvirus vector.

It is another object of this invention to provide a vaccine which is capable of eliciting flavivirus neutralizing antibodies, hemagglutination-inhibiting antibodies and protective immunity against flavivirus infection and a lethal flavivirus challenge.

These and other objects and advantages of the present invention will become more readily apparent after consideration of the following.

STATEMENT OF THE INVENTION

In one aspect, the present invention relates to a recombinant poxvirus generating an extracellular flavivirus structural protein capable of inducing protective immunity against flavivirus infection. In particular, the recombinant poxvirus generates an extracellular particle containing flavivirus E and M proteins capable of eliciting neutralizing antibodies and hemagglutination-inhibiting antibodies. The poxvirus is advantageously a vaccinia virus or an avipox virus, such as fowlpox virus or canarypox virus. The flavivirus is advantageously Japanese encephalitis virus, yellow fever virus and Dengue virus.

According to the present invention, the recombinant poxvirus contains therein DNA from flavivirus in a nonessential region of the poxvirus genome for expressing in a host flavivirus structural protein capable of release to an extracellular medium. In particular, the DNA contains Japanese encephalitis virus coding sequences that encode a precursor to structural protein M, structural protein E, and nonstructural proteins NS1 and NS2A. More in particular, the recombinant poxvirus contains therein DNA from flavivirus in a nonessential region of the poxvirus genome for expressing a particle containing flavivirus structural protein E and structural protein M.

In another aspect, the present invention relates to a vaccine for inducing an immunological response in a host animal inoculated with the vaccine, said vaccine including a carrier and a recombinant poxvirus containing, in a nonessential region thereof, DNA from flavivirus.

More in particular, the recombinant viruses express portions of the flavivirus ORF extending from prM to NS2B. Biochemical analysis of cells infected with the recombinant viruses showed that the recombinant viruses specify the production of properly processed forms of all three flavivirus glycoproteins—prM, E, and NS1. The recombinant viruses induced synthesis of extracellular particles that contained fully processed forms of the M and E proteins. Furthermore, the results of mouse immunization studies demonstrated that the induction of neutralizing antibodies and high levels of protection were associated with the ability of the immunizing recombinant viruses to produce extracellular particles containing the two structural membrane proteins.

BRIEF DESCRIPTION OF THE DRAWINGS

A better understanding of the present invention will be had by referring to the accompanying drawings, in which:

FIG. 2 schematically shows a method for the construction of donor plasmids pSPJEV11VC and pSPJEV10VC containing coding sequences for a portion of the JEV structural protein coding region, NS1, NS2A and NS2B;

FIG. 3 shows the DNA sequence of oligonucleotides (shown with translational starts and stops in italics and early transcriptional stops underlined) used to construct the donor plasmids;

FIG. 5 shows a comparison by SDS-PAGE analysis of the cell lysate NS1 proteins produced by JEV infection and infection with the recombinant vaccinia viruses vP650, vP555, vP658 and vP583;

FIG. 6 shows a comparison by SDS-PAGE analysis of the culture fluid NS1 proteins produced by JEV infection and infection with the recombinant vaccinia viruses vP650, vP555, vP658 and vP583;

FIG. 7 shows a comparison by SDS-PAGE analysis of the cell lysate E proteins produced by JEV infection and infection with the recombinant vaccinia viruses vP650, vP555, vP658 and vP583;

FIG. 8 shows a comparison by SDS-PAGE analysis of the culture fluid E proteins produced by JEV infection and infection with the recombinant vaccinia viruses vP650, vP555, vP658 and vP583;

FIG. 9 shows a comparison by sucrose gradient analysis of the forms of the E protein found in the culture fluid harvested from JEV infected cells and cells infected with vaccinia recombinants vP555 and vP650;

FIG. 10 shows a comparison by immunoprecipitation analysis of the JEV-specific reactivity of the pre-challenge sera from animals vaccinated with JEV and with vaccinia recombinants vP555 and vP658;

FIG. 17 shows the DNA sequence of the Nakayama strain of JEV in the region encoding C through NS2B;

FIG. 18 is a map of the JEV coding regions inserted in the vaccinia viruses vP555, vP825, vP908, vP923, vP857, vP864 and canarypox virus vCP107;

FIG. 20 shows part of the DNA sequence of a Western Pacific strain of DEN type 1;

FIG. 21 is a map of the DEN coding regions inserted in the vaccinia viruses vP867, vP962 and vP955.

FIG. 22 shows the DNA sequence of a canarypox PvuII fragment containing the C5 ORF;

FIG. 24 shows the DNA sequence of a 7351 base pair fragment of canarypox containing the C3 ORF.

DETAILED DESCRIPTION OF THE INVENTION

A better understanding of the present invention and of its many advantages will be had from the following examples, given by way of illustration.

EXAMPLE 1—CLONING OF JEV GENES INTO A VACCINIA VIRUS DONOR PLASMID

A thymidine kinase mutant of the Copenhagen strain of vaccinia virus, vP410 (Guo et al., 1989), was used to generate recombinant vP658 (see below). A recombinant vaccinia virus (vP425) containing the Beta-galactosidase gene in the HA region under the control of the 11-kDa late vaccinia virus promoter (Guo et al., 1989) was used to generate recombinants vP555, vP583 and vP650. All vaccinia virus stocks were produced in either VERO (ATCC CCL81) or MRC-5 (ATCC CCL171) cells in Eagle's minimal essential medium (MEM) plus 10% heat-inactivated fetal bovine serum (FBS). Biosynthetic studies were performed using baby hamster kidney cells (BHK 21-15 clone) grown at 37° C. in MEM supplemented with 7.5% FBS and antibiotics, or VERO cells grown under the same conditions except using 5% FBS. The JEV virus used in all in vitro experiments was a clarified culture fluid prepared from C6/36 cells infected with a passage 55 suckling mouse brain suspension of the Nakayama strain of JEV (Mason, 1989).

Restriction enzymes were obtained from GIBCO/BRL, Inc., (Gaithersburg, MD), New England BioLabs, Inc. (Beverly, MA), or Boehringer Mannheim Biochemicals (Indianapolis, IN). T4 DNA ligase was obtained from New England BioLabs, Inc. Standard recombinant DNA techniques were used (Maniatis et al., 1986) with minor modifications for cloning, screening, and plasmid purification. Nucleic acid sequences were confirmed using standard dideoxy chain-termination reactions (Sanger et al., 1977) on alkaline-denatured double-stranded plasmid templates. Sequencing primers, and other oligonucleotides were synthesized using standard chemistries (Biosearch 8700, San Rafael, CA; Applied Biosystems 380B, Foster City, CA). The JEV cDNAs used to construct the JEV-vaccinia recombinant viruses were derived from the Nakayama strain of JEV (McAda et al., 1987); all nucleotide coordinates are derived from the sequence data presented in FIG. 17A and B (SEQ ID NO:52) which contains the sequence of the C coding region combined with an updated sequence of prM, E, NS1, NS2A and NS2B coding regions.

Figure 1:
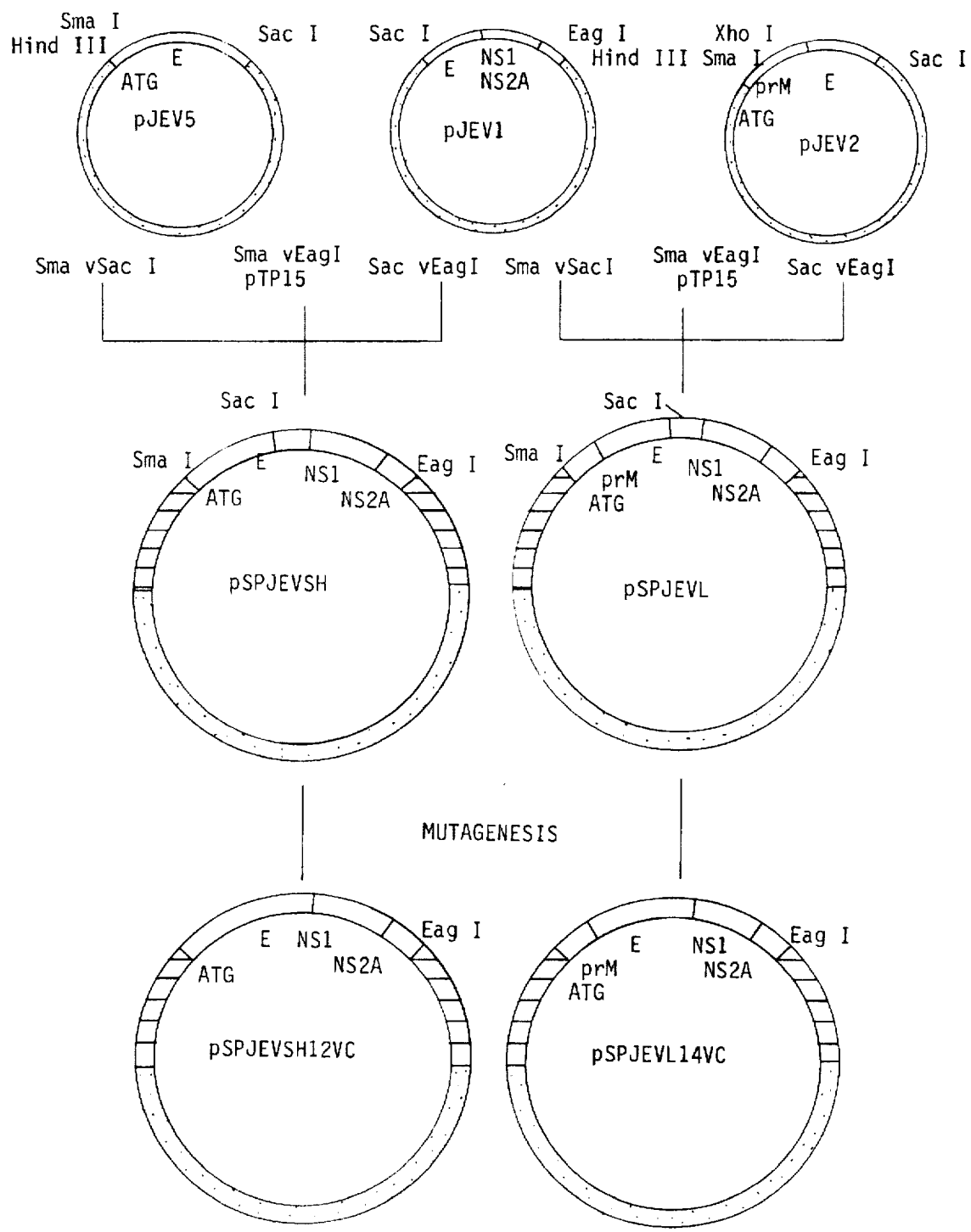
FIG. 1 schematically shows a method for the construction of donor plasmids pSPJEVSH12VC and pSPJEVL14VC containing coding sequences for a portion of the JEV structural protein coding region, NS1 and NS2A.

Plasmid pJEV3/4 was derived by cloning a BglII-ApaI fragment of JEV cDNA (nucleotides 2554-3558), an ApaI-BalI fragment (nucleotides 3559-4125), and annealed oligos J3 (SEQ ID NO:44) and J4 (SEQ ID NO:45) [FIG. 3; containing a translation stop followed by a vaccinia early transcription termination signal (TTTTTAT; Yuen et al., 1987), an EagI site, and a HindIII sticky end] into BamHI-HindIII digested pUC18. pJEV34 was digested within the JEV sequence by ECoRV (nucleotide 2672) and within pUC18 by SacI, and the fragment containing the plasmid origin and JEV CDNA sequences extending from nucleotides 2672-4125 was ligated to a SacI-EcoRV fragment of JEV cDNA (nucleotides 2125-2671). The resulting plasmid, pJEV1, contained the viral ORF extending from the SacI site (nucleotide 2125) in the last third of E through the BalI site (nucleotide 4125) two amino acid residues (aa) into the predicted N terminus of NS2B (FIG. 1).

Synthetic oligos J1B (SEQ ID NO:46) and J2B (SEQ ID NO:47) (FIG. 3; containing a XhoI sticky end, a SmaI site, the last 15 aa of C, and first 9 aa of JEV prM with a sticky HindIII end) were ligated to a HindIII-SacI fragment of JEV CDNA (nucleotides 407-2124), and XhoI-SacI digested vector pIBI24 (International Biotechnologies Inc., New Haven, CT). The resulting plasmid, pJEV2, contained the viral ORF extending between the methionine (Met) codon (nucleotides 337-339) occurring 15 aa preceding the predicted N terminus of prM and the SacI site (nucleotide 2124) found in the last third of E (FIG. 1).

Synthetic oligos J7 (SEQ ID NO:48) and J8 (SEQ ID NO:49) (FIG. 3; containing BamHI and NcoI sticky ends) were used to clone the NcoI-SacI fragment of JEV CDNA (nucleotides 1336-2124) into BamHI-SacI digested pIBI24 yielding pSPNC78. Oligonucleotides J9 (SEQ ID NO:50) and J10 (SEQ ID NO:51) (FIG. 3; containing a HindIII sticky end, a SnaI site, and nucleotides 811-832 of JEV cDNA) were used to clone a HindIII-NcoI fragment of JEV cDNA (nucleotides 833-1335) into HindIII-NcoI digested pSPNC78. The resulting plasmid, pJEV5, contained the viral ORF extending between the Met codon (nucleotides 811-813) occurring 25 aa preceding the N terminus of E and the SacI site (nucleotide 2124) found in the last third of E (FIG. 1).

pTP15 contains the early/late vaccinia virus H6 promoter inserted into a polylinker region flanked by sequences from the HindIII A fragment of vaccinia virus from which the hemagglutinin (HA) gene has been deleted (Guo et al., 1989). SmaI-EagI digested pTP15 was purified and ligated to the purified SmaI-SacI insert from pJEV2 plus the SacI-EagI insert of pJEV1, yielding pSPJEVL (FIG. 1). The 6 bp corresponding to the unique SmaI site used to produce PSPJEVL were then removed using oligonucleotide-directed double-strand break mutagenesis (Mandecki, 1986), creating pSPJEVL14VC in which the H6 promoter immediately preceded the ATG start codon (FIG. 1).

The SmaI-EagI pTP15 fragment was ligated to the purified SmaI-SacI insert from pJEV5 plus the SacI-EagI insert of pJEV1, yielding pSPJEVSH (FIG. 1). The 6 bp corresponding to the unique SmaI site used to produce pSPJEVSH were removed as described above, creating pSPJEVSH12VC in which the H6 promoter immediately preceded the ATG start codon (FIG. 1).

Oligonucleotide-directed mutagenesis (Kunkel, 1985) was used to change a potential vaccinia virus early transcription termination signal (Yuen et al., 1987) in the E gene of pJEV2 (TTTTTGT; nucleotides 1304-1310) to TCTTTGT, creating plasmid pJEV22 (FIG. 2). The same change was performed on pJEV5 producing pJEV6 (FIG. 2).

Synthetic oligos J37 and J38 [FIG. 3; containing JEV nucleotides 4497-4512, a translation stop, an early transcription termination signal (TTTTTAT; Yuen et al., 1987), an EagI site, and HindIII sticky end] were used to clone a SacI-DraI fragment of JEV cDNA (nucleotides 2125-4496) into SacI-HindIII digested pIBI24. The resulting plasmid, pJEV7, contained the viral ORF extending between the SacI site (nucleotide 2125) found in the last third of E and the last codon of NS2B (nucleotide 4512) (FIG. 2). SmaI-EagI digested pTP15 was purified and ligated to the purified SmaI-SacI insert from pJEV22 plus the SacI-EagI insert of pJEV7, yielding pSPJEV10 (FIG. 2). The 6 bp corresponding to the SmaI site used to create pSPJEV10 were removed as described above, creating pSPJEV10VC (FIG. 2). Ligation of the SmaI-EagI digested pTP15 with the SmaI-SacI insert of pJEV6 and SacI-EagI insert of pJEV7 yielded pSPJEV11 (FIG. 2). The 6 bp corresponding to the SmaI site used to create pSPJEV11 were removed as described above, yielding PSPJEV11VC (FIG. 2).

EXAMPLE 2—CONSTRUCTION OF VACCINIA VIRUS RECOMBINANTS

Figure 4:
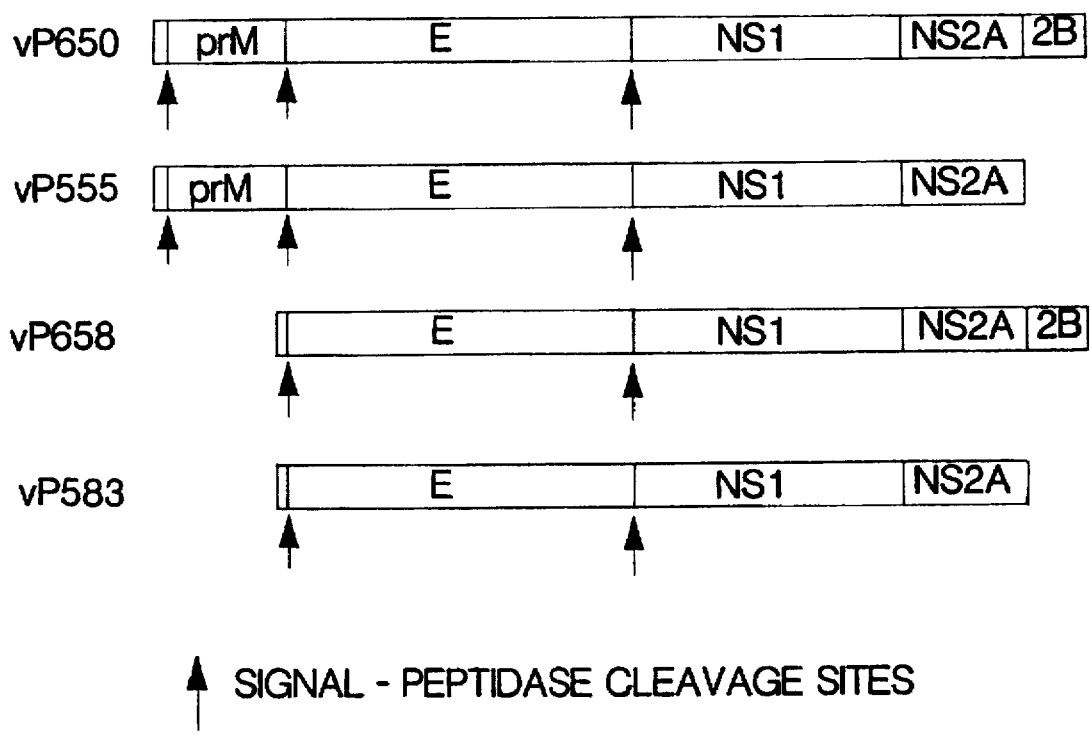
FIG. 4 is a map of the JEV coding regions inserted in the four recombinant vaccinia viruses vP650, vP555, vP658 and vP583.

Procedures for transfection of recombinant donor plasmids into tissue culture cells infected with a rescuing vaccinia virus and identification of recombinants by in situ hybridization on nitrocellulose filters have been described (Guo et al., 1989; Panicali et al., 1982). pSPJEVL14VC, pSPJEVSH12VC, and pSPJEV10VC were transfected into vP425-infected cells to generate the vaccinia recombinants vP555, vP583 and vP650, respectively (FIG. 4). pSPJEV11VC was transfected into vP410 infected cells to generate the vaccinia recombinant vP658 (FIG. 4).

EXAMPLE 3—IN VITRO VIRUS INFECTION AND RADIOLABELING

BHK or VERO cell monolayers were prepared in 35 mm diameter dishes and infected with vaccinia viruses (m.o.i. of 2) or JEV (m.o.i. of 5) and incubated for 11 hr (vaccinia) or 16 hr (JEV) before radiolabeling. At 11 hr or 16 hr post-infection, the medium was removed and replaced with warm Met-free medium containing 2% FBS and 250 µgCi/ml of $^{35}$S-Met. The cells were incubated for 1 hr at 37° C, rinsed with warm maintenance medium containing 10-times the normal amount of unlabeled Met, and incubated in this same high Met medium 6 hr before harvesting as described below. In some cases, samples of clarified culture fluid were analyzed by sucrose gradient centrifugation in 10 to 35% continuous sucrose gradients prepared, centrifuged, and analyzed as described (Mason, 1989).

EXAMPLE 4—RADIOIMMUNOPRECIPITATIONS, POLYACRYLAMIDE GEL ELECTROPHORESIS, AND ENDOGLYCOSIDASE TREATMENT

Radiolabeled cell lysates and culture fluids were harvested and the viral proteins were immunoprecipitated, digested with endoglycosidases, and separated in SDS-containing polyacrylamide gels (SDS-PAGE) exactly as described (Mason, 1989). Unless otherwise noted, all SDS-PAGE samples were prepared by heating in the presence of 50 mM dithiothreitol (DTT) before electrophoresis.

EXAMPLE 5—STRUCTURE OF RECOMBINANT VACCINIA VIRUSES

Four different vaccinia virus recombinants were constructed that expressed portions of the JEV coding region extending from prM through NS2B. The JEV cDNA sequences contained in these recombinant viruses are shown in FIG. 4. In all four recombinant viruses the sense strand of the JEV cDNA was positioned behind the vaccinia virus early/late H6 promoter, and translation was expected to be initiated from naturally occurring JEV Met codons located at the 5' ends of the viral cDNA sequences (FIG. 4).

Recombinant vP555 encodes the putative 15 aa signal sequence preceding the N terminus of the structural protein precursor prM, the structural glycoprotein E, the nonstructural glycoprotein NS1, and the nonstructural protein NS2A (McAda et al., 1987). Recombinant vP583 encodes the putative signal sequence preceding the N terminus of E, E, NS1, and NS2A (McAda et al., 1987). Recombinant vP650 contains a cDNA encoding the same proteins as vP555 with the addition of the NS2B coding region. Recombinant vP658 contains a cDNA encoding the same proteins as vP583 with the addition of NS2B. In recombinants vP650 and vP658, a potential vaccinia virus early transcription termination signal in E (TTTTTGT; nucleotides 1087–1094) was modified to TCTTTGT without altering the aa sequence. This change was made in an attempt to increase the level of expression of E and NS1, since this sequence has been shown to increase transcription termination in in vitro transcription assays (Yuen et al., 1987).

The location and orientation of the JEV genes within the recombinant vaccinia genomes were confirmed by restriction enzyme digestion of recombinant vaccinia virus DNA. During these analyses it was noted that recombinants vP555, vP583, and vP650 had a deletion from within the HindIII C fragment through HindIII N and M and into HindIII K. This same deletion was observed in the vP425 parental virus. Interestingly, these viruses were less cytopathic in VERO cells than vP410 and its derivative vP658.

NS1 was Properly Processed and Secreted when Expressed by Recombinant Vaccinia Viruses FIGS. 5 and 6 show a comparison of the NS1 proteins produced by JEV infection or infection with the recombinant vaccinia viruses. BHK cells were infected with JEV or recombinant vaccinia viruses, then labeled for 1 hr with $^{35}$S-Met, and chased for 6 hr. Equal fractions of the cell lysate (FIG. 5) or culture fluid (FIG. 6) prepared from each cell layer were immunoprecipitated, and then either mock digested (M), digested with endo H (H), or digested with PNGase F (F), prior to SDS-PAGE analysis.

The data from the pulse-chase experiments depicted in FIGS. 5 and 6 demonstrate that proteins identical in size to authentic NS1 and NS1' were synthesized in and secreted from cells infected with any of the 4 recombinant vaccinia viruses. Furthermore, the sensitivity of these proteins to endo H and PNGase F indicated that the recombinant forms of NS1 were glycosylated. Specifically, the cell-associated forms of NS1 all contained two immature (endo H sensitive) N-linked glycans, while the extracellular forms contained one immature and one complex or hybrid (endo H resistant) glycan (see Mason, 1989). Interestingly, these pulse-chase studies showed similar levels of NS1 production by all four recombinants, suggesting that the potential vaccinia early transcriptional termination signal present near the end of the E coding region in vP555 and vP583 did not significantly reduce the amount of NS1 produced relative to vP650 or vP658 in which the TTTTTGT was modified. Although the experiments depicted in FIGS. 5 and 6 were conducted on BHK cells 11 hr post-infection, similar experiments with infected VERO cells pulse-labeled at 4 or 8 hr post-infection did not reveal any differences in NS1 expression associated with the presence or absence of this TTTTTGT sequence. Comparison of the synthesis of NS1 from vaccinia viruses containing either the NS2A (vP555 and vP583) or both the NS2A and NS2B (vP650 and vP658) coding regions showed that the presence or absence of the NS2B coding region had no affect on NS1 expression. These results are consistent with the results of Falgout et al. (1989) showing that only the NS2A gene is needed for the proper processing of NS1.

E and prM were Properly Processed when Expressed by Recombinant Vaccinia Viruses FIGS. 7 and 8 show a comparison of the E protein produced by JEV infection or infection with the recombinant vaccinia viruses. BHK cells were infected with JEV or recombinant vaccinia viruses, then labeled for 1 hr with $^{35}$S-Met, and chased for 6 hr. Equal fractions of the cell lysate (FIG. 7) or culture fluid (FIG. 8) prepared from each cell layer were immunoprecipitated, and then either mock digested (M), digested with endo H (H), or digested with PNGase F (F), prior to SDS-PAGE analysis.

The data from the pulse-chase experiments depicted in FIGS. 7 and 8 demonstrate that proteins identical in size to E were synthesized in cells infected with all recombinant vaccinia viruses containing the E gene. However, the E protein was only released from cells infected with vaccinia viruses that contained the region of the viral ORF encoding prM, E, NS1, and NS2A (vP555 and vP650; see FIGS. 4, 7 and 8). Endoglycosidase sensitivity (FIGS. 7 and 8) revealed that both the intracellular and extracellular forms of the E protein synthesized by cells infected with the vaccinia recombinants were glycosylated; the cell-associated forms of E were endo H sensitive, whereas the extracellular forms were resistant to endo H digestion.

Immunoprecipitates prepared from radiolabeled vaccinia-infected cells using a MAb specific for M (and prM) revealed that prM was synthesized in cells infected with vP555 and vP650. Cells infected with either of these recombinant vaccinia viruses produced cellular forms of prM that were identical in size to the prM protein produced by JEV-infected cells, and a M protein of the correct size was detected in the culture fluid of cells infected with these two viruses.

The extracellular fluid harvested from cells infected with vP555 and vP650 contained forms of E that migrated with a peak of hemagglutinating activity in sucrose density gradients. Interestingly, this hemagglutinin migrated similarly to the slowly sedimenting peak of noninfectious hemagglutinin (SHA) (Russell et al., 1980) found in the culture fluid of JEV-infected cells (FIG. 9). Furthermore, these same fractions contained the fully processed form of M, demonstrating that vP555- and vP650-infected cells produced a particle that contained both of the structural membrane proteins of JEV. These particles probably represent empty JEV envelopes, analogous to the 22 nm hepatitis B virus particles found in the blood of humans infected with hepatitis B virus (Tiollais et al., 1985), and released from cells expressing the hepatitis B surface antigen gene (Dubois et al., 1980; Moriarty et al., 1981). The hemagglutinating properties of the supernatant fluid of cells infected with the recombinant viruses was examined, since hemagglutination activity requires particulate forms of JEV proteins that are sensitive to disruption by detergents (Eckels et al., 1975). These hemagglutination assays showed that the supernatant fluids harvested from cells infected with vP555 and vP650 contained hemagglutinating activity that was inhibited by anti-JEV antibodies and had a pH optimum identical to the JEV hemagglutinin. No hemagglutinating activity was detected in the culture fluid of cells infected with vP410, vP583, or vP658.

Recombinant Vaccinia Viruses Generate Extracellular Particles

Recombinant vaccinia virus vP555 produced E- and M-containing extracellular particles that behaved like empty viral envelopes. The ability of this recombinant virus to induce the synthesis of extracellular particles containing the JEV structural proteins provides a system to generate properly processed and folded forms of these antigens.

The recombinant viruses described herein contain portions of the JEV ORF that encode the precursor to the structural protein M, the structural protein E, and nonstructural proteins NS1, NS2A, and NS2B. The E and NS1 proteins produced by cells infected with these recombinant viruses underwent proteolytic cleavage and N-linked carbohydrate addition in a manner indistinguishable from the same proteins produced by cells infected with JEV. These data further demonstrate that the proteolytic cleavage and N-linked carbohydrate addition to E and NS1 do not require flavivirus nonstructural proteins located 3' to NS2A in the viral genome (Bray et al., 1989; Deubel et al., 1988; Falgout et al., 1989; Fan et al., 1990; Matsuura et al., 1989; Ruiz-Linares et al., 1989; Yasuda et al., 1990; Zhang et al., 1988; Zhao et al., 1987).

Interestingly, the portion of the ORF inserted in the recombinant vaccinia viruses had a significant effect on the late-stage processing of prM and E, but not on the fate of NS1. All recombinant viruses that encoded NS1 produced mature extracellular forms of this protein, consistent with previous studies showing that NS1 produced in the presence of NS2A and NS2B was properly processed and secreted from transfected cells (Fan et al., 1990). On the other hand, only two of the four recombinants that contained the E protein coding region produced extracellular forms of E. These two recombinants, vP555 and vP650, differed from the remaining recombinants in that they contained the prM coding region in addition to E, NS1, and NS2A. The findings that extracellular forms of E were produced only by viruses containing the coding regions for both E and prM and that the extracellular forms of E were associated with M suggest that the simultaneous synthesis of prM and E is a requirement for the formation of particles that are targeted for the extracellular fluid.

Example 6—ANIMAL PROTECTION STUDIES

Groups of 3-week-old outbred Swiss mice were immunized by intraperitoneal injection with $10^7$ pfu of vaccinia virus diluted in 0.1 ml of PBS. Three weeks after inoculation, selected mice were bled from the retroorbital sinus, and sera were stored at −70° C. Two to three days after bleeding, the mice were either re-inoculated with the recombinant virus or challenged by intraperitoneal injection with dilutions of suckling mouse brain infected with JEV (Beijing strain; multiple mouse passage) (Huang, 1982). Due to the variations in lethal dose observed between groups of mice and passages of the challenge virus, lethal-dose titrations were performed in each challenge experiment. Following challenge, mice were observed at daily intervals for three weeks.

Evaluation of Immune Response to the Recombinant Vaccinia Viruses

Pools of mouse sera were prepared by mixing equal aliquots of sera from the representative animals bled in each group. Three-microliter samples of pooled sera were mixed with detergent-treated cell culture fluid obtained from $^{35}$S-Met-labeled JEV-infected cells, and the antigen antibody mixtures were then incubated with fixed Staphylococcus aureus bacteria (The Enzyme Center, Malden, MA) that were coated with rabbit anti-mouse immunoglobulins (Dakopatts, Gostrup, Denmark) to assure that all classes of murine antibodies would be precipitated. The samples obtained from these precipitations were not treated with dithiothreitol prior to electrophoresis in order to avoid electrophoretic artifacts that resulted from the co-migration of the rabbit immunoglobulin heavy chain with the radiolabeled viral antigens, and to permit clear separation of the E and the NS1' proteins. Neutralization tests were performed on heat-inactivated sera (20 min. at 56° C.) as described (Tesh et al., 1987) with the following modifications: (1) freshly thawed human serum was added to all virus/antibody dilutions to a final concentration of 2.5%, (2) following virus absorption, the cell monolayers were overlayed with medium containing 0.5% carboxymethylcellulose (Sigma, St. Louis, MO), and (3) plaques were visualized at 6 days post-infection by staining with 0.1% crystal violet dissolved in 20% ethanol. Hemagglutination tests and hemagglutination- inhibition (HAI) tests were performed by a modification of the method of Clarke et al. (1958).

Vaccination with vP555 Provided Protection Against Greater than 10.000 $LD_{50}$ of JEV The recombinant vaccinia viruses were tested for their ability to protect outbred mice from lethal JEV infection using the Beijing strain of JEV, which exhibits high peripheral pathogenicity in mice (Huang, 1982). Based on preliminary experiments which showed that all four recombinant vaccinia viruses could provide some protection from a lethal challenge of this virus, two viruses (vP555 and vP658) were selected for in-depth challenge studies. vP555 induced the synthesis of extracellular forms of E, whereas vP658 did not produce any extracellular forms of E, but contained additional cDNA sequences encoding the NS2B protein. In the challenge experiments several dilutions of challenge virus were tested, the effect of a booster immunization with vaccinia recombinants on the levels of protection was examined, and the serological responses in a subset of the vaccinated animals were evaluated. The results of a single inoculation with these recombinant viruses showed that recombinant virus vP555 produced better levels of protection than vP658 at all challenge doses (Table 1). Both recombinant viruses provided better protection at lower levels of challenge virus, consistent with the ability to overwhelm protection with high doses of JEV. Table 1 also shows that complete protection from more than 10,000 $LD_{50}$ of JEV was achieved by two inoculations with vP555, which was not the case for vP658 at the challenge doses tested. FIG. 10 shows an analysis of the JEV-specific reactivity of pre-challenge sera from animals vaccinated with the recombinant vaccinia viruses. Sera collected from a subset of the animals used in the protection experiments (see Tables 1 and 2) were pooled and aliquots were tested for their ability to immunoprecipitate radiolabeled proteins harvested from the culture fluid of JEV-infected cells. The two lanes on the right side of the autoradiogram of FIG. 10 were prepared from samples immunoprecipitated with sera obtained from uninoculated mice (–) or from a mouse that survived a normally lethal dose of JEV. The analysis demonstrated that: (1) only those animals immunized with vP555 showed a strong immune response to E, and (2) a second inoculation resulted in a significant increase in reactivity to the E protein (FIG. 10).

Analysis of the neutralization and HAI data for the sera collected from these animals confirmed the results of the immunoprecipitation analyses, showing that the animals boosted with vP555, which were 100% protected, had very high levels of neutralizing and hemagglutination-inhibiting antibodies (Table 2). These levels of neutralizing and hemagglutination-inhibiting antibodies were similar to the titers achieved in naive mice that survived challenge from a normally lethal dose of the Beijing strain of JEV.

The ability of vP555 to induce neutralizing antibodies may be related to the fact that vP555 produces an extracellular particulate form of the structural proteins E and M. This SHA-like particle probably represents an empty JEV envelope that contains E and M folded and assembled into a configuration very similar to that found in the infectious JEV particle. Recombinants vP555 and vP650 may generate extracellular forms of the structural proteins because they contain the coding regions for all three JEV glycoproteins, thereby providing all of the JEV gene products needed for assembly of viral envelopes. Other investigators (see above) have not been able to detect the production of extracellular forms of E by cells expressing all three structural proteins (C, prM, and E) in the presence or absence of NS1 and NS2A. The inability of their recombinant viruses to produce particles similar to those produced by vP555 and vP650 could be due to the presence of the C protein gene in their recombinant genomes. In particular, it is possible that the C protein produced in the absence of a genomic RNA interferes with the proper assembly of the viral membrane proteins. Alternatively, an incompletely processed form of C similar to that detected by Nowak et al. (1989) in in vitro translation experiments, could prevent release of the structural membrane proteins from the cells expressing the C gene.

TABLE 1

Evaluation of ability of recombinant vaccinia virus vP555 or vP658 to protect mice from fatal JEV encephalitis

| IMMUNIZING VIRUS[1] | CHALLENGE DOSE (LOG)[2] | SURVIVAL AFTER ONE INOCULATION[3] | SURVIVAL AFTER TWO INOCULATIONS[4] |
|---|---|---|---|
| vP410 | −1 | 0/20 | 0/10 |
| vP410 | −2 | 0/20 | 1/10 |
| vP410 | −3 | 0/18 | |
| vP555 | −1 | 12/20 | 10/10 |
| vP555 | −2 | 15/20 | 10/10 |
| vP555 | −3 | 18/19 | |
| vP658 | −1 | 0/20 | 3/9 |
| vP658 | −2 | 4/22 | 3/10 |
| vP658 | −3 | 12/18 | |
| – | −2 | 0/5 | 1/5 |
| – | −3 | 1/10 | 3/5 |
| – | −4 | 2/10 | 4/10 |
| – | −5 | 3/10 | 6/10 |
| – | −6 | 4/10 | 3/10 |
| – | −7 | 3/5 | 7/10 |
| – | −8 | | 5/6 |

[1]Vaccinia recombinant used for immunization, or unimmunized lethal dose titration groups (–).
[2]Dilution of suckling mouse brain stock delivered in the challenge. Based on the simultaneous titration data shown in this table, the challenge dose of −1 log of virus was equivalent to 4.7 × 10⁴ $LD_{50}$ for the 6-week-old animals challenged following one inoculation, and 3.0 × 10⁴ $LD_{50}$ for the 10-week-old animals challenged following two inoculations.
[3]Live animals/total for each group; challenge delivered to 6-week-old mice, three weeks following a single inoculation.
[4]Live animals/total for each group; challenge delivered to 10-week-old mice, 6 weeks following the first vaccinia inoculation and 3 weeks following a second inoculation with the same vaccinia recombinant.

TABLE 2

Plaque reduction neutralization titers and HAI antibody titers in pre-challenge sera.

| GROUP[1] | ONE INOCULATION | | TWO INOCULATIONS | |
|---|---|---|---|---|
| | NEUTRALIZATION[2] TITER | HAI[3] TITER | NEUTRALIZATION[2] TITER | HAI[3] TITER |
| vP410 GROUP 1 | <1:10 | <1:10 | | |
| vP555 GROUP 1 | 1:40 | 1:40 | | |
| vP555 GROUP 2 | 1:80 | 1:160 | 1:640 | 1:160 |
| vP658 GROUP 1 | <1:10 | <1:10 | | |
| vP658 GROUP 2 | <1:10 | <1:10 | <1:10 | <1:10 |

[1]Vaccinia recombinant used for immunization. Group 1 indicates animals challenged 3 weeks following a single vaccinia inoculation, and group 2 indicates animals challenged following two inoculations.
[2]Serum dilution yielding 90% reduction in plaque number.
[3]Serum dilution.

EXAMPLE 7—ATTENUATED VACCINIA VACCINE STRAIN NYVAC

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions sequentially deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R +B14R) vP553;

(3) A type inclusion body region (ATI; A26L) vP618;

(4) hemagglutinin gene (HA; A56R) vP723;

(5) host range gene region (C7L - K1L) vP804; and (6) large subunit, ribonucleotide reductase (I4L) vP866 (NYVAC).

DNA Cloning and Synthesis

Plasmids were constructed, screened and grown by standard procedures (Maniatis et al., 1986; Perkus et al., 1985; Piccini et al., 1987). Restriction endonucleases were obtained from GIBCO/BRL, Gaithersburg, MD, New England Biolabs, Beverly, MA; and Boehringer Mannheim Biochemicals, Indianapolis, IN. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, CT) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection

The origins and conditions of cultivation of the Copenhagen strain of vaccinia virus has been previously described (Guo et al., 1989). Generation of recombinant virus by recombination, in situ hybridization of nitrocellulose filters and screening for Beta-galactosidase activity are as previously described (Panicali et: al., 1982; Perkus et al., 1989). Construction of Plasmid pSD460 for Deletion of Thymidine Kinase Gene (J2R)

Figure 11:
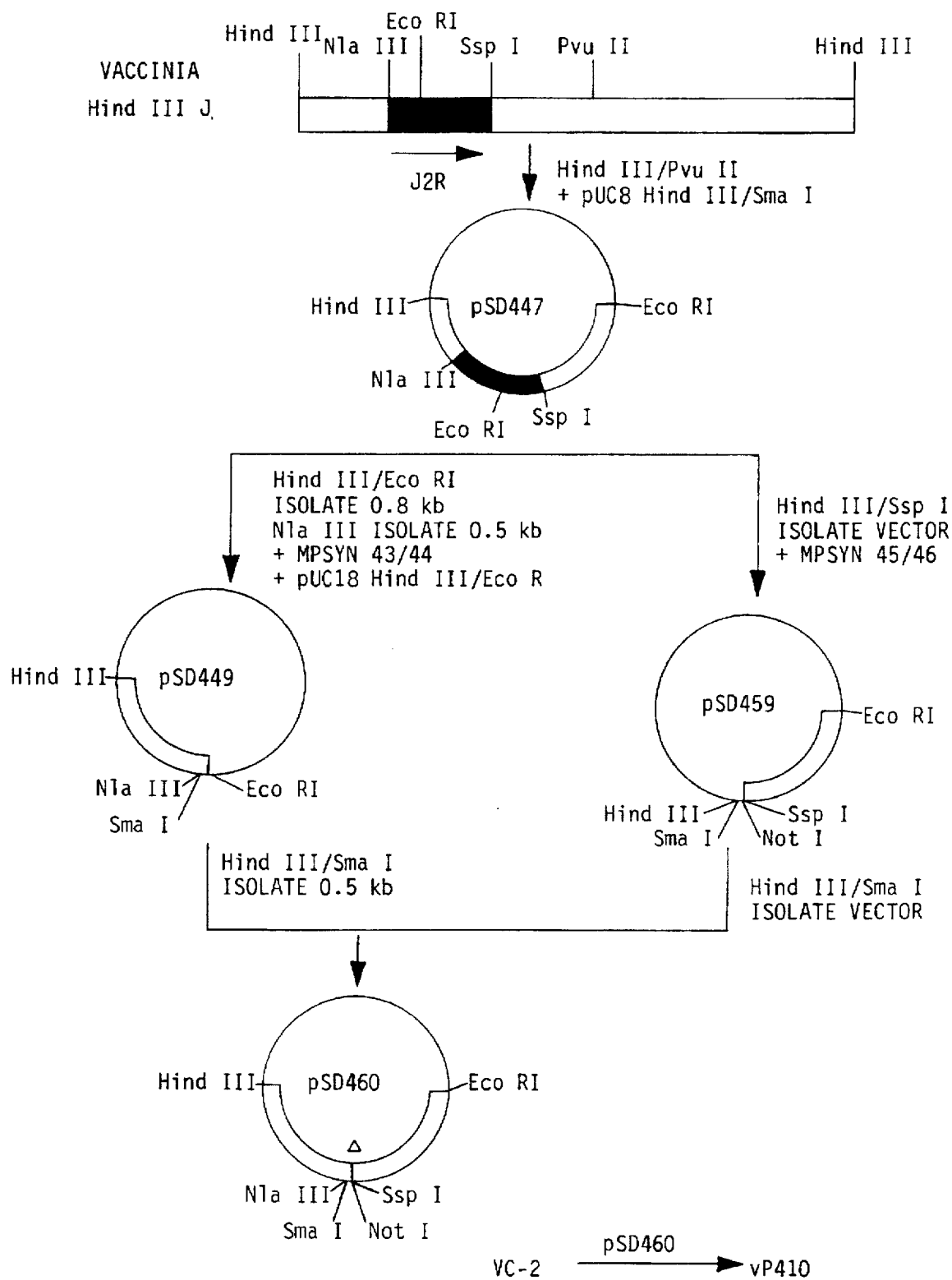
FIG. 11 schematically shows a method for the construction of plasmid pSD460 for deletion of thymidine kinase gene and generation of recombinant vaccinia virus vP410.

Referring now to FIG. 11, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 11.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
         HindIII   SmaI
MPSYN45  5' AGCTTCCCGGGTAAGTAATACGTCAAGGAGAAAACGAA
MPSYN46  3'     AGGGCCCATTCATTATGCAGTTCCTCTTTTGCTT NotI              SspI
         ACGATCTGTAGTTAGCGGCCGCCTAATTAACTAAT  3' MPSYN45
         TGCTAGACATCAATCGCCGGCGGATTAATTGATTA  5' MPSYN46
``` generating pSD459.

To combine the left and right flanking arms into one plasmid, a 0.5 kb HinddIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$p labeled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
                   ClaI          SacI         XhoI           HpaI
         SD42mer 5' CGATTACTAGTACTGAGCTCCCCGGGCTCGAGGGATCCGTT 3'
         SD40mer 3' TAATGATCTAGACTCGAGGGGCCCGAGCTCCCTAGGCAA   5'
                        BglII       SmaI           BamHI
```

Construction of Plasmid PSD486 for Deletion of Hemorrhagic Region (B13R+B14R)

Figure 12:
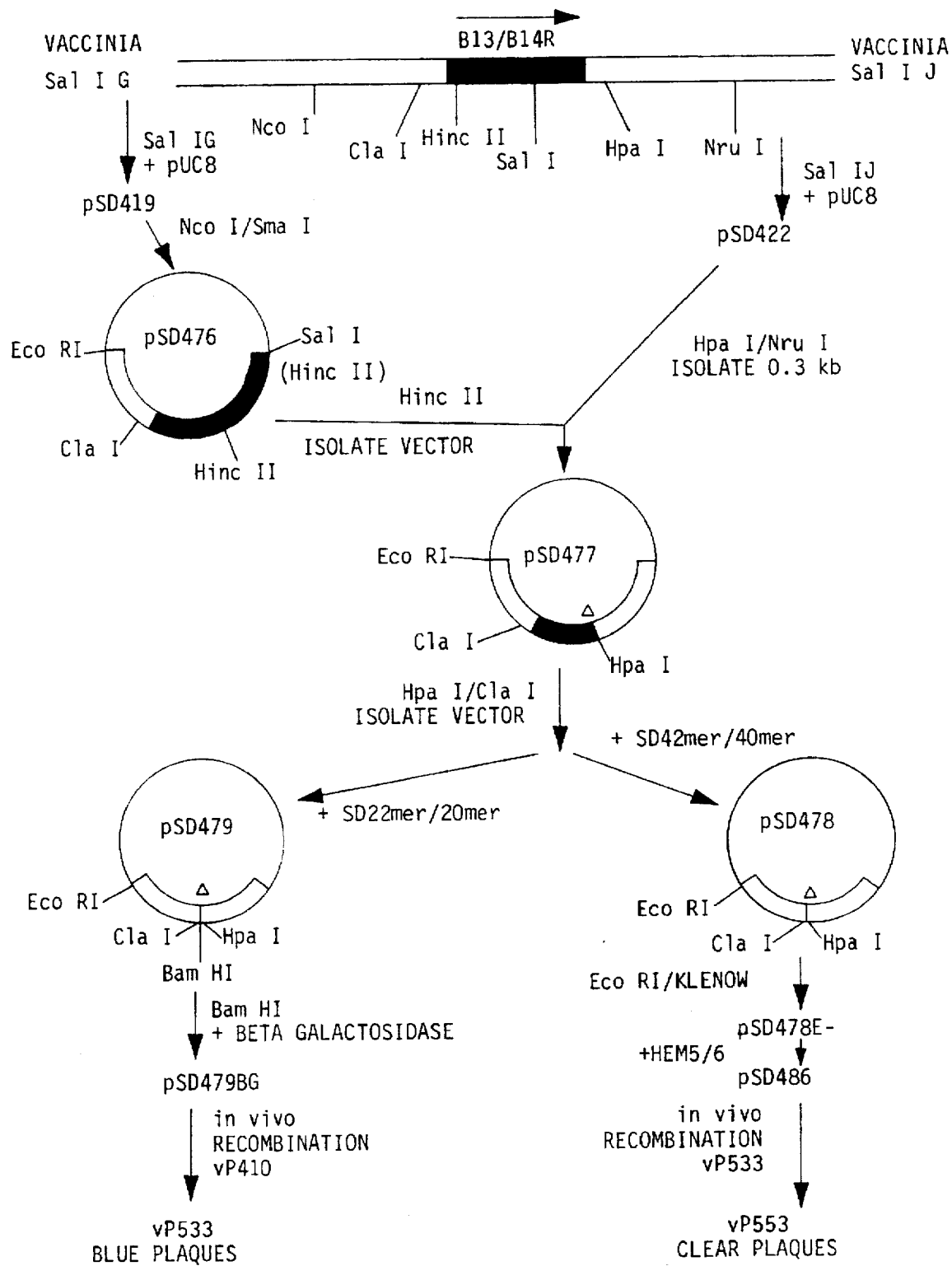
FIG. 12 schematically shows a method for the construction of plasmid pSD486 for deletion of hemorrhagic region and generation of recombinant vaccinia virus vP553.

Referring now to FIG. 12, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 12.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HindIII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

```
                   ClaI         BamHI HpaI
         SD22mer 5' CGATTACTATGAAGGATCCGTT 3'
         SD20mer 3' TAATGATACTTCCTAGGCAA   5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983)

generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO:11)

```
                BamHI EcoRI  HpaI
         HEM5 5' GATCCGAATTCTAGCT 3'
         HEM6 3'     GCTTAAGATCGA 5'
``` generating plasmid pSD486. pSD486 was used as donor plasmid for recombination with recombinant vaccinia virus vP533, generating vP553, which was isolated as a clear plaque in the presence of X-gal.

Construction of Plasmid pMP494A for Deletion of ATI Region (A26L)

Figure 13:
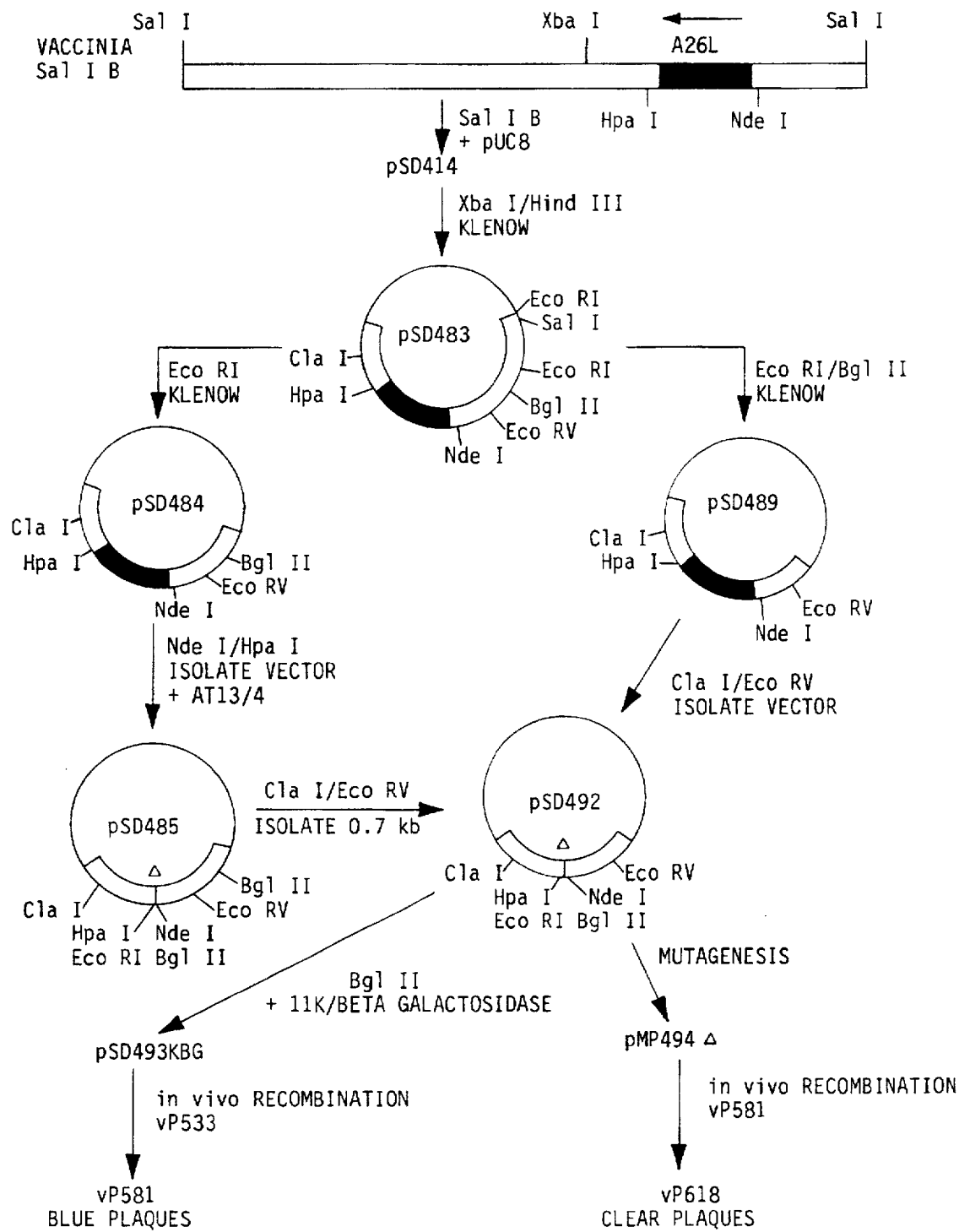
FIG. 13 schematically shows a method for the construction of plasmid pMP494A for deletion of ATI region and generation of recombinant vaccinia virus vP618.

Referring now to FIG. 13, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
          NdeI
ATI3  5'  TATGAGTAACTTAACTCTTTTGTTAATTAAAAGTATATTCAAAAAATAAGT
ATI4  3'  ACTCATTGAATTGAGAAAACAATTAATTTTCATATAAGTTTTTTATTCA

BglII    ECoRI  HpaI
          TATATAAATAGATCTGAATTCGTT   3'  ATI3
          ATATATTTATCTAGACTTAAGCAA   5'  ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSY62 (SEQ ID NO:16), MPSYN60 (SEQ ID NO:17), and MPSYN 61 (SEQ ID NO:18)

```
                    RsaI
MPSYN59  5'  ACACGAATGATTTTCTAAAGTATTTGGAAAGTTTTATAGGTAGTTGATAGAACAAAATACATAATTT   3'
MPSYN62  3'  TGTGCTTACTAAAAGATTTCATAAACCTTTCAAAATATCCATCAACTATCT                        5'

BglII  SmaI  PstI  EagI
MPSYN60  5'          TGTAAAAATAAATCACTTTTTATACTAAGATCTCCCGGGCTGCAGC              3'
MPSYN61  3'  TGTTTTATGTATTAAAACATTTTTATTTAGTGAAAAATATGATTCTAGAGGGCCCGACGTCGCCGG  5'
```

ORF was replaced with the corresponding 0.7 kb polylinker-containing ClaI/EcoRV fragment from pSD485, generating pSD492. The BglII and EcORI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494A and the Beta-galactosidase containing vaccinia recombinant, vP581, resulted in vaccinia deletion mutant vP618, which was isolated as a clear plaque in the presence of X-gal.

Construction of Plasmid pSD467 for Deletion of Hemagglutinin Gene (A56R)

Figure 14:
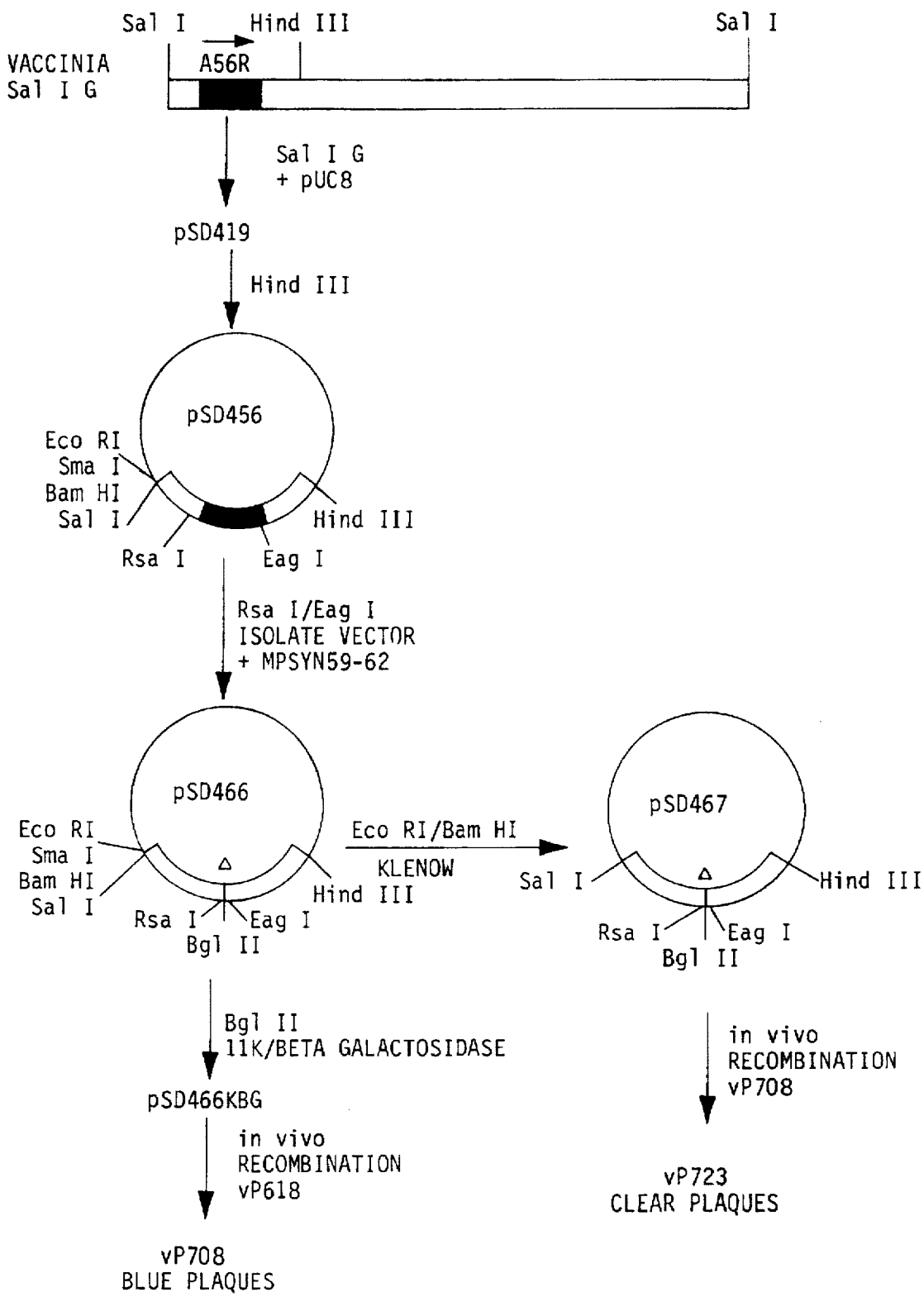
FIG. 14 schematically shows a method for the construction of plasmid pSD467 for deletion of hemagglutinin gene and generation of recombinant vaccinia virus vP723.

Referring now to FIG. 14, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 14. Vaccinia sequences derived from HindIII B were removed by digestion of pSD419 with HindIII within vaccinia sequences and at the pUC/vaccinia junction followed by ligation. The resulting plasmid, pSD456, contains the HA reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 14.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant: vaccinia deletion mutant, vP723, which was isolated as a clear plaque in the presence of X-gal.

Construction of Plasmid pMPCSK1Δ for Deletion of Open Reading Frames [C7L-K1L]

Figure 15:
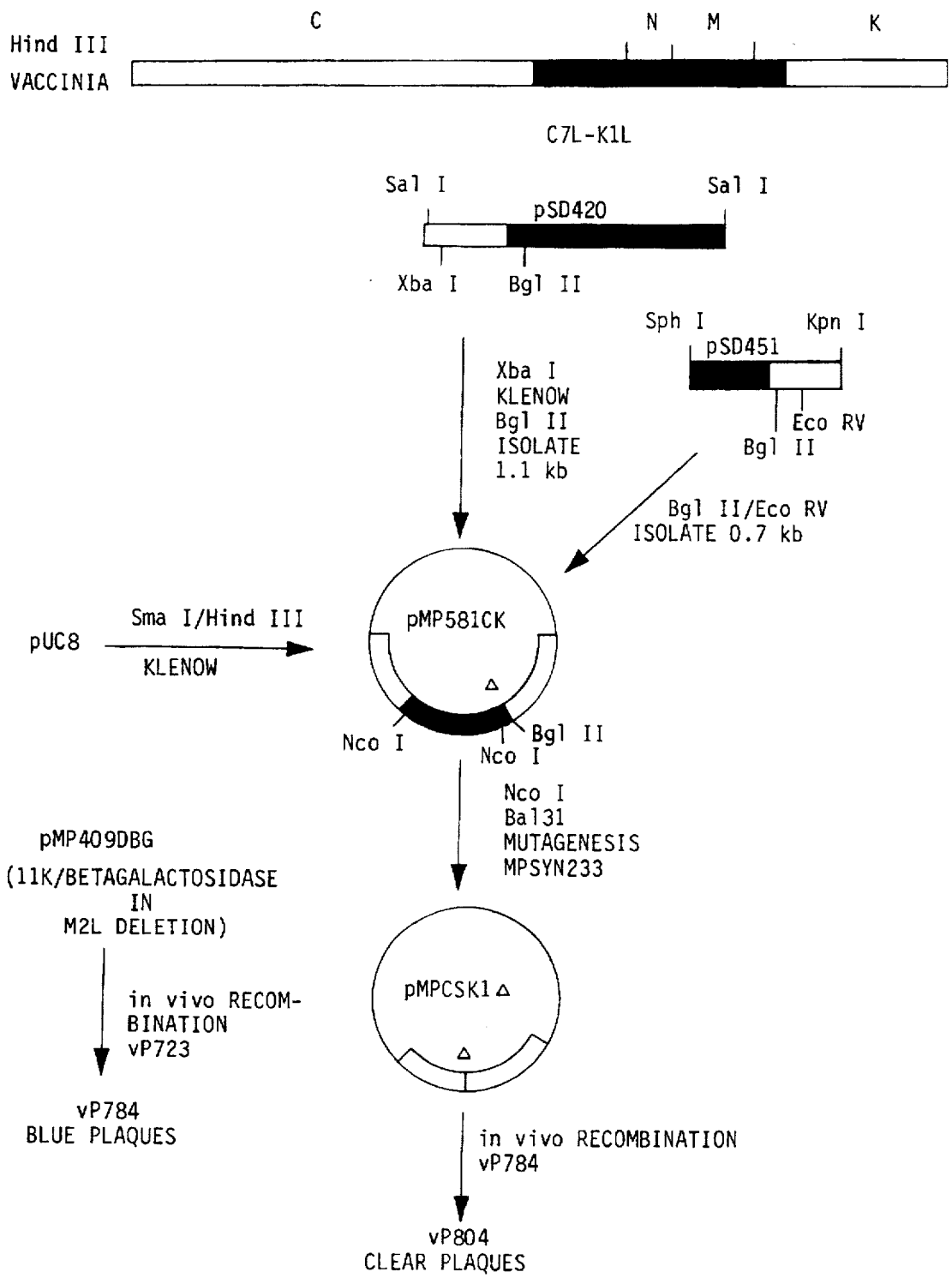
FIG. 15 schematically shows a method for the construction of plasmid pMPCSK1A for deletion of gene cluster [C7L - K1L] and generation of recombinant vaccinia virus vP804.

Referring now to FIG. 15, the following vaccinia clones were utilized in the construction of pMPCSK1A. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

Figure 16:
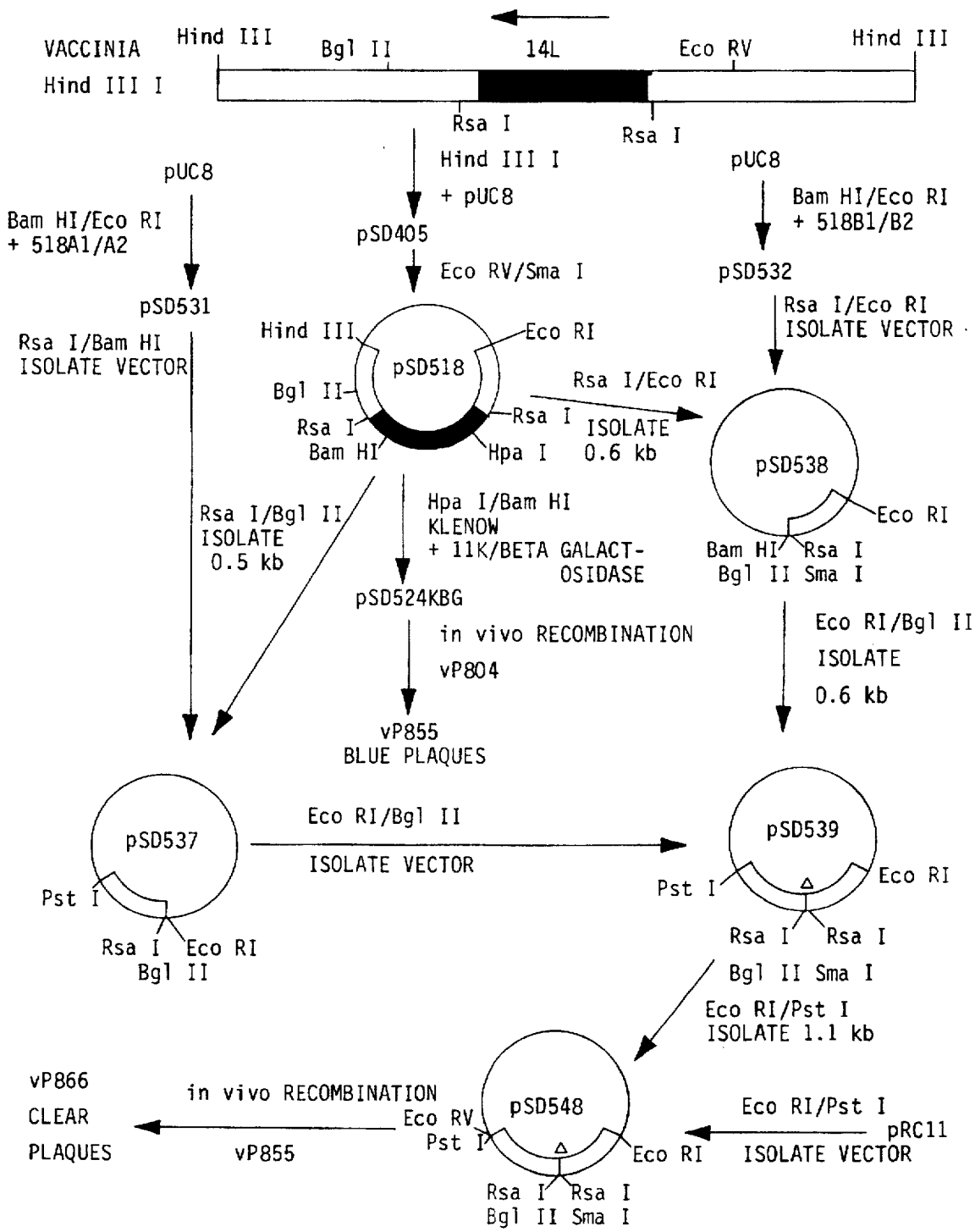
FIG. 16 schematically shows a method for the construction of plasmid pSD548 for deletion of large subunit, ribonucleotide reductase and generation of recombinant vaccinia virus vP866 (NYVAC)

To provide a substrate for the deletion of the [C7L-K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide Referring now to FIG. 16, plasmid pSD405 contains vaccinia HindIII I (pos. 63,875–70,367) cloned in pUC8. pSD405 was digested with EcoRV within vaccinia sequences (pos. 67,933) and with SmaI at the puc/vaccinia junction, and ligated, forming plasmid pSD518. pSD518

```
                                    BglII
MPSYN82 (SEQ ID NO:19) 5' TTTCTGTATATTTGCACCAATTTAGATCTTACTCAAAA
                         TATGTAACAATA 3'
```

The resulting plasmid, pMP409D, contains a unique BglII site inserted into the M2L deletion locus as indicated above. A 3.2 kb BamHI (partial)/BglII cassette containing the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L-K1L] was assembled in PUC8 cut with SmaI, HindIII and blunt ended with Klenow fragment of *E. coli* polymerase. The left flanking arm consisting of vaccinia HindIII C sequences was obtained by digestion of pSD420 with XbaI (pos. 18,628) followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 15.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID was used as the source of all the vaccinia restriction fragments used in the construction of pSD548.

The vaccinia I4L gene extends from position 67,371–65,059. Direction of transcription for I4L is indicated by an arrow in FIG. 16. To obtain a vector plasmid fragment deleted for a portion of the I4L coding sequences, pSD518 was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 16.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
         BamHI     RsaI
518A1 5' GATCCTGAGTACTTTGTAATATAATGATATATATTTTCACTTTATCTCAT
518A2 3'     GACTCATGAAACATTATATTACTATATATAAAAGTGAAATAGAGTA

BglII       EcoRI
         TTGAGAATAAAAAGATCTTAGG          3' 518A1
         AACTCTTATTTTTCTAGAATCCTTAA      5' 518A2
```

NO:20) 5' TGTCATTTAACACTATACTCATAT-TAATAAAAATAATATTTATT 3'. The resulting plasmid, pMPCSK1A, is deleted for vaccinia sequences positions 18,805–29,108, encompassing 12 vaccinia open reading frames [C7L - K1L]. Recombination between pMPCSK1A and the Beta-galactosidase containing vaccinia recombinant, vP784, resulted in vaccinia deletion mutant, vP804, which was isolated as a clear plaque in the presence of X-gal.
Construction of Plasmid pSD548 for Deletion of Large Subunit, Ribonucleotide Reductase (I4L)

forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
         BamHI  BglII  SmaI
518B1 5' GATCCAGATCTCCCGGGAAAAAAATTATTTAACTTTTCATTAATAGGGATTT
518B2 3'         GTCTAGAGGGCCCTTTTTTTAATAAATTGAAAAGTAATTATCCCTAAA

RsaI    EcoRI
     GACGTATGTAGCGTACTAGG         3'  518B1
     CTGCATACTACGCATGATCCTTAA     5'  518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 16. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

EXAMPLE 8—CONSTRUCTION OF NYVAC-MV RECOMBINANT EXPRESSING MEASLES FUSION AND HEMAGGLUTININ GLYCOPROTEINS cDNA copies of the sequences encoding the HA and F proteins of measles virus MV (Edmonston strain) were inserted into NYVAC to create a double recombinant designated NYVAC-MV. The recombinant authentically expressed both measles glycoproteins on the surface of infected cells. Immunoprecipitation analysis demonstrated correct processing of both F and HA glycoproteins. The recombinant was also shown to induce syncytia formation.
Cells and Viruses The rescuing virus used in the production of NYVAC-MV was the modified Copenhagen strain of vaccinia virus designated NYVAC. All viruses were grown and titered on Vero cell monolayers.
Plasmid Construction Plasmid pSPM2LHA (Taylor et al., 1991) contains the entire measles HA gene linked in a precise ATG to ATG configuration with the vaccinia virus H6 promoter which has been previously described (Taylor et al., 1988a,b; Guo et al., 1989; Perkus et al., 1989). A 1.8 kpb EcoRV/SmaI fragment containing the 3' most 24 bp of the H6 promoter fused in a precise ATG:ATG configuration with the HA gene lacking the 3' most 26 bp was isolated from pSPM2LHA. This fragment was used to replace the 1.8 kbp EcoRV/SmaI fragment of pSPMHHA11 (Taylor et al., 1991) to generate pRW803. Plasmid pRW803 contains the entire H6 promoter linked precisely to the entire measles HA gene.

In the confirmation of previous constructs with the measles HA gene it was noted that the sequence for codon 18(CCC) was deleted as compared to the published sequence (Alkhatib et al., 1986). The CCC sequence was replaced by oligonucleotide mutagenesis via the Kunkel method (Kunkel, 1985) using oligonucleotide RW117 (SEQ ID NO:39) (5' GACTATCCTACTTCCCTTGG-GATGGGGGTTATCTTTG TA-3').

PRO 18

Single stranded template was derived from plasmid pRW819 which contains the H6/HA cassette from pRWSO3 in pIBI25 (International Biotechnologies, Inc., New Haven, CT). The mutagenized plasmid containing the inserted (CCC) to encode for a proline residue at codon 18 was designated pRW820. The sequence between the HindIII and XbaI sites of pRW820 was confirmed by nucleotide sequence analysis. The HindIII site is situated at the 5' border of the H6 promoter while the XbaI site is located 230 bp downstream from the initiation codon of the HA gene. A 1.6 kbp XbaI/EcoRI fragment from pRW803, containing the HA coding sequences downstream from the XbaI (above) and including the termination codon, was used to replace the equivalent fragment of pRW820 resulting in the generation of pRW837. The mutagenized expression cassette contained within pRW837 was derived by digestion with HindIII and EcoRI, blunt-ended using the Klenow fragment of E. coli DNA polymerase in the presence of 2mM dNTPs, and inserted into the SmaI site of pSD513 to yield pRW843. Plasmid pSD513 was derived from plasmid pSD460 by the addition of polylinker sequences. Plasmid pSD460 was derived to enable deletion of the thymidine kinase gene from vaccinia virus (FIG. 11).

To insert the measles virus F gene into the HA insertion plasmid, manipulations were performed on pSPHMF7. Plasmid pSPHMF7 (Taylor et al., 1991) contains the measles F gene juxtaposed 3' to the previously described vaccinia virus H6 promoter. In order to attain a perfect ATG for ATG configuration and remove intervening sequences between the 3' end of the promoter and the ATG of the measles F gene oligonucleotide directed mutagenesis was performed using oligonucleotide SPMAD (SEQ ID NO:40). SPMAD: 5'-TATCCGTTAAGTTTGTATCGTAATGGGTCTCAAGGT GAACGTCT-3' The resultant plasmid was designated pSPMF75M20.

The plasmid pSPMF75M20 which contains the measles F gene now linked in a precise ATG for ATG configuration with the H6 promoter was digested with NruI and EagI. The resulting 1.7 kbp blunt ended fragment containing the 3' most 27 bp of the H6 promoter and the entire fusion gene was isolated and inserted into an intermediate plasmid pRW823 which had been digested with NruI and XbaI and blunt ended. The resultant plasmid pRW841 contains the H6 promoter linked to the measles F gene in the pIBI25 plasmid vector (International Biotechnologies, Inc., New Haven, CT). The H6/measles F cassette was excised from pRW841 by digestion with SmaI and the resulting 1.8 kb fragment was inserted into pRW843 (containing the measles HA gene). Plasmid pRW843 was first digested with NotI and blunt-ended with Klenow fragment of E. coli DNA polymerase in the presence of 2mM dNTPs. The resulting plasmid, pRW857, therefore contains the measles virus F and HA genes linked in a tail to tail configuration. Both genes are linked to the vaccinia virus H6 promoter.

Development of NYVAC-MV

Plasmid pRW857 was transfected into NYVAC infected Vero cells by using the calcium phosphate precipitation method previously described (Panicali et al., 1982; Piccini et al., 1987). Positive plaques were selected on the basis of in situ plaque hybridization to specific MV F and HA radiolabeled probes and subjected to 6 sequential rounds of plaque purification until a pure population was achieved. One representative plaque was then amplified and the resulting recombinant was designated NYVAC-MV (vP913).

EXAMPLE 9—CLONING OF JEV GENES INTO A VACCINIA VIRUS DONOR PLASMID

A thymidine kinase mutant of the Copenhagen strain of vaccinia virus vP410 (Guo et al., 1989) was used to generate recombinants vP825, vP829, vP857 and vP864 (see below). The generation of vP555 has previously been described (Mason et al., 1991). All vaccinia virus stocks were produced in VERO (ATCC CCL81) cells in Eagle's minimal essential medium plus 10% heat inactivated fetal bovine serum (FBS). Biosynthetic studies were performed using VERO Cells grown at 37° C. in MEM supplemented with 5% FBS and antibiotics, or HeLa (ATCC CCL2) cells grown under the same conditions except using 10% FBS and non-essential amino acids. The JEV virus used in all in vitro experiments was a clarified culture fluid prepared from C6/36 cells infected with a passage 55 suckling mouse brain suspension of the Nakayama strain of JEV (Mason, 1989). Animal challenge experiments were performed using the highly pathogenic P3 strain of JEV (multiple mouse passage; Huang, 1982).

cDNA encoding the C protein of JEV was obtained by a modification of the method of Okayama and Berg (1982) using Moloney murine leukemia virus reverse transcriptase (GIBCO/BRL, Gaithersburg, MD) (D'Alessio and Gerrard, 1988). Genomic RNA was isolated from virions prepared by the method of Repik et al. (1983) from suspension cultures of C6/36 cells infected with a passage 55 suckling mouse brain stock of the Nakayama strain of JEV. First strand cDNA synthesis was primed from a synthetic oligonucleotide complementary to bases 986 to 1005 of the E coding region of JEV (FIG. 17A and B) (SEQ ID NO:52). The double-stranded cDNA was ligated to synthetic oligonucleotides containing the EcoRI site (New England Biolabs, Beverly, MA), inserted into phosphatase treated EcoRI-cleaved pBR322 (New England Biolabs), and the resulting DNA was used to transform E. coli strain DH5 cells (GIBCO/BRL). Plasmids were analyzed by restriction enzyme digestion and a plasmid (pC20) containing cDNA corresponding to 81 nucleotides of non-coding RNA and the C and prM coding regions was identified. pC20 was digested at the linker sites with EcoRI and at an internal DraI site situated 28 bp 5' of the ATG initiation codon and the resulting fragment containing the C and prM coding regions was inserted into SmaI-EcoRI digested pUC18, creating plasmid, pDr20. The sequence of the C coding region of pC20, combined with an updated sequence of the prM, E, NS1, NS2A, and NS2B coding regions of the Nakayama strain of JEV is presented in FIG. 17A and B (SEQ ID NO:52). All nucleotide coordinates are based on this updated sequence with numbering beginning at the C protein Met initiation codon.

Plasmid pDr20 containing JEV cDNA (nucleotides −28 to 1000) in the SmaI and EcoRI sites of pUC18 (see above) was digested with BamHI and EcoRI and the JEV cDNA insert cloned into pIBI25 (International Biotechnologies, Inc., New Haven, CT) generating plasmid JEV18. JEV18 was digested with ApaI within the JE sequence (nucleotide 24) and XhoI within pIBI25 and ligated to annealed oligonucleotides J90 (SEQ ID NO:54) and J91 (SEQ ID NO:55) (containing an XhoI sticky end, SmaI site, and JE nucleotides 1 to 23) generating plasmid JEV19. JEV19 was digested with XhoI within pIBI25 and AccI within JE sequences (nucleotide 602) and the resulting 613 bp fragment was cloned into the XhoI and AccI fragment of JEV2 (FIG. 1) containing the plasmid origin and JEV cDNA encoding the carboxy-terminal 40% prM and amino-terminal two thirds of E (nucleotides 603 to 2124), generating plasmid JEV20 containing JE sequences from the ATG of C through the SacI site (nucleotide 2124) found in the last third of E.

The SmaI-SacI fragment from JEV8 (a plasmid analogous to JEVL (FIG. 1) in which TTTTTGT nucleotides 1304 to 1310 were changed to TCTTTGT), containing JE sequences from the last third of E through the first two amino acids of NS2B (nucleotides 2124 to 4126), the plasmid origin and vaccinia sequences, was ligated to the purified SmaI-SacI insert from JEV20 yielding JEV22-1. The 6 bp corresponding to the unique SmaI site used to construct JEV22-1 were removed using oligonucleotide-directed double-strand break mutagenesis (Mandecki, 1986) creating JEV24 in which the H6 promoter immediately preceded the ATG start codon.

Plasmid JEV7 (FIG. 2) was digested with SphI within JE sequences (nucleotide 2381) and HindIII within IBI24. Ligation to annealed oligonucleotides J94 and J95 [containing a SphI sticky end, translation stop, a vaccinia early transcription termination signal (TTTTTAT; Yuen et al., 1987) a translation stop, an EagI site and a HindIII sticky end] generated plasmid JEV25 which contains JE cDNA extending from the SacI site (nucleotide 2124) in the last third of E through the carboxy-terminus of E. The SacI-EagI fragment from JEV25 was ligated to the SacI-EagI fragment of JEV8 (containing JE cDNA encoding 15 aa C, prM and amino-terminal two thirds of E nucleotides 337 to 2124, the plasmid origin and vaccinia sequences) yielding plasmid JEV26. A unique SmaI site preceding the ATG start codon was removed as described above, creating JEV27 in which the H6 promoter immediately preceded the ATG start codon.

Oligonucleotides J96, J97, J98 and J99 (containing JE nucleotides 2293 to 2380 with an SphI sticky end) were kinased, annealed and ligated to SmaI-SphI digested and alkaline phosphatase treated pIBI25 generating plasmid JEV28. JEV28 was digested with HpaI within the JE sequence (nucleotide 2301) and with HindIII within the pIBI25 sequence and alkaline phosphatase treated. Ligation to the HpaI-HindIII fragment from JEV1 or HpaI-HindIII fragment from JEV7 (FIG. 2) yielded JEV29 [containing a SmaI site followed by JE cDNA encoding 30 aa E, NS1, NS2A (nucleotides 2293 to 4125)] and JEV30 [containing a SmaI site followed by JE cDNA encoding 30 aa E, NS1, NS2A, NS2B (nucleotides 2293 to 4512)].

The SmaI-EagI fragment from JEV29 was ligated to SmaI-EagI digested pTP15 (Mason et al., 1991) yielding JEV31. The 6 bp corresponding to the unique SmaI site used to produce JEV31 were removed as described above creating JEV33 in which the H6 promoter immediately preceded the ATG start codon.

The SmaI-EagI fragment from JEV30 was ligated to SmaI-EagI digested pTP15 yielding JEV32. The 6 bp corresponding to the unique SmaI site used to produce JEV32 were removed as described above creating JEV34 in which the H6 promoter immediately preceded the ATG start codon. Oligonucleotides J90 (SEQ ID NO:25), J91 (SEQ ID NO:26), J94 (SEQ ID NO:27), J95 (SEQ ID NO:28), J96 and J97 (SEQ ID NO:29), and J99 and J98 (SEQ ID NO:30) are as follows:

old mice were immunized by intraperitoneal (ip) injection with $10^7$ pfu of vaccinia virus, and 3 weeks later sera were collected from selected mice. Mice were then either re-inoculated with the recombinant virus or challenged by ip injection with a suspension of suckling mouse brain infected with the P3 strain of JEV. Three weeks later, the boosted animals were re-bled and challenged with the P3 strain of JEV. Following challenge, mice were observed at daily intervals for three weeks and lethal-dose titrations were performed in each challenge experiment using litter-mates of the experimental animals. In addition, sera were collected from all surviving animals 4 weeks after challenge.

Evaluation of Immune Response to the Recombinant Vaccinia Viruses

Sera were tested for their ability to precipitate JEV proteins from detergent-treated cell lysates or culture fluids obtained from $^{35}$S-Met-labeled JEV-infected cells exactly as described by Mason et al. (1991). Hemagglutination inhibition (HAI) and neutralization (NEUT) tests were performed as described by Mason et al. (1991) except 1% carboxymethylcellulose was used in the overlay medium and 5 day incubation was used for visualization of plaques for the NEUT test.

```
J90  5'-TCGAG CCCGGG a t g ACTAAAAAACCAGGA GGGCC-3'
J91  3'-      C GGGCCC TAC TGATTTTTTGGTCCT C       -5'
     XhoI    SmaI                              ApaI

J94  5'-       CT tgatttttattga CGGCCG A   -3'
J95  3'-GTACG A ACT AAAAATA ACT GCCGGC TTCGA-5'
     SphI                    EagI  HindIII J96+J97  5'-GGG atg GGCGTTAACGCACGAGACCGATC AATTGCTTTGGCCTTCTTAGCC
J99+J98  3'-CCC TAC CCGCAATTGCGTGCTCTGGCTAGTTAACGAAACCGGAAGAATCGG ACAGGAGGTGTGCTCGTGTTCTTAGCGACCAATGT GCATG-3'
         TGTCCTCCACACGAGCACAAGAATCGCTGGTTACA C    -5'
                                              SphI
```

Construction of Vaccinia Virus Recombinants

Procedures for transfection of recombinant donor plasmids into tissue culture cells infected with a rescuing vaccinia virus and identification of recombinants by in situ hybridization on nitrocellulose filters have been described (Panicali et al., 1982; Guo et al., 1989). JEV24, JEV27, JEV33 and JEV34 were transfected into vP410 infected cells to generate the vaccinia recombinants vP825, vP829, vP857 and vP864 respectively (FIG. 18).

In Vitro Virus Infection and Radiolabeling

HeLa cell monolayers were prepared in 35 mm diameter dishes and infected with vaccinia viruses (m.o.i. of 2) or JEV (m.o.i. of 5) before radiolabeling. At 16 h post infection, cells were pulse labeled with medium containing $^{35}$S-Met and chased for 6 hr in the presence of excess unlabeled Met exactly as described by Mason et al. (1991). JEV-infected cells were radiolabeled as above for preparation of radioactive proteins for checking pre- and post-challenge mouse sera by radioimmunoprecipitation.

Radioimmunoprecipitations, Polyacrylamide Gel Electrophoresis, and Endoglycosidase Treatment Radiolabeled cell lysates and culture fluids were harvested and the viral proteins were immunoprecipitated, digested with endoglycosidases, and separated in SDS-containing polyacrylamide gels (SDS-PAGE) exactly as described by Mason (1989).

Animal Protection Experiments

Mouse protection experiments were performed exactly as described by Mason et al. (1991). Briefly, groups of 3-week- Structure of Recombinant Vaccinia Viruses Four different vaccinia recombinants (in the HA locus) were constructed that expressed portions of the JEV coding region extending from C through NS2B. The JEV cDNA sequences contained in these recombinant viruses are shown in FIG. 18. In all four recombinant viruses the sense strand of the JEV cDNA was positioned behind the vaccinia virus early/late H6 promoter, and translation was expected to be initiated from naturally occurring JEV Met codons located at the 5' ends of the viral cDNA sequences.

Recombinant vP825 encoded the capsid protein C, structural protein precursor prM, the structural glycoprotein E, the nonstructural glycoprotein NS1, and the nonstructural protein NS2A (McAda et al., 1987). Recombinant vP829 encoded the putative 15 aa signal sequence preceding the amino-terminus of prM, as well as prM, and E (McAda et al., 1987). Recombinant vP857 contained a cDNA encoding the 30 aa hydrophobic carboxy-terminus of E, followed by NS1 and NS2A. Recombinant vP864 contained a cDNA encoding the same proteins as vP857 with the addition of NS2B. In recombinants vP825 and vP829 a potential vaccinia virus early transcription termination signal in E (TTTTTGT; nucleotides 1399–1405) was modified to TCTTTGT without altering the aa sequence. This change was made in an attempt to increase the level of expression of E since this sequence has been shown to increase transcription termination in in vitro transcription assays (Yuen et al., 1987).

E and prM Were Properly Processed When Expressed by Recombinant Vaccinia Viruses Pulse-chase experiments demonstrate that proteins identical in size to E were synthesized in cells infected with all recombinant vaccinia viruses containing the E gene (Table 3). In the case of cells infected with JEV, vP555 and vP829, an E protein that migrated slower in SDS-PAGE was also detected in the culture fluid harvested from the infected cells (Table 3). This extracellular form of E produced by JEV- and vP555-infected cells contained mature N-linked glycans (Mason, 1989; Mason et al., 1991), as confirmed for the extracellular forms of E produced by vP829-infected cells. Interestingly, vP825, which contained the C coding region in addition to prM and E specified the synthesis of E in a form that is not released into the extracellular fluid (Table 3). Immunoprecipitations prepared from radiolabeled vaccinia-infected cells using a MAb specific for M (and prM) revealed that prM was synthesized in cells infected with vP555, vP825, and vP829, and M was detected in the culture fluid of cells infected with vP555 or vP829 (Table 3).

The extracellular fluid harvested from cells infected with vP555 and vP829 contained an HA activity that was not detected in the culture fluid of cells infected with vP410, vP825, vP857 or vP864. The HA activity observed in the culture fluid of vP829 infected cells was 8 times as high as that obtained from vP555 infected cells. This HA appeared similar to the HA produced in JEV infected cells based on its inhibition by anti-JEV antibodies and its pH optimum (Mason et al., 1991). Analysis of sucrose density gradients prepared with culture fluids obtained from infected cells identified a peak of HA activity in the vP829 sample that co-migrated with the peak of slowly sedimented hemagglutinin (SHA) found in the JEV culture fluids (Table 3). This result indicated that vP829 infected cells produced extracellular particles similar to the empty viral envelopes containing E and M which are observed in the culture fluids harvested from vP555 infected cells (FIG. 9).

NS1 Was Properly Processed and Secreted When Expressed By Recombinant Vaccinia Virus The results of pulse-chase experiments demonstrated that proteins identical in size to authentic NS1 and NS1' were synthesized in cells infected with vP555, vP825, vP857 and vP864 (Table 3). NS1 produced by vP555-infected cells was released into the culture fluid of infected cells in a higher molecular weight form. NS1 was also released into the culture fluid of cells infected with vP857 and vP864 (Table 3). Comparison of the synthesis of NS1 from vaccinia viruses containing either the NS2A (vP857) or both the NS2A and NS2B (vP864) coding regions showed that the presence or absence of the NS2B coding region had no affect on NS1 expression, consistent with previous data showing that only the NS2A gene is needed for the proper processing of NS1 (Falgout et al., 1989; Mason et al., 1991). The efficiency of release of NS1 by vP825 infected cells was more than 10 times less than that for NS1 synthesized in vP555, vP857 or vP864 infected cells.

Recombinant Vaccinia Viruses Induced Immune Responses To JEV Antigens

Pre-challenge sera pooled from selected animals in each group were tested for their ability to immunoprecipitate radiolabeled E and NS1. The results of these studies (Table 3) demonstrated that: (1) the following order of immune response to E vP829>vP555>vP825, (2) all viruses encoding NS1 and NS2A induced antibodies to NS1, and (3) all immune responses were increased by a second inoculation with the recombinant viruses. Analysis of the neutralization and HAI data for the sera collected from these animals (Table 4) confirmed the results of the immunoprecipitation analyses, showing that the immune response to E as demonstrated by RIP correlated well with these other serological tests (Table 4).

Vaccination With the Recombinant Viruses Provided Protection From Lethal JEV Infection All of the recombinant vaccinia viruses were able to provide mice with some protection from lethal infection by the peripherally pathogenic P3 strain of JEV (Huang, 1982) (Table 4). These studies confirmed the protective potential of vP555 (Mason et al., 1991) and demonstrated similar protection in animals inoculated with vP825 and vP829. Recombinant viruses vP857 and vP864 which induced strong immune responses to NS1 showed much lower levels of protection, but mice inoculated with these recombinants were still significantly protected when compared to mice inoculated with the control virus, vP410 (Table 4).

Post-Challenge Immune Responses Document the Level of JEV Replication

In order to obtain a better understanding of the mechanism of protection from lethal challenge in animals inoculated with these recombinant viruses, the ability of antibodies in post-challenge sera to recognize JEV antigens was evaluated. For these studies an antigen from radiolabeled JEV-infected cell lysates was utilized and the response to the NS3 protein which induces high levels of antibodies in hyperimmunized mice (Mason et al., 1987a) was examined. The results of these studies (Table 5) correlated perfectly with the survival data in that groups of animals vaccinated with recombinant viruses that induced high levels of protection (vP829, vP555, and vP825) showed low post-challenge responses to NS3, whereas the sera from survivors of groups vaccinated with recombinants that expressed NS1 alone (vP857 and vP864) showed much higher post-challenge responses to NS3.

TABLE 3

Characterization of proteins expressed by vaccinia recombinants and their immune responses

|  | vP555 | vP829 | vP825 | vP857 | vP864 |
|---|---|---|---|---|---|
| Proteins expressed |  |  |  |  |  |
| Intracellular | prM,E NS1 | prM,E | prM,E NS1 | NS1 | NS1 |
| secreted | M,E,NS1 | M,E | NS1 | NS1 | NS1 |
| Particle formation | + | + | − | − | − |
| Immune response |  |  |  |  |  |
| single | E | E | NS1 | NS1 | NS1 |
| double | E,NS1 | E | E,NS1 | NS1 | NS1 | single = single inoculation with $10^7$ pfu vaccinia recombinants (ip)
double = two inoculations with $10^7$ pfu vaccinia recombinants (ip) 3 weeks apart

TABLE 4

Protection of mice and immune response

| Protection | vP555 | vP829 | vP825 | vP857 | vP864 |
|---|---|---|---|---|---|
| single | 7/10 | 10/10 | 8/10 | 0/10 | 1/10 |
| double | 10/10 | 9/10 | 9/10 | 5/10 | 6/10 |
| Neut titer |  |  |  |  |  |
| single | 1:20 | 1:160 | 1:10 | <1:10 | <1:10 |
| double | 1:320 | 1:2560 | 1:320 | <1:10 | <1:10 |

TABLE 4-continued

Protection of mice and immune response

HAI titer

| | | | | | |
|---|---|---|---|---|---|
| single | 1:20 | 1:40 | 1:10 | <1:10 | <1:10 |
| double | 1:80 | 1:160 | 1:40 | <1:10 | <1:10 | single = single inoculation with $10^7$ pfu vaccinia recombinants (ip) and challenge 3 weeks later with $4.9 \times 10^5$ LD$_{50}$ P3 strain JEV (ip)
double = two inoculations with $10^7$ pfu vaccinia recombinants (ip) 3 weeks apart and challenge 3 weeks later with $1.3 \times 10^3$ LD$_{50}$ P3 strain JEV (ip).

TABLE 5

Post challenge immune response

| Inoculations | vP555 | vP829 | vP825 | vP857 | vP864 |
|---|---|---|---|---|---|
| single | ++ | + | ++ | −[a] | ++++ |
| double | +/−[b] | − | − | ++ | +++ |

+ NS3 antibodies present in post-challenge sera
[a]No surviving mice
[b]Very low level NS3 antibodies present in post-challenge sera

EXAMPLE 10—CLONING OF JEV GENES INTO A VACCINIA (NYVAC) DONOR PLASMID

Plasmid pMP2VCL (containing a polylinker region within vaccinia sequences upstream of the KiL host range gene) was digested within the polylinker with HindIII and XhoI and ligated to annealed oligonucleotides SPHPRHA A through D generating

```
                    HinIII
A+B 5'- AGCTTCTTTATTCTATACTTAAAAAGTGAAAATAAATACAAAGGTTCTTGAGGGTTGTG
D+C 3'-         AGAAATAAGATATGAATTTTTCACTTTTATTTATGTTTCCAAGAACTCCCAACAC

EcoRV
          TTAAATTGAAAGCGAGAAATAATCATAAATTATTTCATTATCGCGATATCCGTTAAGTT A+B
          AATTTAACTTTCGCTCTTTATTAGTATTTAATAAAGTAATAGCGCTATAGGCAATTCAA D+C

TGTATCGTAC  -3'       A+B
          ACATAGCATGAGCT -5'    D+C
                       XhoI
```

SPHPRHA A (SEQ ID NO:31)
5'-AGCTTCTTTATTCTATACTTAAAAAGTGAAAATAA ATACAAAGGTTCTTGAGGGT - 3'
SPHPRHA B (SEQ ID NO:32)
5'-TGTGTTAAATTGAAAGCGAGAAATAATCATAAATT ATTTCATTATCGCGATATCCGTTAAGTTTG TATCG-TAC - 3'
SPHPRHA C (SEQ ID NO:33)
3'-TTATTAGTATTTAATAAAGTAATAGCGCTATAGGCA ATTCAAACATAGCATGAGCT - 5'
SPHPRHA D (SEQ ID NO:34)
3'-AGAAATAAGATATGAATTTTTCACTTTTATTTATGT TTCCAAGAACTCCCAACACAATTTAACTT TCGCTCT - 5'

SP126 containing a HindIII site, H6 promoter −124 through −1 (Perkus et al., 1989) and XhoI, KpnI, SmaI, SacI and EcoRI sites.

Plasmid pSD544VC (containing vaccinia sequences surrounding the site of the HA gene replaced with a polylinker region and translation termination codons in six reading frames) was digested with XhoI within the polylinker, filled in with the Klenow fragment of DNA polymerase I and treated with alkaline phosphatase. SP126 was digested with HindIII, treated with Klenow and the H6 promoter isolated by digestion with SmaI. Ligation of the H6 promoter fragment to pSD544VC generated SPHA-H6 which contained the H6 promoter in the polylinker region (in the direction of HA transcription).

Plasmid JEVL14VC (FIG. 1) was digested with EcoRV in the H6 promoter and SacI in JEV sequences (nucleotide 2124) and a 1789 bp fragment isolated. JEVL14VC was digested with EclXI at the EagI site following the T5NT, filled in with the Klenow fragment of DNA polymerase I and digested with SacI in JEV sequences (nucleotide 2124) generating a 2005 bp fragment. The 1789 bp EcoRV-SacI and 2005 bp (SacI-filled EclXI) fragments were ligated to EcoRV (within H6) and SmaI digested (within polylinker) and alkaline phosphatase treated SP126 generating JEV35. JEV35 was transfected into vP866 (NYVAC) infected cells to generate the vaccinia recombinant vP908 (FIG. 18).

JEV35 was digested with SacI (within JE sequences nucleotide 2124) and EclXI (after T5NT) a 5497 bp fragment isolated and ligated to a SacI (JEV nucleotide 2125) to EagI fragment of JEV25 (containing the remaining two thirds of E, translation stop and T5NT) generating JEV36. JEV36 was transfected into vP866 (NYVAC) infected cells to generate the vaccinia recombinant vP923 (FIG. 18). Oligonucleotides SPHPRHA A through D (SEQ ID NO:31), (SEQ ID NO:32), (SEQ ID NO:33) and (SEQ ID NO:34) are ligated to generate the following sequences (SEQ ID NO:56/ SEQ ID NO:57)

Animal Protection Experiment

Mouse protection experiments were performed exactly as described by Mason et al. (1991). Groups of 3 week old mice were immunized by intraperitoneal (ip) injection of $10^7$ pfu of vaccinia virus, and 3 weeks later sera were collected from selected mice. Mice were then challenged by ip injection with a suspension of suckling mouse brain infected with the P3 strain of JEV (multiple mouse passage; Huang, 1982). Following challenge mice were observed daily for three weeks.

Evaluation of Immune Response to JEV NYVAC Recombinants

Hemagglutinin inhibition (HAI) tests were performed as described by Mason et al. (1991).

Vaccination with JEV NYVAC Recombinants Provided Protection from Lethal JEV Infection NYVAC recombinants vP908 and VP923 elicited high levels of hemagglutination-inhibiting antibodies and protected mice against more than 100,000 LD$_{50}$ of JEV (Table 6).

TABLE 6

Ability of JEV NYVAC recombinants to protect mice from lethal JEV encephalitis

| Immunizing Virus | Pre-challenge | Survival/total |
|---|---|---|
| NYVAC (vP866) | <1:10 | 0/12 |
| vP908 | 1:80 | 11/12 |
| vP923 | 1:80 | 10/10 |

Immunization - one inoculation of $10^7$ pfu, ip route.
Challenge - 3 weeks post immunization $3.8 \times 10^5$ $LD_{50}$ P3 strain JEV ip route

EXAMPLE 11—CLONING OF YF GENES INTO A VACCINIA VIRUS DONOR PLASMID

A host range mutant of vaccinia virus (WR strain) vP293 (Perkus et al., 1989), was used to generate all recombinants (see below). All vaccinia virus stocks were produced in either VERO (ATCC CCL81) or MRC-5 (ATCC CCL171) cells in Eagles MEM supplemented with 5–10% newborn calf serum (Flow Laboratories, McLean, VA).

The YF 17D cDNA clones used to construct the YF vaccinia recombinant viruses (clone 10III and clone 28III), were obtained from Charles Rice (Washington University School of Medicine, St. Louis, MO), all nucleotide coordinates are derived from the sequence data presented in Rice et al., 1985.

Plasmid YFO containing YF cDNA encoding the carboxy-terminal 80% prM, E and amino-terminal 80% NS1 (nucleotides 537–3266) was derived by cloning an AvaI to NsiI fragment of YF cDNA (nucleotides 537–1658) and an NsiI to KpnI fragment of YF CDNA (nucleotides 1659–3266) into AvaI and KpnI digested IBI25 (International Biotechnologies, Inc., New Haven, CT). Plasmid YF1 containing YF cDNA encoding C and amino-terminal 20% prM (nucleotides 119–536) was derived by cloning a RsaI to AvaI fragment of YF cDNA (nucleotides 166–536) and annealed oligos SP46 and SP47 (containing a disabled HindIII sticky end, XhoI and ClaI sites and YF nucleotides 119–165) into AvaI and HindIII digested IBI25. Plasmid YF3 containing YF cDNA encoding the carboxy-terminal 60% of E and amino-terminal 25% of NS1 was generated by cloning an ApaI to BamHI fragment of YF CDNA (nucleotides 1604–2725) into ApaI and BamHI digested IBI25. Plasmid YF8 containing YF cDNA encoding the carboxy-terminal 20% NS1 NS2A, NS2B and amino-terminal 20% NS3 was derived by cloning a KpnI to XbaI fragment of YF CDNA (nucleotides 3267–4940) into KpnI and XbaI digested IBI25. Plasmid YF9 containing YF cDNA encoding the carboxy-terminal 60% NS2B and amino-terminal 20% NS3 was generated by cloning a SacI to XbaI fragment of YF cDNA (nucleotides 4339–4940) into SacI and XbaI digested IBI25. Plasmid YF13 containing YF cDNA encoding the carboxy-terminal 25% of C, prM and amino-terminal 40% of E was derived by cloning a BalI to AnaI fragment of YF cDNA (nucleotides 384–1603) into ApaI and SmaI digested IBI25.

Oligonucleotide-directed mutagenesis (Kunkel, 1985) was used to change potential vaccinia virus early transcription termination signals (Yuen et al., 1987) 49 aa from the amino-terminus of the C gene in YF1 (TTTTTCT nucleotides 263–269 and TTTTTGT nucleotides 269–275) to (SEQ ID NO:35) TTCTTCTTCTTGT creating plasmid YF1B, in the E gene in YF3 (nucleotides 1886–1893 TTTTTTGT to TTCTTTGT 189 aa from the carboxy-terminus and nucleotides 2429–2435 TTTTTGT to TTCT-TGT 8 aa from the carboxy-terminus) creating plasmids YF3B and YF3C. A PstI to BamHI fragment from YF3C (nucleotides 1965–2725) was exchanged for the corresponding fragment of YF3B generating YF4 containing YF CDNA encoding the carboxy-terminal 60% E and amino-terminal 25% NS1 (nucleotides 1604–2725) with both mutagenized transcription termination signals. An ApaI to BamHI fragment from YF4 (nucleotides 1604–2725) was substituted for the equivalent region in YFO creating plasmid YF6 containing YF cDNA encoding the carboxy-terminal 80% prM, E and amino-terminal 80% NS1 (nucleotides 537–3266) with both mutagenized transcription termination signals. Plasmid YF6 was digested with EcoRV within the IBI25 sequences and AvaI at nucleotide 537 and ligated to an EcoRV to AvaI fragment from YF1B (EcoRV within IBI25 to AvaI at nucleotide 536) generating YF2 containing YF cDNA encoding C through the amino-terminal 80% of NS1 (nucleotides 119–3266) with an XhoI and ClaI site at 119 and four mutagenized transcription termination signals.

Oligonucleotide-directed mutagenesis described above was used to insert XhoI and ClaI sites preceding the ATG 17 aa from the carboxy-terminus of E (nucleotides 2402–2404) in plasmid YF3C creating YF5, to insert XhoI and ClaI sites preceding the ATG 19 aa from the carboxy-terminus of prM (nucleotides 917–919) in plasmid YF13 creating YF14, to insert an XhoI site preceding the ATG 23 aa from the carboxy-terminus of E (nucleotides 2384–2386) in plasmid YF3C creating plasmid YF25, and to insert an XhoI site and ATG (nucleotide 419) in plasmid YF121 aa from the carboxy-terminus of C generating YF45.

An ApaI to BamHI fragment from YF5 (nucleotides 1604–2725) was exchanged for the corresponding region of YFO creating YF7 containing YF cDNA encoding the carboxy-terminal 80% prM, E and amino-terminal 80% NS1 (nucleotides 537–3266) with XhoI and ClaI sites at 2402 (17 aa from the carboxy-terminus of E) and a mutagenized transcription termination signal at 2429–2435 (8 aa from the carboxy-terminus of E). The ApaI to BamHI fragment from YF25 (nucleotides 1604–2725) was exchanged for the corresponding region of YFO generating YF26 containing YF cDNA encoding the carboxy-terminal 80% prM, E and amino-terminal 80% NS1 (nucleotides 537–3266) with an XhoI site at nucleotide 2384 (23 aa from the carboxy-terminus of E) and mutagenized transcription termination signal at 2428–2435 (8 aa from the carboxy-terminus of E).

An AvaI to ApaI fragment from YF14 (nucleotides 537–1603) was substituted for the corresponding region in YF6 generating YF15 containing YF cDNA encoding the carboxy-terminal 80% prM, E and amino-terminal 80% NS1 (nucleotides 537–3266) with XhoI and ClaI sites at nucleotide 917 (19 aa from the carboxy-terminus of prM) and two mutagenized transcription termination signals. YF6 was digested within IBI25 with EcoRV and within YF at nucleotide 537 with AvaI and ligated to EcoRV (within IBI25) to AvaI fragment of YF45 generating YF46 containing YF CDNA encoding C through the amino-terminal 80% NS1 (nucleotides 119–3266) with an XhoI site at 419 (21 aa from the carboxy-terminus of C) and two transcription termination signals removed.

Oligonucleotide-directed mutagenesis described above was used to insert a SmaI site at the carboxy-terminus of NS2B (nucleotide 4569) in plasmid YF9 creating YF11, and to insert a SmaI site at the carboxy-terminus of NS2A (nucleotide 4180) in plasmid YF8 creating YF10. A SacI to XbaI fragment from YF11 (nucleotides 4339–4940) and Asp718 to SacI fragment from YF8 (nucleotides 3262–4338) were ligated to Asp718 and XbaI digested IBI25 creating YF12 containing YF cDNA encoding the carboxy-terminal 20% NS1, NS2A, NS2B and amino-terminal 20% NS3 (nucleotides 3262–4940) with a SmaI site after the carboxy-terminus of NS2B (nucleotide 4569).

Plasmid pHES4 contains the vaccinia K1L host range gene, the early/late vaccinia virus H6 promoter, unique multicloning restriction sites, translation stop codons and an early transcription termination signal (Perkus et al., 1989) A KpnI to SmaI fragment from YF12 encoding carboxy-terminal 20% NS1, NS2A and NS2B (nucleotides 3267–4569), XhoI to KpnI fragment from YF1S encoding 19 aa prM, E and amino-terminal 80% NS1 (nucleotides 917–3266) and XhoI-SmaI digested pHES4 were ligated generating YF23. An XhoI to BamHI fragment from YF26 encoding 23 aa E, amino-terminal 25% NS1 (nucleotides 2384–2725) was ligated to an XhoI to BamHI fragment from YF23 (containing the carboxy-terminal 75% NS1, NS2A and NS2B, the origin of replication and vaccinia sequences) generating YF28.

XhoI-SmaI digested pHES4 was ligated to a purified XhoI to XpnI fragment from YF7 encoding 17 aa E and amino-terminal 80% NS1 (nucleotides 2402–3266) plus a KpnI to SmaI fragment from YF10 encoding the carboxy-terminal 20% NS1 and NS2A (nucleotides 3267–4180) creating YF18. An XhoI to BamHI fragment from YF2 encoding C, prM, E and amino-terminal 25% NS1 (nucleotides 119–2725) was ligated to a XhoI to BamHI fragment of YF18 (containing the carboxy-terminal 75% NS1 and NS2A, the origin of replication and vaccinia sequences) generating YF19. The same XhoI to BamHI fragment from YF2 was ligated to a XhoI to BamHI fragment from YF28 (containing the carboxy-terminal 75% NS1 and NS2A, the origin of replication and vaccinia sequences) generating YF20. A XhoI to BamHI fragment from YF46 encoding 21 aa C, prM, E and amino-terminal 25% NS1 (nucleotides 419–2725) was ligated to the XhoI to BamHI fragment from YF18 generating YF47. Oligonucleotide SP46 (SEQ ID NO:36) and SP47 (SEQ ID NO:37) are as follows:

HeLa cell monolayers were infected with vaccinia virus (m.o.i.=2) or YF17D (m.o.i.=4) before radiolabeling. At 38 hr post infection for YF17D or 16 hr post infection for vaccinia, cells were pulsed labeled with medium containing $^{35}$S-Met and chased for 6 hr in the presence of excess unlabeled Met.

Radioimmunoprecipitations and Polyacrylamide Gel Electrophoresis

Radiolabeled cell lysates and culture fluids were harvested and the viral proteins were immunoprecipitated with monoclonal antibodies to YF E and NS1 and separated in SDS-containing polyacrylamide gels exactly as described by Mason (1989).

Animal Protection Experiments

Groups of 3 week old mice were immunized by intraperitoneal injection with 107 pfu of vaccinia virus or 100 μl of a 10% suspension of suckling mouse brain containing YF17D. Three weeks later sera were collected from selected mice. Mice were then either re-inoculated with the recombinant virus or YF17D, or challenged by i.c. injection of the French Neurotropic strain of YFV. Three weeks later the boosted animals were re-bled and challenged with the French Neurotropic strain of YFV. Following challenge, mice were observed at daily intervals for three weeks and lethal dose titrations were performed in each experiment using litter mates of the experimental animals. In addition, sera were collected from all surviving animals 4 weeks after challenge.

Evaluation of Immune Response to the Recombinant Vaccinia Viruses

Sera were tested for their ability to precipitate radiolabeled YFV proteins from detergent-treated cell lysates as described by Mason et al. (1991). Neutralization tests were performed as described by Mason et al. (1991) except human sera was not added to the virus/antibody dilutions. Hemagglutination tests and hemagglutinin-inhibition (HAI) tests were performed as described by Mason et al. (1991).

Structure of Recombinant Vaccinia Viruses

Five different vaccinia virus recombinants that expressed portions of the YF coding region extending from C through

```
        HindIII
SP46  5'- AGCTT CTCGAGCATCGATTACT a t g TCTGGTCGTAAAGCTCAGGGAAAAACC
SP47  3'-       A GAGCTCGTAGCTAATGATACAGACCAGCATTTCCGAGTCCCTTTTTGG

CTGGGCGTCAATATGGT  -3'
      GACCCGCAGTTATACCA  -5'
```

Construction of Vaccinia Recombinants

Procedures for transfection of recombinant donor plasmids into tissue culture cells infected with a rescuing vaccinia virus and identification of recombinants by host range selection and in situ hybridization on nitrocellulose filters have been described (Perkus et al., 1989). YF18, YF23, YF20, YF19 and YF47 were transfected into host range mutant vP293 (Perkus et al. 1989) infected cells to generate the vaccinia recombinants vP725, vP729, vP764, vP766 and vP869. vP457 containing a host range gene restored in the vP293 background has been described (Perkus et al., 1989).

In Vitro Infection and Radiolabeling

Vero cell monolayers were infected with vaccinia virus for 1 hr (m.o.i.=10) before radiolabeling. After the absorption period the inoculum was removed and infected cells were overlaid with Met-free media (MEM) containing 20 uCi/ml $^{35}$S-Met and 2% dialyzed FBS. All samples were harvested at 8 hr post infection.

Figure 19:
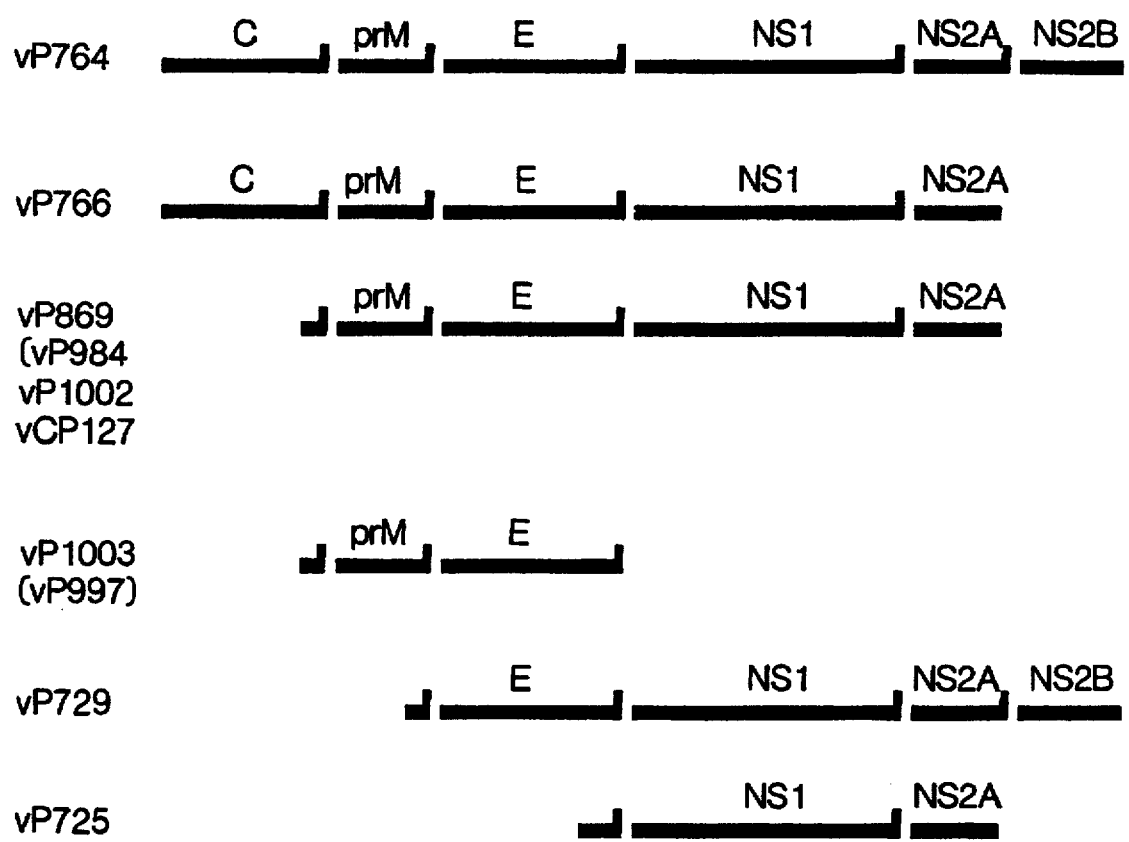
FIG. 19 is a map of the YF coding regions inserted in the vaccinia viruses vP766, vP764, vP869, vP729, vP725, vP984, vP997, vP1002, vP1003 and canarypox virus vCP127.

NS2B were constructed utilizing a host range selection system (Perkus et al., 1989). The YF cDNA sequences contained in these recombinants are shown in FIG. 19. In all five recombinant viruses the sense strand of YF cDNA was positioned behind the vaccinia virus early/late H6 promoter, and translation was expected to be initiated from Met codons located at the 5' ends of the viral cDNA sequences (FIG. 19).

Recombinant vP725 encoded the putative 17-aa signal sequence preceding the N terminus of the nonstructural protein NS1 and the nonstructural proteins NS1 and NS2A (Rice et al., 1985). Recombinant vP729 encoded the putative 19-aa signal sequence preceding the N terminus of E, E, NS1, NS2A and NS2B (Rice et al., 1985). Recombinant vP764 encoded C, prM, E, NS1, NS2A and NS2B (Rice et al., 1985). Recombinant vP766 encoded C, prM, E, NS1 and NS2A (Rice et al., 1985). Recombinant vP869 encoded the putative 21-aa signal sequence preceding the N terminus of the structural protein precursor prM, prM E, NS1 and NS2A (Rice et al., 1985).

E Protein Expression By Recombinant Vaccinia Virus

Pulse-chase experiments in HeLa cells demonstrated that a protein identical in size to YF17D E was synthesized in cells infected with vP869 and secreted into the culture fluid (Table 7). Under the same conditions of labeling, no intracellular or extracellular E was detected in cultures infected with vP766, vP729 or the control vaccinia virus vP457 (Table 7).

Continuous label experiments in Vero cells demonstrated that a protein identical in size to the E protein expressed by vP869 was expressed in cultures infected with vP766 and vP729 (Table 7). These results suggest that the E protein produced by vP869 infected cells is present in a form in which it is more stable than the E protein expressed by vP766 or vP729. YF17D has previously been shown to produce a more labile E protein than other YF isolates (Cane et al. 1989).

The extracellular fluid harvested from cells infected with vP869 contained an HA activity that was not detected in the culture fluid of vP766, vP729, vP725, or vP457 infected cells (Table 7). This HA appeared similar to the HA produced in YF17D infected cells based on its pH optimum.

NS1 Protein Expression By Recombinant Vaccinia Virus

The results of pulse-chase experiments in HeLa cells demonstrated that proteins identical in size to authentic YF17D NS1 were synthesized in cells infected with vP725, vP766, and vP729 (Table 7), however, the amounts synthesized greatly varied. NS1 produced by vP725 and vP729 infected cells was released into the culture fluid of infected cells in a higher molecular weight form similar to NS1 secreted by YF17D infected cells. vP766 infected cells did not secrete NS1, however, the level of intracellular NS1 was lowest with this recombinant (Table 7). The failure of vP869 to synthesize NS1 is due to the deletion of a base (nucleotide 2962) in the donor plasmid (YF47) used to generate this recombinant.

Protection From Lethal YF Challenge

In an initial experiment vP457, vP764, and vP869 were compared with YF17D in their ability to protect mice from a lethal challenge with the French Neurotropic strain of YFV (Table 8, Experiment I). vP869 provided significant protection whereas vP764 offered no better protection than the control vaccinia virus vP457.

A second protection experiment was performed comparing the ability of vP869, vP766, vP725, vP729, and vP457 to YF17D to protect mice against lethal challenge with French Neurotropic strain YFV (Table 8, Experiment II). Mice receiving either one or two inoculations or vP869 were protected from challenge, none of the other recombinants were protective after either one or two inoculations. Furthermore, the levels of protection achieved in the vP869-inoculated mice were equivalent to those achieved by immunization with YF17D. Pre-challenge sera pooled from selected animals in each group were tested for their ability to immunoprecipitate radiolabeled E and NS1 proteins and for the presence of Neut and HAI antibodies. As shown in Table 9 only vP869 and YF17D immunized mice responded to E protein, the response was increased by a second inoculation. Mice immunized twice with vP729, vP725 or vP766 produced antibody to NS1. High levels of Neut (Table 10) and HAI antibodies (Table 11) were present in vP869 inoculated mice, but not in mice inoculated with any of the other recombinants, confirming the results of the immunoprecipitation analysis and suggesting that these high levels of antibody are required for protection.

TABLE 7

Characterization of proteins expressed by vaccinia recombinants and YF17D

|  | 17D | vP869 | vP729 | vP725 | vP766 | vP457 |
|---|---|---|---|---|---|---|
| YF Proteins Expressed |  |  |  |  |  |  |
| Intracellular | E,NS1 | E | E,NS1 | NS1 | E,NS1 | NONE |
| Secreted | E,NS1 | E | NS1 | NS1 | NONE | NONE |
| Extracellular HA Activity | YES | YES | NO | NO | NO | NO |

TABLE 8

Protection of mice from lethal YF challenge

Experiment I

| Recombinant | Survival/total |
|---|---|
| vP457 | 2/10 |
| vP764 | 2/10 |
| vP869 | 9/10 |
| YF17D | 5/10 |

Experiment II

| Recombinant | Survival/total single immunization[a] | double immunization[b] |
|---|---|---|
| vP457 | 0/16 | 1/14 |
| vP725 | 0/14 | 2/16 |
| vP729 | 0/16 | 2/13 |
| vP766 | 0/14 | 0/14 |
| vP869 | 8/15 | 15/16 |
| YF17D | 10/13 | 16/16 |

[a]mice were inoculated ip with $10^7$ pfu vaccinia recombinant or 100 µl of a 10% suspension of suckling mouse brain containing YF17D and challenged three weeks later ic with 220 $LD_{50}$ French Neurotropic strain YFV.
[b]mice were inoculated twice three weeks apart ip with $10^7$ pfu vaccinia recombinant or 100 µl of a 10% suspension of suckling mouse brain containing YF17D and challenged three weeks later ic with 36 $LD_{50}$ French Neurotropic strain YFV.

TABLE 9

Pre-challenge Radioimmunoprecipitation

| | One Inoculation | | Two Inoculations | |
|---|---|---|---|---|
| Immunizing Virus | Anti-E | Anti-NS1 | Anti-E | Anti-NS1 |
| vP457 | − | − | − | − |
| vP725 |  |  |  | + |
| vP729 |  |  |  | + |
| vP766 |  |  |  | + |
| vP869 | + | − | ++ | − |
| 17D | + | − | ++ | − |

TABLE 10

Plaque reduction neutralization titers in prechallenge sera

| Immunizing Virus[a] | One Inoculation[b] | Two Inoculations[b] |
|---|---|---|
| vP457 Group I | <1:10 |  |
| vP457 Group II | <1:10 | <1:10 |
| vP725 Group I | <1:10 |  |
| vP725 Group II | <1:10 | <1:10 |
| vP729 Group I | <1:10 |  |
| vP729 Group II | <1:10 | <1:10 |

TABLE 10-continued

Plaque reduction neutralization titers in prechallenge sera

| Immunizing Virus[a] | One Inoculation[b] | Two Inoculations[b] |
|---|---|---|
| vP766 Group I | <1:10 | |
| vP766 Group II | <1:10 | <1:10 |
| vP869 Group I | 1:40 | |
| vP869 Group II | 1:80 | 1:160 |
| 17D Group I | 1:80 | |
| 17D Group II | 1:160 | 1:640 |

[a]virus used for immunization. Group I indicates animals challenged three weeks following a single inoculation. Group II indicates animals challenged following two inoculations.
[b]serum dilution yielding 90% reduction in plaque number.

TABLE 11

HAI antibody titers in prechallenge sera

| Immunizing Virus[a] | One Inoculation[b] | Two Inoculations[b] |
|---|---|---|
| vP457 Group I | <1:10 | |
| vP457 Group II | <1:10 | <1:10 |
| vP725 Group I | <1:10 | |
| vP725 Group II | <1:10 | <1:10 |
| vP729 Group I | <1:10 | |
| vP729 Group II | <1:10 | <1:10 |
| vP766 Group I | <1:10 | |
| vP766 Group II | <1:10 | <1:10 |
| vP869 Group I | 1:80 | |
| vP869 Group II | 1:80 | 1:320 |
| 17D Group I | 1:80 | |
| 17D Group II | 1:40 | 1:1280 |

[a]virus used for immunization. Group I indicates animals challenged three weeks following a single inoculation. Group II indicates animals challenged following two inoculations.
[b]serum dilution.

Example 12—CLONING OF YF GENES INTO A NYVAC DONOR PLASMID

A XhoI to SmaI fragment from YF47 (nucleotides 419–4180) containing YF CDNA encoding 21 amino acids C, prM, E, NS1, NS2A (with a base missing in NS1 nucleotide 2962) was ligated to XhoI-SmaI digested SPHA-H6 (HA region donor plasmid) generating YF48. YF48 was digested with SacI (nucleotide 2490) and partially digested with Asp718 (nucleotide 3262) and a 6700 bp fragment isolated (containing the plasmid origin of replication, vaccinia sequences, 21 amino acids C, prM, E, amino-terminal 3.5% NS1, carboxy-terminal 23% NS1, NS2A) and ligated to a SacI-Asp718 fragment from YF18 (containing the remainder of NS1 with the base at 2962) generating YF51. The 6 bp corresponding to the unique XhoI site in YF51 were removed using oligonucleotide-directed double-strand break mutagenesis (Mandecki, 1986) creating YF50 encoding YF 21 amino acids C, prM, E, NS1, NS2A in the HA locus donor plasmid. YF50 was transfected into vP866 (NYVAC) infected cells generating the recombinant vP984 (FIG. 19). YF50 was transfected into vP913 infected cells (NYVAC-MV) generating the recombinant vP1002 (FIG. 19).

The 6 bp corresponding to the unique XhoI site in YF48 were removed using oligonucleotide-directed double-strand break mutagenesis creating YF49. Oligonucleotide-directed mutagenesis (Kunkel, 1985) was used to insert a SmaI site at the carboxy-terminus of E (nucleotide 2452) in YF4 creating YF16. ApaI-SmaI fragment of YF49 (containing the plasmid origin of replication, vaccinia sequences and YF CDNA encoding 21 amino acids C, prM, and amino-terminal 43% E) was ligated to an ApaI-SmaI fragment from YF16 (nucleotides 1604–2452 containing the carboxy-terminal 57% E) generating YF53 containing 21 amino acids C, prM, E in the HA locus donor plasmid. YF53 was transfected into vP866 (NYVAC) infected cells generating the recombinant vP1003 (FIG. 19). YF53 was transfected into vP913 infected cells (NYVAC-MV) generating the recombinant vP997 (FIG. 19).

Example 13—CLONING OF DENGUE TYPE 1 INTO A VACCINIA VIRUS DONOR PLASMID

The DEN cDNAs used to construct the DEN vaccinia recombinants were derived from a Western Pacific strain of DEN-1 (Mason et al., 1987b). Nucleotide coordinates 1–3745 are presented in that publication. FIG. 20 (SEQ ID NO:53) presents the sequence of nucleotides 3392 to 6117.

Plasmid DEN1 containing DEN cDNA encoding the carboxy-terminal 84% NS1 and amino-terminal 45% NS2A (nucleotides 2559–3745, Mason et al., 1987B) was derived by cloning an EcoRI-XbaI fragment of DEN cDNA (nucleotides 2579–3740) and annealed oligonucleotides DEN1 (SEQ ID NO:38) and DEN2 (SEQ ID NO:39) (containing a XbaI sticky end, translation termination codon, T5AT vaccinia virus early transcription termination signal Yuen et al. (1987), EagI site and HindIII sticky end) into HindIII-EcoRI digested pUC8. An EcoRI-HindIII fragment from DEN1 (nucleotides 2559–3745) and SacI-EcoRI fragment of DEN CDNA encoding the carboxy-terminal 36% of E and amino-terminal 16% NS1 (nucleotides 1447–2559, Mason et al., 1987B) were ligated to HindIII-SacI digested IBI24 (International Biotechnologies, Inc., New Haven, Conn.) generating DEN3 encoding the carboxy-terminal 64% E through amino-terminal 45% NS2A with a base missing in NS1 (nucleotide 2467).

HindIII-XbaI digested IBI24 was ligated to annealed oligonucleotides DEN9 (SEQ ID NO:40) and DEN10 (SEQ ID NO:41) [containing a HindIII sticky end, SmaI site, DEN nucleotides 377–428 (Mason et al., 1987B) and XbaI sticky end] generating SPD910. SPD910 was digested with SacI (within IBI24) and AvaI (within DEN at nucleotide 423) and ligated to an AvaI-SacI fragment of DEN cDNA (nucleotides 424–1447 Mason et al., 1987B) generating DEN4 encoding the carboxy-terminal 11 aa C, prM and amino-terminal 36% E.

Plasmid DEN6 containing DEN cDNA encoding the carboxy-terminal 64% E and amino-terminal 18% NS1 (nucleotides 1447–2579 with nucleotide 2467 present Mason et al., 1987B) was derived by cloning a SacI-XhoI fragment of DEN cDNA into IBI25 (International Biotechnologies, Inc., New Haven, Conn.). Plasmid DEN15 containing DEN cDNA encoding 51 bases of the DEN 5' untranslated region, C, prM and amino-terminal 36% E was derived by cloning a HindIII-SacI fragment of DEN cDNA (nucleotides 20– 1447, Mason et al., 1987B) into HindIII-SacI digested IBI25. Plasmid DEN23 containing DEN CDNA encoding the carboxy-terminal 55% NS2A and amino-terminal 28% NS2B (nucleotides 3745–4213, FIG. 20) (SEQ ID NO:53) was derived by cloning a XbaI-SphI fragment of DEN cDNA into XbaI-SphI digested IBI25. Plasmid DEN20 containing DEN cDNA encoding the carboxy-terminal 55% NS2A, NS2B and amino-terminal 24 amino acids NS3 (nucleotides 3745–4563, FIG. 20) (SEQ ID NO:53) was derived by cloning a XbaI to EcoRI fragment of DEN cDNA into XbaI-EcoRI digested IBI25.

Oligonucleotide-directed mutagenesis (Kunkel, 1985) was used to change potential vaccinia virus early transcription termination signals (Yuen et al., 1987) in the prM gene in DEN4 29 aa from the carboxy–terminus (nucleotides 822–828 TTTTTCT to TATTTCT) and 13 aa from the carboxy-terminus (nucleotides 870–875 TTTTTAT to TATTTAT) creating plasmid DEN47, and in the NS1 gene in DEN6 17 aa from the amino-terminus (nucleotides 2448–2454 TTTTTGT to TATTTGT) creating plasmid DEN7.

Oligonucleotide-directed mutagenesis described above was used to insert an EagI and EcoRI site at the carboxy-terminus of NS2A (nucleotide 4102) in plasmid DEN23 creating DEN24, to insert a SmaI site and ATG 15 aa from the carboxy-terminus of E in DEN7 (nucleotide 2348) creating DEN10, to insert an EagI and HindIII site at the carboxy-terminus of NS2B (nucleotide 4492) in plasmid DEN20 creating plasmid DEN21, and to replace nucleotides 60–67 in plasmid DEN15 with part of the vaccinia virus early/late H6 promoter (positions −1 to −21, Perkus et al., 1989) creating DEN16 (containing DEN nucleotides 20–59, EcoRV site to −1 of the H6 promoter and DEN nucleotides 68–1447).

A SacI-XhoI fragment from DEN7 (nucleotides 1447–2579) was substituted for the corresponding region in DEN3 generating DEN19 containing DEN CDNA encoding the carboxy-terminal 64% E and amino-terminal 45% NS2A (nucleotides 1447–3745) with nucleotide 2467 present and the modified transcription termination signal (nucleotides 2448–2454). A XhoI-XbaI fragment from DEN19 (nucleotides 2579–3745) and a XbaI-HindIII fragment from DEN24 (XbaI nucleotide 3745 DEN through HindIII in IBI25) were ligated to XhoI-HindIII digested IBI25 creating DEN25 containing DEN cDNA encoding the carboxy-terminal 82% NS1, NS2A and amino-terminal 28% NS2B (nucleotides 2579–4213) with a EagI site at 4102, nucleotide 2467 present and mutagenized transcription termination signal (nucleotides 2448–2454). The XhoI-XbaI fragment from DEN19 (nucleotides 2579–3745) was ligated to XhoI (within IBI25) and XbaI (DEN nucleotide 3745) digested DEN21 creating DEN22 encoding the carboxy-terminal 82% NS1, NS2A, NS2B and amino-terminal 24 aa NS3 (nucleotides 2579–4564) with nucleotide 2467 present, modified transcription termination signal (nucleotides 2448–2454) and EagI site at 4492.

A HindIII-PstI fragment of DEN16 (nucleotides 20–59, EcoRV site to −1 of the H6 promoter and DEN nucleotides 68–494) was ligated to a HindIII-PstI fragment from DEN47 (encoding the carboxy-terminal 83% prM and amino-terminal 36% of E nucleotides 494–1447 and plasmid origin of replication) generating DEN17 encoding C, prM and amino-terminal 36% E with part of the H6 promoter and EcoRV site preceding the amino-terminus of C. A HindIII-BIII fragment from DEN17 encoding the carboxy-terminal 13 aa C, prM and amino--terminal 36% E (nucleotides 370–1447) was ligated to annealed oligonucleotides SP111 and SP112 (containing a disabled HindIII sticky end, EcoRV site to −1 of the H6 promoter, and DEN nucleotides 350–369 with a BglII sticky end) creating DEN33 encoding the EcoRV site to −1 of the H6 promoter, carboxy-terminal 20 aa C, prM and amino-terminal 36% E.

SmaI-EagI digested pTP15 (Mason et al., 1991) was ligated to a SmaI-SacI fragment from DEN4 encoding the carboxy-terminal 11 aa C, prM and amino-terminal 36% E (nucleotides 377–1447) and SacI-EagI fragment from DEN3 encoding the carboxy-terminal 64% E, NS1 and amino-terminal 45% NS2A generating DENL. The SacI-XhoI fragment from DEN7 encoding the carboxy-terminal 64% E and amino-terminal 18% NS1 (nucleotides 1447–2579) was ligated to a BstEII-SacI fragment from DEN47 (encoding the carboxy-terminal 55% prM and amino-terminal 36% E (nucleotides 631–1447) and a BstEII-XhoI fragment from DENL (containing the carboxy-terminal 11 aa C, amino-terminal 45% prM, carboxy-terminal 82% NS1, carboxy-terminal 45% NS2A, origin of replication and vaccinia sequences) generating DEN8. A unique SmaI site (located between the H6 promoter and ATG) was removed using oligonucleotide-directed double-strand break mutagenesis (Mandecki, 1986) creating DEN8VC in which the H6 promoter immediately preceded the ATG start codon.

An EcoRV-SacI fragment from DEN17 (positions −21 to −1 H6 promoter DEN nucleotides 68–1447) encoding C, prM and amino-terminal terminal 36% E) was ligated to an EcoRV-SacI fragment of DEN8VC (containing vaccinia sequences, H6 promoter from −21 to −124, origin of replication and amino-terminal 64% E, NS1, amino-terminal terminal 45% NS2A nucleotides 1447–3745) generating DEN18. A XhoI-EagI fragment from DEN25 encoding the carboxy-terminal 82% NS1 and NS2A (nucleotides 2579–4102) was ligated to an XhoI-EagI fragment of DEN18 (containing the origin of replication, vaccinia sequences and DEN C prM, E and amino-terminal 18% NS1 nucleotides 68–2579) generating DEN26. An EcoRV-SacI fragment from DEN8VC (positions −21 to −1 H6 promoter DEN nucleotides 377–1447 encoding 11aaC, prM and amino-terminal 36% E) was ligated to an EcoRV-SacI fragment of DEN26 (containing the origin of replication, vaccinia sequences and DEN region encoding the carboxy-terminal 64% E, NS1 and NS2A with a base missing in NS1 at nucleotide 2894) generating DEN32. DEN32 was transfected into vP410 infected cells to generate the recombinant vP867 (FIG. 21).

A SacI-XhoI fragment from DEN10 (nucleotides 1447–2579) was substituted for the corresponding region in DEN3 generating DEN11 containing DEN CDNA encoding the carboxy-terminal 64% E, NS1 and amino-terminal 45% NS2A with a SmaI site and ATG 15 aa from the carboxy-terminus of E. A SmaI-EagI fragment from DEN11 (encoding the carboxy-terminal 15 aa E, NS1 and amino-terminal 45% NS2A nucleotides 2348–3745) was ligated to SmaI-EagI digested pTP15 generating DEN12.

A XhoI-EagI fragment from DEN22 (nucleotides 2579–4492) was ligated to the XhoI-EagI fragment from DEN18 described above generating DEN27. An EcoRV-PstI fragment from DEN12 (positions −21 to −1 H6 promoter DEN nucleotides 2348–3447 encoding 15aaE, NS1) was ligated to an EcoRV-PstI fragment from DEN27 (containing the origin of replication, vaccinia sequences, H6 promoter −21 to −124 and DEN cDNA encoding NS2A and NS2B) generating DEN31.

An EcoRV-XhoI fragment from DEN8VC (positions −21 to −1 H6 promoter DEN nucleotides 377–2579 encoding the carboxy-terminal 11 aa C, prM E, amino-terminal 18% NS1) was ligated to an EcoRV-XhoI fragment from DEN31 (containing the origin of replication, vaccinia sequences and DEN cDNA encoding the carboxy-terminal 82% NS1, NS2A, NS2B with the base in NS1 at 2894) generating DEN35. DEN35 was transfected into vP410 infected cells generating the recombinant vP955 (FIG. 21). An EcoRV-SacI fragment from DEN33 (positions −21 to −1 H6 promoter DEN nucleotides 350–1447 encoding the carboxy-terminal 20 aa C, prM and amino-terminal 36% E) and a SacI-XhoI fragment from DEN32 (encoding the carboxy-terminal 64% E and amino-terminal 18% NS1 nucleotides 1447–2579) were ligated to the EcoRV-SacI fragment from DEN31 described above generating DEN34. DEN34 was transfected into vP410 infected cells generating the recombinant vP962 (FIG. 21). Oligonucleotides DEN 1 (SEQ ID NO:38), DEN 2 (SEQ ID NO:39), DEN9 (SEQ ID NO:40), DEN10 (SEQ ID NO:41), SP11 (SEQ ID NO:42), and SP112 (SEQ ID NO:43) are as follows:

```
DEN1   5'- CTAGA tga TTTTTAT CGGCCG A        -3'
DEN2   3'-       T ACT AAAAATA GCCGGC TTCGA  -5'
           XbaI              EagI    HindIII DEN9   5' AGCTT CCCGGG atg CTCCTCATGCTGCTGCCC
DEN10  3'       A GGGCCC TAC GAGGAGTACGACGACGGG
          HindIII  SmaI ACAGCCCTGGCGTTCCATCTGACCACCCGAG T         -3'
       TGTCGGGACCGCAAGGTAGACTGGTGGGCTC AGATC     -5'
                                        AvaI  XbaI -24            H6            -1
SP111  5' AGCT GATATCCGTTAAGTTTGTATCGTA atg AACAGGAGGAAA A    -3'
SP112  3'      A CTATAGGCAATTCAAACATAGCAT TAC TTGTCCTCCTTT TCTAG-5'
          HindIII EcoRV                                    BglII
```

Immune Response to the Recombinant Vaccinia Viruses

Groups of 3 week old mice were inoculated ip with $10^7$ pfu vaccinia recombinants vP962, vP955, vP867, vP452 (vaccinia control) or 100 μl of a 10% suspension of suckling mouse brain containing dengue type 1 Hawaii strain. Three weeks later sera were collected. One group of mice was re-inoculated and sera were collected 4 weeks later. Sera were assayed for HAI antibodies as described by Mason et al. (1991).

Table 12 shows that mice immunized twice with vP962 developed high levels of HAI antibodies, levels were equivalent to those obtained in animals immunized twice with Dengue type 1 Hawaii strain.

TABLE 12

| | HAI antibody titers | |
|---|---|---|
| Virus | One Immunization | Two Immunizations |
| vP452 | <1:10 | <1:10 |
| vP962 | 1:10 | 1:80 |
| vP955 | <1:10 | <1:10 |
| vP867 | <1:10 | 1:10 |
| DEN-1 | 1:40 | 1:80 |

Construction of Vaccinia Insertion Vector Containing DEN Type 1 20 aaC, prM, E

A 338bp fragment encoding the carboxy-terminal 23% E (nucleotides 2055–2392, Mason et al., 1987b) TGA stop codon T5NT vaccinia early transcription termination signal (Yuen et al., 1987) and EclXI and BamHI sites was derived by PCR (Engelke et al., 1988) using plasmid DEN7 as template and oligonucleotides (SEQ ID NO:58/SEQ ID NO:59)

```
SP122  5'-GTGAAAAAGCTTTGAAACTAAGCTGGTTC-3'
              HindIII
``` and

```
SP130  5'-5'-TCGGGATCCCGGCCGATAAAAATCACGCCTGAACCATGACTCCTAGGTAC-3'
              BamHI   EclXI
```

The PCR fragment was digested with HindIII (DEN nucleotide 2062, Mason et al., 1987b) and BamHI (follows the TGA, and T5NT and EclXI site) and cloned into HindIII/BamHI digested IBI25 generating DEN36. DEN34 was digested with EcoRV (within the H6 promoter) and HindIII within E (DEN nucleotide 2061; Mason et al., 1987b) and a 1733 bp fragment (containing EcoRV to −1 H6 promoter, 20 aaC, prM and amino-terminal 77% E) was isolated. DEN36 was digested with HindIII and EclXI and a 331 bp fragment isolated (containing DEN nucleotides 2062–2392 TGA T5NT EclXI sticky end). The 1733 bp fragment and 331 bp fragment were ligated to EcoRV/EclXI digested pT15 (Guo et al., 1989) generating plasmid DEN38. Plasmid DEN38 can be transfected into vaccinia infected cells to generate a recombinant encoding DEN 20 aaC, prM and E.

Example 14—CONSTRUCTION OF ALVAC RECOMBINANT EXPRESSING JEV PROTEINS

This example describes the development of canarypox recombinant vCP107 encoding JEV 15aaC, prM, E, NS1, NS2A and a canarypox donor plasmid (JEVCPC5) encoding 15aaC, prM, E.

Cells and Viruses

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of Canarypox Insertion Vector

Figure 23A:
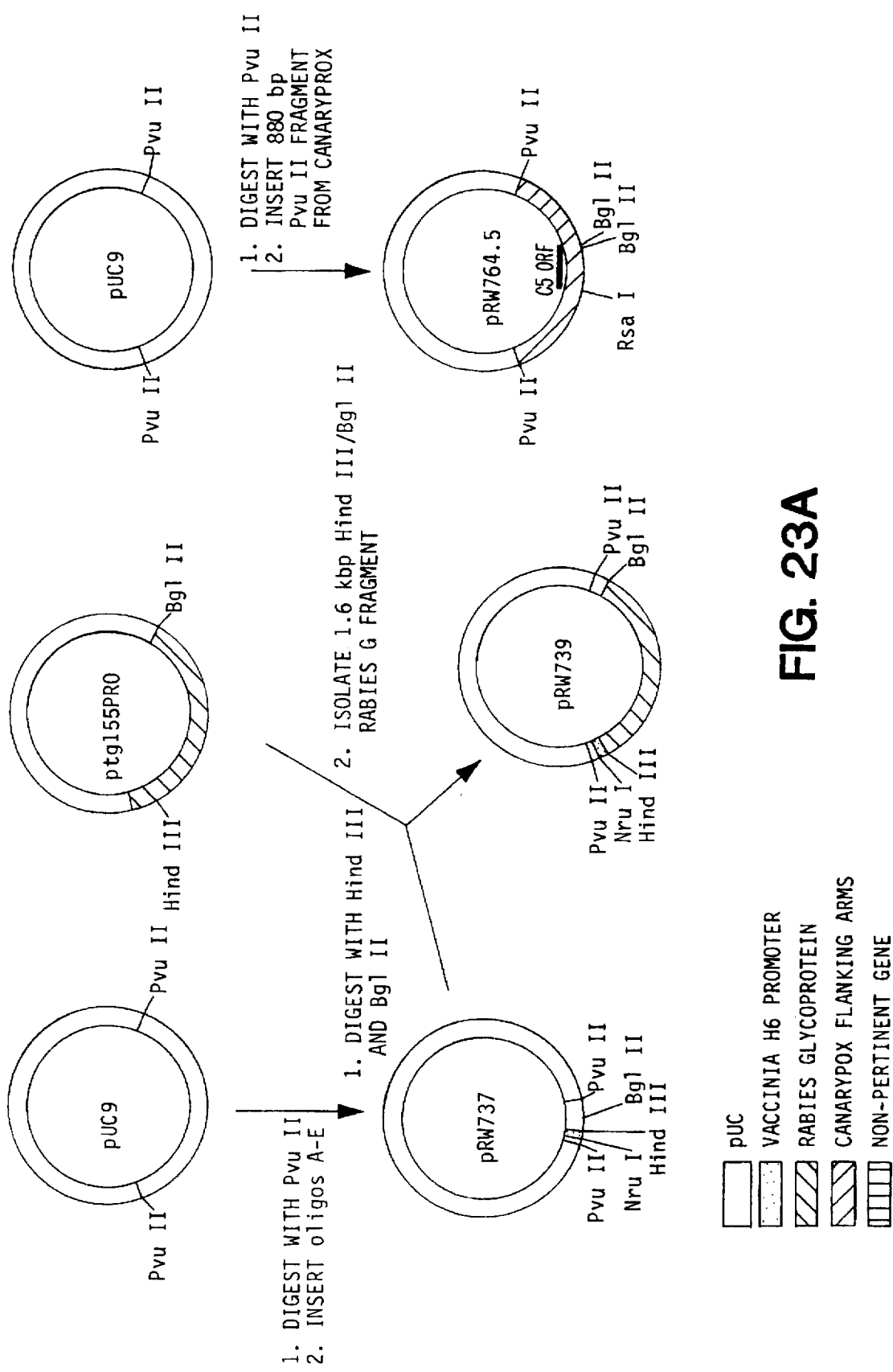
FIG. 23 schematically shows a method for the construction of plasmid pRW848 for deletion of C5.
Figure 23B:
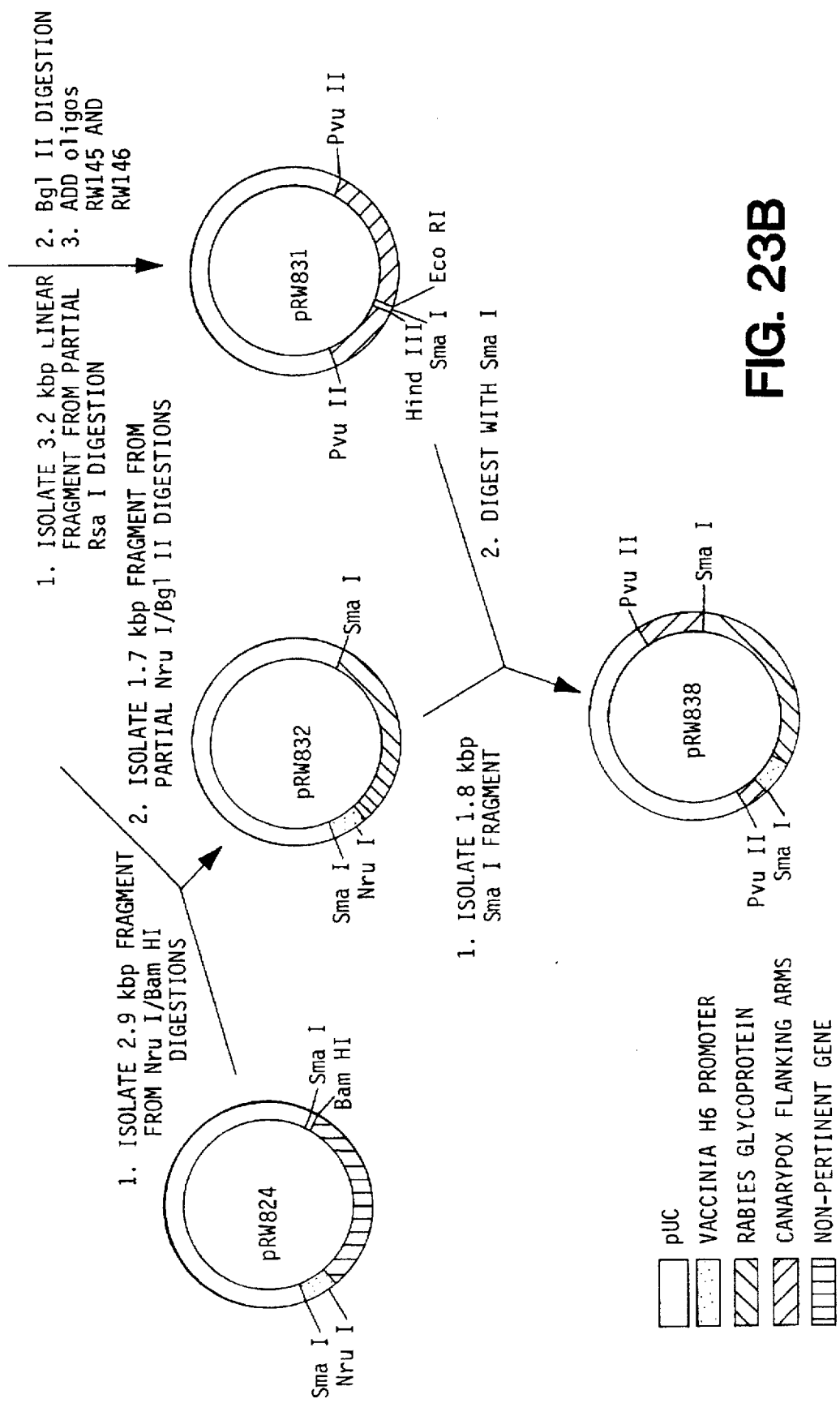

An 880 bp canarypox PvuII fragment was cloned between the PvuII sites of pUC9 to form pRW764.5. The sequence of this fragment is shown in FIG. 22 (SEQ ID NO:90) between positions 1372 and 2251. The limits of an open reading frame designated as C5 were defined. It was determined that the open reading frame was initiated at position 1537 within the fragment and terminated at position 1857. The C5 deletion was made without interruption of open reading frames. Bases from position 1538 through position 1836 were replaced with the sequence GCTTCCCGGGAATTCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below (FIG. 23). Plasmid pRW764.5 was partially cut with RsaI and the linear product was isolated. The RsaI linear fragment was recut with BglII and the pRW764.5 fragment now with a RsaI to BglII deletion from position 1527 to position 1832 was isolated and used as a vector for the following synthetic oligonucleotides:
RW145 (SEQ ID NO:60):
ACTCTCAAAAGCTTCCCGGGAAT-TCTAGCTAGCTAGTTTTTATAAA
RW146 (SEQ ID NO:61):
GATCTTTATAAAAACTAGCTAGCTA-GAATTCCCGGGAAGCTTTTGAGAGT Oligonucleotides RW145 (SEQ ID NO:60) and RW146 (SEQ ID NO:61) were annealed and inserted into the pRW 764.5 RsaI and BglII vector described above. The resulting plasmid is designated pRW831.

Construction of Insertion Vector Containing JEV 15aaC, prM, E, NS1, NS2A

Construction of pRW838 is illustrated below (FIG. 23). Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleoties A through E are:

nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

pRW838 was digested at the 3' end of the rabies glycoprotein gene with EcoRI filled in with the Klenow fragment of DNA polymerase I digested within the H6 promoter with EcoRV, and treated with alkaline phosphatase and a 3202 bp fragment containing the 5' 103 bp of the H6 promoter, plasmid origin of replication and C5 flanking arms isolated. Plasmid JEVL14VC containing JEV cDNA encoding 15 amino acids C, prM, E, NS1, NS2A in a vaccinia virus donor plasmid (FIG. 1) (nucleotides 337–4125, FIG. 17A and B) (SEQ ID NO:52) was digested with EcoRV in the H6 promoter and SacI in JEV sequences (nucleotide 2124) and a 1809 bp fragment isolated. JEVL14VC was digested with EclXI at the EagI site following the T5AT, filled in with the Klenow fragment of DNA polymerase I and digested with SacI in JEV sequences (nucleotide 2124) generating a 2011 bp fragment. The 1809 bp EcoRV-SacI, 2011 bp SacI-filled EclXI and 3202 bp EcpRV filled EcoRI fragments were ligated generating JEVCP1. JEVCP1 was transfected into ALVAC infected primary CEF cells to generate the canarypox recombinant vCP107 encoding 15 amino acids C, prM, E, NS1, NS2A (FIG. 18).

A (SEQ ID NO:62): CTGAAATTATTTCATTATCGCGATATCCGTTAAGTTT
GTATCGTAATGGTTCCTCAGGCTCTCCTGTTTGT

B (SEQ ID NO:63): CATTACGATACAAACTTAACGGATATCGCGATAATGAAAT
AATTTCAG

C (SEQ ID NO:64): ACCCCTTCTGGTTTTTCCGTTGTGTTTTGGGAAATT
CCCTATTTACACGATCCCAGACAAGCTTAGATCTCAG

D (SEQ ID NO:65): CTGAGATCTAAGCTTGTCTGGGATCGTGTAAATAGGGAAT
TTCCCAAAACA

E (SEQ ID NO:66): CAACGGAAAAACCAGAAGGGGTACCAAACAGGAGAGCCTGA
GGAAC

The diagram of annealed oligonucleotides A through E is as follows:

```
    A              C
---------------|---------------------
        ---|---------------|---------
    B          E          D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is: GGATCCCCGGG. pRW824 is a plasmid that contains a Construction of C5 Insertion Vector Containing JEV 15aac, prM, E A C5 insertion vector containing 1535 bp upstream of C5, polylinker containing KpnI/SmaI/XbaI and NotI sites and 404 bp of canarypox DNA (31 base pairs of C5 coding sequence and 473 bp of downstream sequence) was derived in the following manner. A genomic library of canarypox DNA was constructed in the cosmid vector puKlo2 (Knauf et al., 1982) probed with pRW764.5 and a clone containing a 29 kb insert identified (pHCOS1). A 3.3 kb ClaI fragment from pHCOS1 containing the C5 region was identified. Sequence analysis of the ClaI fragment was used to extend the sequence in FIG. 22 (SEQ ID NO:90) from nucleotides 1–1372.

The new C5 insertion vector was constructed in two steps. The 1535 bp upstream sequence was generated by PCR amplification (Engelke et al., 1988) using oligonucleotides C5A (SEQ ID NO:67) (5'-ATCATCGAATTCTGAATGTTAAATGTTATACTTTG-3') and C5B (SEQ ID NO:68) (5'-GGGGGTACCTTTGAGAGTACCACTTCAG-3') and purified genomic canarypox DNA as template. This fragment was digested with EcoRI (within oligoC5A) and cloned into EcoRI/SmaI digested pUC8 generating C5LAB. The 404 bp arm was generated by PCR amplification using oligonucleotides C5C (SEQ ID NO:69) (5'-

GGGTCTAGAGCGGCCGCTTATAAAGATCTAAAATG CATAATTTC-3') and C5DA (SEQ ID NO:70) (5'-ATCATCCTGCAGGTATTCTAAACTAGGAATAGATG-3'. This fragment was digested with PstI (within oligo C5DA) and cloned into SmaI/PstI digested C5LAB generating pC5L.

pC5L was digested within the polylinker with As 718 and NotI, treated with alkaline phosphatase and ligated to kinased and annealed oligonucleotides CP26 (SEQ ID NO:71) and CP27 (SEQ ID NO:72) (containing a disabled Asp718 site, translation stop codons in six reading frames, vaccinia early transcription termination signal (Yuen and Moss, 1987), BamHI KpnI XhoI XbaI ClaI and SmaI restriction sites, vaccinia early transcription termination signal, translation stop codons in six reading frames, and a disabled NotI site) generating plasmid C5LSP. The early/late H6 vaccinia virus promoter (Guo et al., 1989; Perkus et al., 1989) was derived by PCR (Engelke et al., 1988) using pRW824 as template and oligonucleotides CP30 (SEQ ID NO:73) (5'-TCGGGATCCGGGTTAATTAATTAGTCATCAGGCAG GGCG-3') and CP31 (SEQ ID NO:72) (5'-TAGCTCGAGGGTACCTACGATACAAACTTAACGGA TATCG-3'). The PCR product was digested with BamHI and XhoI (sites present at the 5' end of CP30 (SEQ ID NO:75) and CP31 (SEQ ID NO:74), respectively) and ligated to BamHI-XhoI digested C5LSP generating VQH6C5LSP. CP26 (SEQ ID NO:71) and CP27 (SEQ ID NO:72) are as follows:

```
CP26  5'-GTACGTGACTAATTAGCTATAAAAAGGATCCGGTACCCTCGAG
CP27  3'-   CACTGATTAATCGATATTTTTCCTAGGCCATGGGAGCTC
                          BamHI  KpnI  XhoI

TCTAGAATCGATCCCGGGTTTTTATGACTAGTTAATCAC    -3'
AGATCTTAGCTAGGGCCCAAAAATACTGATCAATTAGTGCCGG-5'
XbaI  ClaI  SmaI
```

Plasmid JEV36 was digested within the H6 promoter with EcoRV and within JEV sequences with SphI (nucleotide 2380) and a 2065 bp fragment isolated. Plasmid VQH6C5LSP was digested within the H6 promoter with EcoRV and within the polylinker with XbaI and ligated to the 2065 bp fragment plus annealed oligonucleotides SP131 (SEQ ID NO:75) and SP132 (SEQ ID NO:76) (containing a SphI sticky end, T nucleotide completing the E coding region, translation stop, a vaccinia early transcription termination signal (AT5AT; Yuen and Moss, 1987), a second translation stop, and XbaI sticky end) generating plasmid JEVCP5 which encodes 15 amino acids C, prM and E under the control of the H6 promoter between C5 flanking arms. JEVCP5 can be transfected in ALVAC or ALVAC recombinant infected cells to generate a recombinant encoding JEV 15 aa C, prM and E.

```
SP131
(SEQ ID NO:75) 5'-   C T tga tttttat tga T    -3'
SP132
(SEQ ID NO:76) 3'-GTACG A ACT AAAAATA ACT AGATC-5'
                 SphI                       XbaI
```

Example 15—CONSTRUCTION OF ALVAC RECOMBINANT EXPRESSING YFV PROTEINS

Construction of Canarypox Insertion Vector

An 8.5 kb canarypox BglII fragment was cloned in the BamHI site of pBS-SK plasmid vector to form pWW5. Nucleotide sequence analysis revealed a reading frame designated C3 initialed at position 1458 and terminated at position 2897 in the sequence in FIG. 24A–C (SEQ ID NO:83). In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:77) (5'-CAGTTGGTACCACTGGTATTTTATTTCAG-3') and RG278 (SEQ ID NO:78) (5'-TATCTGAATTCCTGCAGCCCGGGTTTTTATAGCTAAT TAGTCAAATGTGAGTTAATATTAG-3').

Primers for the 3' sequences were RG279 (SEQ ID NO:79) (5'TCGCTGAATTCGATATCAAGCTTATC GATTTTTATGACTAGTTAATCAAATAAAAAGCATAC AAGC-3') and RG280 (SEQ ID NO:80) (5'-TTATCGAGCTCTGTAACATCAGTA TCTAAC-3'). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

A 908 bp fragment of canarypox DNA, immediately upstream of the C3 locus (nucleotides 537–1444, FIG. 24A–C (SEQ ID NO:83)) was obtained by digestion of plasmid pWW5 with NsiI and SspI. A 604 bp fragment of canarypox and DNA (nucleotides 1–604, FIG. 24A–C (SEQ ID NO:83)) was derived by PCR (Engelke et al., 1988) using plasmid pWW5 as template and oligonucleotides CP16 (SEQ ID NO:81) (5'-TCCGGTACCGCGGCCGCAGA TATTTGTTAGCTTCTGC-3') and CP17 (SEQ ID NO:82) (5'-TCGCTCGAGTAGGATACCTACCTACTACCTACG-3'). The 604 bp fragment was digested with Asp718 and XhoI (sites present at the 5' ends of oligonucleotides CP16 and CP17, respectively) and cloned into Asp718-XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI (nucleotide 536, FIG. 24A–C (SEQ ID NO:83)) and ligated to the 908 bp NsiI-SspI fragment generating SPCPLAX which contains 1444 bp of canarypox DNA upstream of the C3 locus.

A 2178 bp BglII-StyI fragment of canarypox DNA (nucleotides 3035–5212, FIG. 24A–C (SEQ ID NO:83)) was isolated from plasmids pXX4 (which contains a 6.5 kb NsiI fragment of canarypox DNA cloned into the PstI site of pBS-SK. A 279 bp fragment of canarypox DNA (nucleotides 5194–5472, FIG. 24A–C SEQ ID NO:83)) was isolated by PCR (Engelke et al., 1988) using plasmid pXX4 as template and oligonucleotides CP19 (SEQ ID NO:84) (5'-TCGCTCGAGCTTTCTTGACAATAACATAG-3') and CP20 (SEQ ID NO:85) (5'-TAGGAGCTCTTTATAC TACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA.

To add additional unique sites to the polylinker, pC3I was digested within the polylinker region with EcoRI and ClaI, treated with alkaline phosphatase and ligated to kinased and annealed oligonucleotides CP12 (SEQ ID NO:86) and CP13 (SEQ ID NO:87) (containing an EcoRI sticky end, XhoI site, BamHI site and a sticky end compatible with ClaI) generating plasmid SPCP3S. SPCP3S was digested within the canarypox sequences downstream of the C3 locus with StyI (nucleotide 3035) and SacI (pBS-SK) and ligated to a 261 bp BglII-SacI fragment from SPC3RA (nucleotides 5212–5472, FIG. 24A–C (SEQ ID NO:83)) and the 2178 bp BglII-StyI fragment from pXX4 (nucleotides 3035–5212, FIG. 24A–C (SEQ ID NO:83)) generating plasmid CPRAL containing 2572 bp of canarypox DNA downstream of the C3 locus. SPCP3S was digested within the canarypox sequences upstream of the C3 locus with Asp718 (in pBS-SK) and AccI (nucleotide 1435) and ligated to a 1436 bp Asp718-AccI fragment from SPCPLAX generating plasmid CPLAL containing 1457 bp of canarypox DNA upstream of the C3 locus. CPLAL was digested within the canarypox sequences downstream of the C3 locus with StvI (nucleotide 3035) and SacI (in pBS-SK) and ligated to a 2438 bp StyI-SacI fragment from CPRAL generating plasmid CP3L containing 1457 bp of canarypox DNA upstream of the C3 locus, stop codons in six reading frames, early transcription termination signal, a polylinker region, early transcription termination signal, stop codons in six reading frames, and 2572 bp of canarypox DNA downstream of the C3 locus.

The early/late H6 vaccinia virus promoter (Guo et al., 1989; Perkus et al., 1989) was derived by PCR (Engelke et al., 1988) using pRW838 as template and oligonucleotides CP21 (SEQ ID NO:88) (5'-TCGGGATCCGGGTTAA TTAATTAGTTATTAGACAAGGTG-3') and CP22 (SEQ ID NO:89) (5'-TAGGAATTCCTCGAGTACGATACAA ACTTAAGCGGATATCG-3'). The PCR product was digested with BamHI and EcoRI (sites present at the 5' ends of oligonucleotides CP21 and Cp22, respectively) and ligated to CP3L that was digested with BamHI and EcoRI in the polylinker generating plasmid VQH6CP3L.

```
CP12  (SEQ ID NO:85)  5'-AATTCCTCGAGGGATCC    -3'
CP13  (SEQ ID NO:86)  3'-     GGAGCTCCCTAGGGC-5'
                      EcoRI  XhoI   BamHI
```

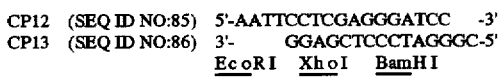

ALVAC donor plasmid VQH6CP3L was digested within the polylinker with XhoI and SmaI and ligated to a 3772 bp XhoI-SmaI fragment from YF51 (nucleotides 419–4180 encoding YF 21 amino acids C, prM, E, NS1, NS2A) generating YF52. The 6 bp corresponding to the unique XhoI site in UP52 were removed using oligonucleotide-directed double-strand break mutagenesis (Mandecki, 1986) creating YFCP3. YFCP3 was transfected into ALVAC infected primary CEF cells to generate the canarypox recombinant vCPI27 encoding 21 aa C, prM, E, NS1, NS2A (FIG. 19).

Construction of C3 Insertion Vector Containing YFV 21 aa C, prM, E

YP52 was digested with SmaI at the 3' end of the YF CDNA and ApaI (YF nucleotide 1604), a 8344 bp fragment isolated (containing the plasmid origin of replication, canarypox DNA and YF cDNA encoding 21 amino acids C, prM, and amino-terminal 57% E) and ligated to a ApaI to SmaI fragment from YF16 (nucleotides 1604–2452 containing the carboxy-terminal 43% E) generating YF54. The 6 bp corresponding to the unique XhoI site in YF54 were removed as described above creating YFCP4 containing YF cDNA encoding 21 amino acids C, prM, and E. YFCP4 can be transfected into ALVAC or ALVAC recombinant infected cells to generate a recombinant encoding YFV 21 aa C, prM, E.

REFERENCES

1. Alkhatib, G., and Briedis, D., Virol. 150, 479–490 (1986).

2. Bertholet, C., Drillien, R., and Wittek, R., Proc. Natl. Acad. Sci. 82, 2096–2100 (1985).

3. Brandt, W. E., J. Infect. Dis. 157, 1105–1111 (1988).

4. Bray, M., Zhao, B., Markoff, L., Eckels, K. H., Chanock, R. M., and Lai, C. -J., J. Virol. 63, 2853–2856 (1989).

5. Cane, P. A., and Gould, E. A., J. Gen. Virol. 70, 557–564 (1989).

6. Clarke, D. H., and Casals, J., An. J. Trop., Med. Hyg. 7, 561–573 (1958).

7. Clewell, D. B., J. Bacteriol 110, 667–676 (1972).

8. Clewell, D. B. and Helinski, D. R., Proc. Natl. Acad. Sci. USA 62, 1159–1166 (1969).

9. Colinas, R. J., Condit, R. C., and Paoletti, E., Virus Research 18, 49–70 (1990).

10. D'Alessio, J. M., and Gerrard, G. F., Nucleic Acids Res. 16, 1999–2014 (1988).

11. Deubel, V., Kinney, R. M., Esposito, J. J., Cropp, C. B., Vorndam, A. V., Monath, T. P., and Trent, D., J. Gen. Virol. 69, 1921–1929 (1988).

12. Dubois, M. -F., Pourcel, C., Rousset, S., Chany, C., and Tiollais, P., Proc. Natl. Acad. Sci. USA 77, 4549–4553 (1980).

13. Eckels, K. H., Hetrick, F. M., and Russell, P. K. Infect. Immun. 11, 1053–1060 (1975).

14. Engelke, D. R., Hoener, P. A., and Collins, F. S., Proc. Natl. Acad. Sci. USA 85, 544–548 (1988).

15. Falgout, B., Chanock, R., and Lai, C. -J., J. Virol. 63, 1852–1860 (1989).

16. Fan, W., and Mason, P. W., Virol. 177, 470–476 (1990).

17. Gibson, C. A., Schlesinger, J. J., and Barrett, A. D. T. Vaccine 6, 7–9 (1988).

18. Goebel, S. J., Johnson, G. P., Perkus, M. E., Davis, S. W., Winslow, J. P., and Paoletti, E., Virology 179, 247–266 (1990a).

19. Goebel, S. J., Johnson, G. P., Perkus, M. E., Davis, S. W., Winslow, J. P., and Paoletti, E., Virology 179, 517–563 (1990b).

20. Gould, E. A., Buckley, A., Barrett, A. D. T., and Cammack, N., J. Gen. Virol. 67, 591–595 (1986).

21. Guo, P., Goebel, S., Davis, S., Perkus, M. E., Taylor, J., Norton, E., Allen, G., Lanquet, B., Desmettre P., and Paoletti, E., J. Virol. 64, 2399–2406 (1990).

22. Guo, P., Goebel, S., Davis, S., Perkus, M. E., Languet, B., Desmettre, P., Allen, G., and Paoletti, E., J. Virol. 63, 4189–4198 (1989).

23. Haishi, S., Imai, H., Hirai, K., Igarashi, A., and Kato, S., Acta Virol. 33, 497–503 (1989).

24. Henchal, E. A., Henchal, L. S., and Schlesinger J. J., J. Gen. Virol. 69, 2101–2107 (1988).

25. Huang, C. H., Advances in Virus Research 27, 71–101 (1982).

26. Kaufman, B. M., Summers, P. L., Dubois, D. R., Cohen, W. H., Gentry, M. K., Timchak R. L., Burke, D. S., and Eckels, K. H., Am. J. Trop. Med. Hyg. 41, 576–580 (1989).

27. Kaufman, B. M., Summers, P. L., Dubois, D. R., and Eckels, K. H., Am. J. Trop. Med. Hyg. 36, 427–434 (1987).

28. Kieny, M. P., Lathe, R., Drillien, R., Spehner, D., Skory, S., Schmitt, P., Wiktor, T., Koprowski, H., and Lecocq, J. P., Nature (London) 312, 163–166 (1984).

29. Kimura-Kuroda, J., and Yasui, K., J. Immunol. 141, 3606–3610 (1988).

30. Knauf, V. C., and Nester, E. W., Plasmid 8, 45–54 (1982).

31. Kunkel, T. A., Proc. Natl. Acad. Sci. USA 82, 488–492 (1985).

32. Mandecki, W., Proc. Natl. Acad. Sci. USA 83, 7177–7181 (1986).

33. Maniatis, T., Fritsch, E. F., and Sambrook, J., Molecular Cloning, Cold Spring Harbor Laboratory, NY 545 pages (1986).

34. Mason, P. W., McAda, P. C., Dalrymple, J. M., Fournier, M. J., and Mason, T. L., Virol. 158, 361–372 (1987a).

35. Mason, P. W., McAda, P. C., Mason, T. L., and Fournier, M. J., Virol. 161, 262–267 (1987B).

36. Mason, P. W., Dalrymple, J. M., Gentry, M. K., McCown, J. M., Hoke, C. H., Burke, D. S., Fournier, M. J., and Mason, T. L., J. Gen. Virol. 70, 2037–2049 (1989).

37. Mason, P. W., Virol. 169, 354–364 (1989).

38. Mason, P. W., Pincus, S., Fournier, M. J., Mason, T. L., Shope, R. E., and Paoletti, E., Virol. 180, 294–305 (1991).

39. Matsuura, Y., Miyamoto, M., Sato, T., Morita, C., and Yasui, K., Virol. 173, 674–682 (1989).

40. McAda, P. C., Mason, P. W., Schmaljohn, C. S., Dalrymple, J. M., Mason, T. L., and Fournier, M. J., Virol. 158, 348–360 (1987).

41. Men, R., Bray, M., and Lai, C. J., J. Virol. 65, 1400–1407 (1991).

42. Monath, T. P., In "The Togaviridae and Flaviviridae", S. Schlesinger and M. J. Schlesinger, Eds., Plenum Press, New York/London, pp. 375–440 (1986).

43. Moriarty, A. M., Hoyer, B. H., Shih, J. W. -K., Gerin, J. L., and Hamer, D. H., Proc. Natl. Acad. Sci. USA 78, 2606–2610 (1981).

44. Nowak, T., Farber, P. M., Wengler, G. and Wengler, G., Virol. 169, 365–376 (1989).

45. Okayama, H., and Berg, P., Mol. Cell. Biol. 2, 161–170 (1982).

46. Panicali, D., and Paoletti, E., Proc. Natl. Acad. Sci. USA 79, 4927–4931 (1982).

47. Perkus, M. E., Goebel, S. J., Davis, S. W., Johnson, G. P., Limbach, K., Norton, E. K., and Paoletti, E., Virology 179, 276–286 (1990).

48. Perkus, M. E., Piccini, A., Lipinskas, B. R., and Paoletti, E., Science 229, 981–984 (1985).

49. Perkus, M. E., Limbach, K., and Paoletti, E., J. Virol. 63, 3829–3836 (1989).

50. Piccini, A., Perkus, M. E. and Paoletti, E., In Methods in Enzymology, Vol. 153, eds. Wu, R., and Grossman, L., (Academic Press) pp. 545–563 (1987).

51. Repik, P. M., Dalrymple, J. M., Brandt, W. E., McCown, J. M., and Russell, P. K., Am. J. Trop. Med. Hyg. 32, 577–589 (1983).

52. Rice, C. M., Lenches, E. M., Eddy, S. R., Shin, S. J., Sheets, R. L., and Strauss, J. H., Science 229, 726–733 (1985).

53. Ruiz-Linares, A., Cahour, A., Despres, P., Girard, M., and Bouloy, M., J. Virol. 63, 4199–4209 (1989).

54. Russell, P. K., Brandt, W. E., and Dalrymple, J. M. In "The Togaviruses", R. W. Schlesinger, Ed., Academic Press, New York/London 18, 503–529 (1980).

55. Sanger, F., Nicklen, S., and Coulson, A. R., Proc. Natl. Acad. Sci. USA 74, 5463–5467 (1977).

56. Schlesinger, J. J., Brandriss, M. W., Cropp, C. B., and Monath, T. P., J. Virol. 60, 1153–1155 (1986).

57. Schlesinger, J. J., Brandriss, M. W., and Walsh, E. E., J. Immunol. 135, 2805–2809 (1985).

58. Schlesinger, J. J., Brandriss, M. W., and Walsh, E. E., J. Gen. Virol. 68, 853–857 (1987).

59. Shapira, S. K., Chou, J., Richaud, F. V. and Casadaban, M. J., Gene 25, 71–82 (1983).

60. Shapiro, D., Brandt, W. E., and Russell, P. K., Virol. 50, 906–911 (1972).

61. Shope, R. E., In "The Togaviruses", R. W. Schlesinger, ed., Academic Press, N.Y. pp. 47–82 (1980).

62. Tabor, S., and Richardson, C. C., Proc. Natl. Acad. Sci. USA 84, 4767–4771 (1987).

63. Taylor, J., Weinberg, R., Kawaoka, Y., Webster, R. G., and Paoletti, E., Vaccine 6, 504–508 (1988a).

64. Taylor, J., Weinberg, R., Languet, B., Desmettre, P., and Paoletti, E., Vaccine 6, 497–503 (1988b).

65. Taylor, J., Pincus, S., Tartaglia, J., Richardson, C., Alkhatib, G., Briedis, D., Appel, M., Norton, E., and Paoletti, E., J. Virol. 65, in press (1991).

66. Tesh, R. B., and Duboise, S. M., Am.-J. Trop. Med. Hyg. 36, 662–668 (1987).

67. Tiollais, P., Pourcel, C., and Dejean, A., Nature 317, 489–495 (1985).

68. Wengler, G., and Wengler, G., J. Virol. 63, 2521–2526 (1989a).

69. Wengler, G., and Wengler, G., J. Gen. Virol. 70, 987–992 (1989b).

70. Winkler, G., Randolph, V. B., Cleaves, G. R., Ryan, T. E., and Stollar, V., Virol. 162, 187–196 (1988).

71. Yasuda, A., Kimura-Kuroda, J., Ogimoto, M., Miyamoto, M., Sata, T., Sato, T., Takamura, C., Kurata, T., Kojima, A., and Yasui, K., J. Virol. 64, 2788–2795 (1990).

72. Yuen, L., and Moss, B., Proc. Natl. Acad. Sci. USA 84, 6417–6421 (1987).

73. Zhang, Y. -M., Hayes, E. P., McCarthy, T. C., Dubois, D. R., Summers, P. L., Eckels, K. H., Chanock, R. M., and Lai, C. -J., J. Virol. 62, 3027–3031 (1988).

74. Zhao, B., Prince, G., Horswood, R., Eckels, K., Summers, P., Chanock, R., and Lai, C. -J., J. Virol. 61, 4019–4022 (1987).

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:1:

TAATTAACTA GCTACCCGGG                                                                     20

( 2 ) INFORMATION FOR SEQ ID NO:2:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

AATTCCCGGG TAGCTAGTTA ATTACATG                                                            28

( 2 ) INFORMATION FOR SEQ ID NO:3:

( i ) SEQUENCE CHARACTERISTICS:
      ( A ) LENGTH: 73 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

AGCTTCCCGG GTAAGTAATA CGTCAAGGAG AAAACGAAAC GATCTGTAGT TAGCGGCCGC                          60

CTAATTAACT AAT                                                                            73

( 2 ) INFORMATION FOR SEQ ID NO:4:

( i ) SEQUENCE CHARACTERISTICS:
      ( A ) LENGTH: 69 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

ATTAGTTAAT TAGGCGGCCG CTAACTACAG ATCGTTTCGT TTTCTCCTTG ACGTATTACT                          60

TACCCGGGA                                                                                 69

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

TTAGTTAATT AGGCGGCCGC                                                                     20

( 2 ) INFORMATION FOR SEQ ID NO:6:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

CGATTACTAT GAAGGATCCG TT                                                                  22

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
AACGGATCCT TCATAGTAAT                                                    20
```

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CGATTACTAG ATCTGAGCTC CCCGGGCTCG AGGGATCCGT T                            41
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AACGGATCCC TCGAGCCCGG GGAGCTCAGA TCTAGTAAT                               39
```

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GATCCGAATT CTAGCT                                                        16
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGCTAGAATT CG                                                            12
```

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TATGAGTAAC TTAACTCTTT TGTTAATTAA AAGTATATTC AAAAAATAAG TTATATAAAT         60

AGATCTGAAT TCGTT                                                         75
```

( 2 ) INFORMATION FOR SEQ ID NO:13:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
AACGAATTCA  GATCTATTTA  TATAACTTAT  TTTTGAATA  TACTTTTAAT  TAACAAAAGA         60

GTTAAGTTAC  TCA                                                              73
```

( 2 ) INFORMATION FOR SEQ ID NO:14:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAAATGGGCG  TGGATTGTTA  ACTTTATATA  ACTTATTTTT  TGAATATAC                    49
```

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ACACGAATGA  TTTCTAAAG  TATTGGAAA  GTTTATAGG  TAGTTGATAG  AACAAAATAC          60

ATAATTT                                                                      67
```

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TCTATCAACT  ACCTATAAAA  CTTTCCAAAT  ACTTTAGAAA  ATCATTCGTG  T                51
```

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
TGTAAAAATA  AATCACTTTT  TATACTAAGA  TCTCCCGGGC  TGCAGC                       46
```

( 2 ) INFORMATION FOR SEQ ID NO:18:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GGCCGCTGCA GCCCGGGAGA TCTTAGTATA AAAAGTGATT TATTTTTACA AAATTATGTA        60

TTTTGT                                                                   66
```

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
TTTCTGTATA TTTGCACCAA TTTAGATCTT ACTCAAAATA TGTAACAATA                   50
```

( 2 ) INFORMATION FOR SEQ ID NO:20:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
TGTCATTTAA CACTATACTC ATATTAATAA AATAATATT TATT                          44
```

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GATCCTGAGT ACTTTGTAAT ATAATGATAT ATATTTCAC TTTATCTCAT TTGAGAATAA         60

AAAGATCTTA GG                                                            72
```

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AATTCCTAAG ATCTTTTTAT TCTCAAATGA GATAAAGTGA AAATATATAT CATTATATTA        60

CAAAGTACTC AG                                                            72
```

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GATCCAGATC TCCCGGGAAA AAAATTATTT AACTTTCAT TAATAGGGAT TTGACGTATG         60

TAGCGTACTA GG                                                            72
```

( 2 ) INFORMATION FOR SEQ ID NO:24:

( i ) SEQUENCE CHARACTERISTICS:
        ( A ) LENGTH: 72 base pairs ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCCTAGT ACGCATCATA CGTCAAATCC CTATTAATGA AAAGTTAAAT AATTTTTTC    60

CCGGGAGATC TG    72

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

TCGAGCCCGG GATGACTAAA AAACCAGGAG GGCC    34

( 2 ) INFORMATION FOR SEQ ID NO:26:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CTCCTGGTTT TTTAGTCATC CCGGGC    26

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CTTGATTTTT ATTGACGGCC GA    22

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

AGCTTCGGCC GTCAATAAAA ATCAAGCATG    30

( 2 ) INFORMATION FOR SEQ ID NO:29:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGGATGGGCG TTAACGCACG AGACCGATCA ATTGCTTTGG CCTTCTTAGC CACAGGAGGT    60

GTGCTCGTGT TCTTAGCGAC CAATGTGCAT G    91

( 2 ) INFORMATION FOR SEQ ID NO:30:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

```
CACATTGGTC GCTAAGAACA CGAGCACACC TCCTGTGGCT AAGAAGGCCA AAGCAATTGA        60
TCGGTCTCGT GCGTTAACGC CCATCCC                                           87
```

( 2 ) INFORMATION FOR SEQ ID NO:31:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
AGCTTCTTTA TTCTATACTT AAAAAGTGAA AATAAATACA AAGGTTCTTG AGGGT             55
```

( 2 ) INFORMATION FOR SEQ ID NO:32:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
TGTGTTAAAT TGAAAGCGAG AAATAATCAT AAATTATTTC ATTATCGCGA TATCCGTTAA        60
GTTTGTATCG TAC                                                          73
```

( 2 ) INFORMATION FOR SEQ ID NO:33:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
TCGAGTACGA TACAAACTTA ACGGATATCG CGATAATGAA ATAATTTATG ATTATT           56
```

( 2 ) INFORMATION FOR SEQ ID NO:34:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
TCTCGCTTTC AATTTAACAC AACCCTCAAG AACCTTTGTA TTTATTTTCA CTTTTTAAGT        60
ATAGAATAAA GA                                                           72
```

( 2 ) INFORMATION FOR SEQ ID NO:35:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

```
TTCTTCTTCT TGT                                                          13
```

( 2 ) INFORMATION FOR SEQ ID NO:36:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

```
AGCTTCTCGA GCATCGATTA CTATGTCTGG TCGTAAAGCT CAGGGAAAAA CCCTGGGCGT        60

CAATATGGT                                                                69
```

( 2 ) INFORMATION FOR SEQ ID NO:37:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

```
ACCATATTGA CGCCCAGGGT TTTCCCTGA GCTTACGAC CAGACATAGT AATCGATGCT          60

CGAGA                                                                    65
```

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

```
CTAGATGATT TTTATCGGCC GA                                                 22
```

( 2 ) INFORMATION FOR SEQ ID NO:39:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
AGCTTCGGCC GATAAAAATC AT                                                 22
```

( 2 ) INFORMATION FOR SEQ ID NO:40:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
AGCTTCCCGG GATGCTCCTC ATGCTGCTGC CCACAGCCCT GGCGTTCCAT CTGACCACCC        60

GAGT                                                                     64
```

( 2 ) INFORMATION FOR SEQ ID NO:41:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

CTAGACTCGG GTGGTCAGAT GGAACGCCAG GGCTGTGGGC AGCAGCATGA GGAGCATCCC    60

GGGA    64

( 2 ) INFORMATION FOR SEQ ID NO:42:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

AGCTGATATC CGTTAAGTTT GTATCGTAAT GAACAGGAGG AAAA    44

( 2 ) INFORMATION FOR SEQ ID NO:43:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

GATCTTTTCC TCCTGTTCAT TACGATACAA ACTTAACGGA TATCA    45

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

TGATTTTTAT CGGCCGA    17

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

AGCTTCGGCC GATAAAAATC A    21

( 2 ) INFORMATION FOR SEQ ID NO:46:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

TCGAGCCCGG GATGTGGCTC GCGAGCTTGG CAGTTGTCAT AGCCTGCGCA GGAGCCATGA    60

AGTTGTCAAA TTTCCAGGGG A    81

( 2 ) INFORMATION FOR SEQ ID NO:47:

( i ) SEQUENCE CHARACTERISTICS:
        ( A ) LENGTH: 81 base pairs
        ( B ) TYPE: nucleic acid (C) STRANDEDNESS: single
(D) TOPOLOGY: linear (xi) SEQUENCE DESCRIPTION: SEQ ID NO:47:

AGCTTCCCCT GGAAATTTGA CAACTTCATG GCTCCTGCGC AGGCTATGAC AACTGCCAAG    60

CTCGCGAGCC ACATCCCGGG C    81

(2) INFORMATION FOR SEQ ID NO:48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:48:

GATCCATGCA TTCTAGAC    18

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:49:

CATGGTCTAG AATGCATG    18

(2) INFORMATION FOR SEQ ID NO:50:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:50:

AGCTTCCCGG GATGCTTGGC AGTAACAACG GTC    33

(2) INFORMATION FOR SEQ ID NO:51:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:51:

GACCGTTGTT ACTGCCAAGC ATCCCGGGA    29

(2) INFORMATION FOR SEQ ID NO:52:

(i) SEQUENCE CHARACTERISTICS:
        (A) LENGTH: 4512 base pairs
        (B) TYPE: nucleic acid
        (C) STRANDEDNESS: single
        (D) TOPOLOGY: linear (xi) SEQUENCE DESCRIPTION: SEQ ID NO:52:

ATGACTAAAA AACCAGGAGG GCCCGGTAAA AACCGGGCTA TCAATATGCT GAAACGCGGC    60

TTACCCCGCG TATTCCCACT AGTGGGAGTG AAGAGGGTAG TGATGAGCTT GTTGGACGGG    120

AGAGGGCCAG TACGTTTCGT GCTGGCTCTT ATCACGTTCT TCAAGTTTAC AGCATTAGCC    180

CCGACCAAGG CGCTTTTAGG CCGATGGAAA GCAGTGGAAA AGAGTGTGGC AATGAAACAT    240

| | | | | | |
|---|---|---|---|---|---|
|CTTACTAGTT|TCAAACGAGA|ACTCGGAACA|CTCATTGACG|CCGTGAACAA|GCGGGGCAGA|300|
|AAGCAAAACA|AAAGAGGAGG|AAATGAAGGC|TCAATCATGT|GGCTCGCGAG|CTTGGCAGTT|360|
|GTCATAGCCT|GCGCAGGAGC|CATGAAGTTG|TCAAATTTCC|AGGGGAAGCT|TTTGATGACC|420|
|GTCAACAACA|CGGACATTGC|AGACGTTATC|GTGATTCCCA|CCTCAAAAGG|AGAGAACAGA|480|
|TGTTGGGTCC|GGGCAATCGA|CGTCGGCTAC|ATGTGTGAGG|ACACTATCAC|GTACGAATGT|540|
|CCTAAGCTCA|CCATGGGCAA|TGATCCAGAG|GACGTGGACT|GTTGGTGTGA|CAACCAAGAA|600|
|GTCTACGTCC|AATATGGACG|GTGCACGCGG|ACCAGGCATT|CCAAGCGAAG|CAGGAGATCC|660|
|GTGTCGGTCC|AAACACATGG|GGAGAGTTCA|CTAGTGAATA|AAAAGAGGC|TTGGCTGGAT|720|
|TCAACGAAAG|CCACACGATA|CCTCATGAAA|ACTGAGAACT|GGATCGTAAG|GAATCCTGGC|780|
|TATGCTTTCC|TGGCGGCGAT|ACTTGGCTGG|ATGCTTGGCA|GTAACAACGG|TCAACGCGTG|840|
|GTATTCACCA|TCCTCCTGCT|GTTGGTCGCT|CCGGCTTACA|GTTCAACTG|TCTGGGAATG|900|
|GGCAATCGTG|ACTTCATAGA|AGGAGCCAGT|GGAGCCACTT|GGGTGGACTT|GGTGCTAGAA|960|
|GGAGACAGCT|GCTTGACAAT|TATGGCAAAC|GACAAACCAA|CATTGGACGT|CCGCATGATC|1020|
|AACATCGAAG|CTGTCCAACT|TGCTGAGGTC|AGAAGTTACT|GCTATCATGC|TTCAGTCACT|1080|
|GACATTTCGA|CGGTGGCTCG|GTGCCCCACG|ACTGGAGAAG|CTCACAACGA|GAAGCGAGCT|1140|
|GATAGTAGCT|ATGTGTGCAA|ACAAGGCTTC|ACTGATCGTG|GGTGGGGCAA|CGGATGTGGA|1200|
|CTTTTCGGGA|AGGGAAGCAT|TGACACATGT|GCAAAATTCT|CCTGCACCAG|TAAGGCGATT|1260|
|GGGAGAACAA|TCCAGCCAGA|AAACATCAAA|TACGAAGTTG|GCATTTTGT|GCATGGAACC|1320|
|ACCACTTCGG|AAAACCATGG|GAATTATTCA|GCGCAAGTTG|GGCGTCCCA|GGCGGCAAAG|1380|
|TTTACAGTAA|CACCCAATGC|TCCTTCGATA|ACCCTTAAAC|TTGGTGACTA|CGGAGAAGTC|1440|
|ACACTGGACT|GTGAGCCAAG|GAGTGGACTA|AACACTGAAG|CGTTTTACGT|CATGACCGTG|1500|
|GGGTCAAAGT|CATTTTTGGT|CCACAGGGAA|TGGTTTCATG|ATCTCGCTCT|CCCTTGGACG|1560|
|CCCCCTTCGA|GCACAGCGTG|GAGAAACAGA|GAACTCCTCA|TGGAATTTGA|AGAGGCGCAC|1620|
|GCCACAAAAC|AGTCCGTTGT|TGCTCTTGGG|TCACAGGAAG|GAGGCCTCCA|TCAGGCGTTG|1680|
|GCAGGAGCCA|TCGTGGTGGA|GTACTCAAGC|TCAGTGAAGT|TAACATCAGG|CCACCTAAAA|1740|
|TGCAGGCTGA|AAATGGACAA|ACTGGCTCTG|AAAGGCACAA|CCTATGGCAT|GTGCACAGAA|1800|
|AAATTCTCGT|TCGCGAAAAA|TCCGGCGGAC|ACTGGTCACG|GAACAGTTGT|CATTGAACTT|1860|
|TCCTACTCTG|GGAGTGATGG|CCCTTGCAAA|ATTCCGATTG|TCTCCGTTGC|GAGCCTCAAT|1920|
|GACATGACCC|CCGTCGGGCG|GCTGGTGACA|GTGAACCCCT|TCGTCGCGAC|TTCCAGCGCC|1980|
|AACTCAAAGG|TGCTAGTCGA|GATGGAACCC|CCCTTCGGAG|ACTCCTACAT|CGTAGTTGGA|2040|
|AGGGGAGACA|AGCAGATTAA|CCACCATTGG|CACAAGGCTG|GAAGCACGCT|GGGCAAAGCC|2100|
|TTTTCAACGA|CTTTGAAGGG|AGCTCAAAGA|CTGGCAGCGT|GGGCGACAC|AGCCTGGGAC|2160|
|TTTGGCTCTA|TTGGAGGGGT|TTTCAACTCC|ATAGGGAAAG|CCGTTCACCA|AGTGTTTGGT|2220|
|GGTGCCTTCA|GAACACTCTT|CGGGGGAATG|TCTTGGATCA|CACAAGGGCT|AATGGGGGCC|2280|
|CTACTACTCT|GGATGGGCGT|TAACGCACGA|GACCGATCAA|TTGCTTTGGC|CTTCTTAGCC|2340|
|ACAGGAGGTG|TGCTCGTGTT|CTTAGCGACC|AATGTGCATG|CTGACACTGG|ATGTGCCATT|2400|
|GACATCACAA|GAAAAGAGAT|GAGGTGTGGA|AGTGGCATCT|TCGTGCACAA|CGACGTGGAA|2460|
|GCCTGGGTGG|ATAGGTATAA|ATATTTGCCA|GAAACGCCCA|GATCCCTGGC|GAAGATCGTC|2520|
|CACAAAGCGC|ACAAGGAAGG|CGTGTGCGGA|GTCAGATCTG|TCACCAGACT|GGAGCACCAA|2580|
|ATGTGGGAAG|CCGTACGGGA|CGAATTGAAC|GTCCTACTCA|AAGAGAACGC|AGTGGACCTC|2640|

-continued

| | | | | | |
|---|---|---|---|---|---|
| AGCGTGGTGG | TGAACAAGCC | CGTGGGGAGA | TATCGCTCAG | CCCCTAAACG | CCTATCCATG | 2700 |
| ACGCAAGAGA | AGTTTGAAAT | GGGCTGGAAA | GCATGGGGAA | AAAGCATTCT | CTATGCCCCG | 2760 |
| GAATTGGCTA | ACTCCACATT | TGTCGTAGAT | GGACCTGAGA | CAAAGGAATG | CCCTGATGAG | 2820 |
| CACAGAGCTT | GGAACAGCAT | GCAAATCGAA | GACTTCGGCT | TTGGCATCAC | ATCAACCCGT | 2880 |
| GTGTGGCTGA | AGATCAGAGA | GGAGAGCACT | GACGAGTGTG | ATGGAGCGAT | CATAGGCACG | 2940 |
| GCTGTCAAAG | GACATGTGGC | AGTCCATAGT | GACTTGTCGT | ACTGGATTGA | GAGTCGCTAC | 3000 |
| AACGACACAT | GGAAACTTGA | GAGGGCAGTC | TTTGGAGAGG | TCAAATCTTG | CACTTGGCCA | 3060 |
| GAGACACACA | CCCTTTGGGG | AGATGGTGTT | GAGGAAAGTG | AACTCATCAT | TCCGCATACC | 3120 |
| ATAGCCGGAC | CAAAAAGCAA | GCACAATCGG | AGGGAAGGGT | ATAAGACACA | AAACCAGGGA | 3180 |
| CCCTGGGACG | AGAATGGTAT | AGTCTTGGAC | TTTGATTATT | GCCCAGGGAC | AAAAGTCACC | 3240 |
| ATTACAGAGG | ATTGTGGCAA | GAGAGGCCCT | TCGGTCAGAA | CCACTACTGA | CAGTGGAAAG | 3300 |
| TTGATCACTG | ACTGGTGCTG | TCGCAGTTGC | TCCCTTCCGC | CCCTACGATT | CCGGACAGAA | 3360 |
| AATGGCTGCT | GGTACGGAAT | GGAAATCAGA | CCTGTCAGGC | ATGATGAAAC | AACACTCGTC | 3420 |
| AGATCACAGG | TTGATGCTTT | TAATGGTGAA | ATGGTTGACC | CTTTTCAGCT | GGGCCTTCTG | 3480 |
| GTGATGTTTC | TGGCCACCCA | GGAGGTCCTT | CGCAAGAGGT | GGACGGCCAG | ATTGACTATT | 3540 |
| CCCGCGGTTT | TGGGGCCCCT | ACTTGTGCTG | ATGCTTGGGG | GCATCACTTA | CACTGATTTG | 3600 |
| GCGAGGTATG | TGGTGCTAGT | CGCTGCTGCT | TTCGCAGAAG | CCAACAGTGG | AGGAGACGTC | 3660 |
| CTGCACCTTG | CTTTGATTGC | CGTTTTTAAG | ATCCAACCAG | CATTTCTAGT | GATGAACATG | 3720 |
| CTTAGCACGA | GATGGACGAA | CCAAGAAAAC | GTGGTTCTGG | TCCTAGGGGC | TGCCTTTTTT | 3780 |
| CAATTAGCCT | CAGTAGATCT | GCAAATAGGA | GTCCACGGAA | TCCTGAATGC | CGCCGCTATA | 3840 |
| GCATGGATGA | TTGTCCGAGC | GATCACTTTC | CCCACAACCT | CCTCCGTCAC | CATGCCAGTC | 3900 |
| TTAGCGCTTC | TAACTCCGGG | AATGAGGGCT | CTATACCTAG | ACACTTACAG | AATCATCCTC | 3960 |
| CTCGTCATAG | GGATTTGCTC | CCTGCTGCAA | GAGAGGAAAA | AGACCATGGC | AAAAAAGAAA | 4020 |
| GGAGCTGTAC | TCTTGGGCTT | AGCGCTCACA | TCCACTGGAT | GGTTCTCGCC | CACCACTATA | 4080 |
| GCTGCCGGAC | TAATGGTCTG | CAACCCAAAC | AAGAAGAGAG | GGTGGCCAGC | TACTGAGTTT | 4140 |
| TTGTCGGCAG | TTGGATTGAT | GTTTGCCATC | GTAGGTGGTT | TGGCCGAGTT | GGATATTGAA | 4200 |
| TCCATGTCAA | TACCCTTCAT | GCTGGCAGGT | CTTATGGCAG | TGTCCTACGT | GGTGTCAGGA | 4260 |
| AAAGCAACAG | ATATGTGGCT | TGAACGGGCC | GCCGACATCA | GCTGGGAGAT | GGATGCTGCA | 4320 |
| ATCACAGGAA | GCAGTCGGAG | GCTGGATGTG | AAGCTGGATG | ATGACGGAGA | TTTTCACTTG | 4380 |
| ATTGATGATC | CCGGTGTTCC | ATGGAAGGTC | TGGGTCTTGC | GCATGTCTTG | CATTGGCTTA | 4440 |
| GCCGCCCTCA | CGCCTTGGGC | CATTGTTCCC | GCCGCTTTTG | GTTATTGGCT | CACTTTAAAA | 4500 |
| ACAACAAAAA | GA | | | | | 4512 |

(2) INFORMATION FOR SEQ ID NO:53:

(i) SEQUENCE CHARACTERISTICS:
        (A) LENGTH: 2786 base pairs
        (B) TYPE: nucleic acid
        (C) STRANDEDNESS: single
        (D) TOPOLOGY: linear (xi) SEQUENCE DESCRIPTION: SEQ ID NO:53:

| | | | | | |
|---|---|---|---|---|---|
| AGATCTTGCA | CGTTACCCCC | CCTACGTTTC | AAAGGAGAAG | ACGGGTGCTG | GTACGGCATG | 60 |
| GAAATCAGAC | CAGTCAAGGA | GAAGGAAGAG | AACCTAGTTA | AGTCAATGGT | CTCTGCAGGG | 120 |
| TCAGGAGAAG | TGGACAGTTT | TTCACTAGGA | CTGCTATGCA | TATCAATAAT | GATCGAAGAG | 180 |

```
GTAATGAGAT  CCAGATGGAG  CAGAAAAATG  CTGATGACTG  GAACATTGGC  TGTGTTCCTC   240
CTTCTCACAA  TGGGACAATT  GACATGGAAT  GATCTGATCA  GGCTATGTAT  CATGGTTGGA   300
GCCAACGCTT  CAGACAAGAT  GGGGATGGGA  ACAACGTACC  TAGCTTTGAT  GGCCACTTTC   360
AGAATGAGAC  CAATGTTCGC  AGTCGGCTA   CTGTTCGCA   GATTAACATC  TAGAGAAGTT   420
CTTCTTCTTA  CAGTTGGATT  GAGTCTGGTG  GCATCTGTAG  AACTACCAAA  TTCCTTAGAG   480
GAGCTAGGGG  ATGGACTTGC  AATGGGCATC  ATGATGTTGA  AATTACTGAC  TGATTTTCAG   540
TCACATCAGC  TATGGGCTAC  CTTGCTGTCT  TTAACATTTG  TCAAAACAAC  TTTTTCATTG   600
CACTATGCAT  GGAAGACAAT  GGCTATGATA  CTGTCAATTG  TATCTCTCTT  CCCTTTATGC   660
CTGTCCACGA  CTTCTCAAAA  ACAACATGG   CTTCCGGTGT  TGCTGGGATC  TCTTGGATGC   720
AAACCACTAA  CCATGTTTCT  TATAACAGAA  AACAAAATCT  GGGGAAGGAA  AAGCTGGCCT   780
CTCAATGAAG  GAATTATGGC  TGTTGGAATA  GTTAGCATTC  TTCTAAGTTC  ACTTCTCAAG   840
AATGATGTGC  CACTAGCTGG  CCCACTAATA  GCTGGAGGCA  TGCTAATAGC  ATGTTATGTC   900
ATACCTGGAA  GCTCGGCCGA  TTTATCACTG  GAGAAAGCGG  CTGAGGTCTC  CTGGGAAGAA   960
GAAGCAGAAC  ACTCTGGTGC  CTCACACAAC  ATACTAGTGG  AGGTCCAAGA  TGATGGAACC  1020
ATGAAGATAA  AGGATGAAGA  GAGAGATGAC  ACACTCACCA  TTCTCCTCAA  AGCAACTCTG  1080
CTAGCAATCT  CAGGGGTATA  CCCAATGTCA  ATACCGGCGA  CCCTCTTTGT  GTGGTATTTT  1140
TGGCAGAAAA  AAAAACAGAG  ATCAGGAGTG  CTATGGGACA  CACCCAGCCC  TCCAGAAGTG  1200
GAAAGAGCAG  TCCTTGATGA  TGGCATTTAT  AGAATTCTCC  AAAGAGGATT  GTTGGGCAGG  1260
TCTCAAGTAG  GAGTAGGAGT  TTTTCAAGAA  GGCGTGTTCC  ACACAATGTG  GCACGTCACC  1320
AGGGGAGCTG  TCCTCATGTA  CCAAGGGAAG  AGACTGGAAC  CAAGTTGGGC  CAGTGTTAAA  1380
AAAGACTTGA  TCTCATATGG  AGGAGGTTGG  AGGTTTCAAG  GATCCTGGAA  CGCGGGAGAA  1440
GAAGTGCAGG  TGATTGCTGT  TGAACCGGGG  AAGAACCCCA  AAAATGTACA  GACAGCGCCG  1500
GGTACCTTCA  AGACCCCTGA  AGGCGAAGTT  GGAGCCATAG  CTCTAGACTT  TAAACCCGGC  1560
ACATCTGGAT  CTCCTATCGT  GAACAGAGAG  GGAAAAATAG  TAGGTCTTTA  TGGAAATGGA  1620
GTGGTGACAA  CAAGTGGTAC  CTACGTCAGT  GCCATAGCTC  AAGCTAAAGC  ATCACAAGAA  1680
GGGCCTCTAC  CAGAGATTGA  GGACGAGGTG  TTTAGGAAAA  GAAACTTAAC  AATAATGGAC  1740
CTACATCCAG  GATCGGGAAA  AACAAGAAGA  TACCTTCCAG  CCATAGTCCG  TGAGGCCATA  1800
AAAAGAAAGC  TGCGCACGCT  AGTCTTAGCT  CCCACAAGAG  TTGTCGCTTC  TGAAATGGCA  1860
GAGGCGCTCA  AGGGAATGCC  AATAAGGTAT  CAGACAACAG  CAGTGAAGAG  TGAACACACG  1920
GGAAAGGAGA  TAGTTGACCT  TATGTGTCAC  GCCACTTTCA  CTATGCGTCT  CCTGTCTCCT  1980
GTGAGAGTTC  CCAATTATAA  TATGATTATC  ATGGATGAAG  CACATTTCAC  CGATCCAGCC  2040
AGCATAGCAG  CCAGAGGGTA  TATCTCAACC  CGAGTGGGTA  TGGGTGAAGC  AGCTGCGATT  2100
TTCATGACAG  CCACTCCCCC  CGGATCGGTG  GAGGCCTTTC  CACAGAGCAA  TGCAGTTATC  2160
CAAGATGAGG  AAAGAGACAT  TCCTGAAAGA  TCATGGAACT  CAGGCTATGA  CTGGATCACT  2220
GATTTCCCAG  GTAAAACAGT  CTGGTTTGTT  CCAAGCATCA  AATCAGGAAA  TGACATTGCC  2280
AACTGTTTAA  GAAAGAATGG  GAAACGGGTG  GTCCAATTGA  GCAGAAAAAC  TTTTGACACT  2340
GAGTACCAGA  AAACAAAAAA  TAACGACTGG  GACTATGTTG  TCACAACAGA  CATATCCGAA  2400
ATGGGAGCAA  ACTTCCGAGC  CGACAGGGTA  ATAGACCCGA  GGCGGTGCCT  GAAACCGGTA  2460
ATACTAAAAG  ATGGCCCAGA  GCGTGTCATT  CTAGCCGGAC  CGATGCCAGT  GACTGTGTAC  2520
GCCGCCCAGA  GGAGAGGAAG  AATTGGAAGG  AACCAAAATA  GGAAGGCGA   TCAGTATATT  2580
```

TACATGGGAC AGCCTCTAAA CAATGATGAG GACCACGCCC ATTGGACAGA AGCAAAAATG 2640

CTCCTTGACA ACATAAACAC ACCAGAAGGG ATTATCCCAG CCCTCTTTGA GCCGGAGAGA 2700

GAAAAGAGTG CAGCAATAGA CGGGGAATAC AGACTACGGG GTGAAGCGAG GAAAACGTTC 2760

GTGGAGCTCA TGAGAAGAGG AGATCT 2786

( 2 ) INFORMATION FOR SEQ ID NO:54:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AAAAACAACA AAAAGATGAT TTTTATCGGC CGA 33

( 2 ) INFORMATION FOR SEQ ID NO:55:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

AGCTTCGGCC GATAAAAATC ATCTTTTGT TGTTTTT 37

( 2 ) INFORMATION FOR SEQ ID NO:56:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

AGCTTCTTTA TTCTATACTT AAAAAGTGAA AATAAATACA AAGGTTCTTG AGGGTTGTGT 60

TAAATTGAAA GCGAGAAATA ATCATAAATT ATTTCATTAT CGCGATATCC GTAAGTTTG 120

TATCGTAC 128

( 2 ) INFORMATION FOR SEQ ID NO:57:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

TCGAGTACGA TACAAACTTA ACGGATATCG CGATAATGAA ATAATTTATG ATTATTTCTC 60

GCTTTCAATT TAACACAACC CTCAAGAACC TTTGTATTTA TTTTCACTTT TTAAGTATAG 120

AATAAAGA 128

( 2 ) INFORMATION FOR SEQ ID NO:58:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

GTGAAAAAGC TTTGAAACTA AGCTGGTTC                                                              29

( 2 ) INFORMATION FOR SEQ ID NO:59:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

TCGGGATCCC GGCCGATAAA AATCACGCCT GAACCATGAC TCCTAGGTAC                                        50

( 2 ) INFORMATION FOR SEQ ID NO:60:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

ACTCTCAAAA GCTTCCCGGG AATTCTAGCT AGCTAGTTTT TATAAA                                            46

( 2 ) INFORMATION FOR SEQ ID NO:61:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

GATCTTTATA AAAACTAGCT AGCTAGAATT CCCGGGAAGC TTTGAGAGT                                         50

( 2 ) INFORMATION FOR SEQ ID NO:62:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

CTGAAATTAT TCATTATCG CGATATCCGT TAAGTTTGTA TCGTAATGGT TCCTCAGGCT                              60

CTCCTGTTTG T                                                                                 71

( 2 ) INFORMATION FOR SEQ ID NO:63:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CATTACGATA CAAACTTAAC GGATATCGCG ATAATGAAAT AATTTCAG                                          48

( 2 ) INFORMATION FOR SEQ ID NO:64:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

ACCCCTTCTG GTTTTTCCGT TGTGTTTTGG GAAATTCCCT ATTTACACGA TCCCAGACAA    60

GCTTAGATCT CAG    73

( 2 ) INFORMATION FOR SEQ ID NO:65:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CTGAGATCTA AGCTTGTCTG GGATCGTGTA AATAGGGAAT TTCCCAAAAC A    51

( 2 ) INFORMATION FOR SEQ ID NO:66:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

CAACGGAAAA ACCAGAAGGG GTACAAACAG GAGAGCCTGA GGAAC    45

( 2 ) INFORMATION FOR SEQ ID NO:67:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

ATCATCGAAT TCTGAATGTT AAATGTTATA CTTTG    35

( 2 ) INFORMATION FOR SEQ ID NO:68:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

GGGGGTACCT TTGAGAGTAC CACTTCAG    28

( 2 ) INFORMATION FOR SEQ ID NO:69:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

GGGTCTAGAG CGGCCGCTTA TAAAGATCTA AAATGCATAA TTTC    44

( 2 ) INFORMATION FOR SEQ ID NO:70:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

ATCATCCTGC AGGTATTCTA AACTAGGAAT AGATG                                        35

( 2 ) INFORMATION FOR SEQ ID NO:71:

( i ) SEQUENCE CHARACTERISTICS:
      ( A ) LENGTH: 82 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:71:

GTACGTGACT AATTAGCTAT AAAAAGGATC CGGTACCCTC GAGTCTAGAA TCGATCCCGG             60

GTTTTTATGA CTAGTTAATC AC                                                     82

( 2 ) INFORMATION FOR SEQ ID NO:72:

( i ) SEQUENCE CHARACTERISTICS:
      ( A ) LENGTH: 82 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:72:

GGCCGTGATT AACTAGTCAT AAAAACCCGG GATCGATTCT AGACTCGAGG GTACCGGATC             60

CTTTTTATAG CTAATTAGTC AC                                                     82

( 2 ) INFORMATION FOR SEQ ID NO:73:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:73:

TCGGGATCCG GGTTAATTAA TTAGTCATCA GGCAGGGCG                                    39

( 2 ) INFORMATION FOR SEQ ID NO:74:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:74:

TAGCTCGAGG GTACCTACGA TACAAACTTA ACGGATATCG                                   40

( 2 ) INFORMATION FOR SEQ ID NO:75:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:75:

CTTGATTTTT ATTGAT                                                             16

( 2 ) INFORMATION FOR SEQ ID NO:76:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:76:

CTAGATCAAT AAAAATCAAG CATG    24

( 2 ) INFORMATION FOR SEQ ID NO:77:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

CAGTTGGTAC CACTGGTATT TTATTTCAG    29

( 2 ) INFORMATION FOR SEQ ID NO:78:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

TATCTGAATT CCTGCAGCCC GGGTTTTTAT AGCTAATTAG TCAAATGTGA GTTAATATTA    60

G    61

( 2 ) INFORMATION FOR SEQ ID NO:79:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

TCGCTGAATT CGATATCAAG CTTATCGATT TTATGACTA GTTAATCAAA TAAAAAGCAT    60

ACAAGC    66

( 2 ) INFORMATION FOR SEQ ID NO:80:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

TTATCGAGCT CTGTAACATC AGTATCTAAC    30

( 2 ) INFORMATION FOR SEQ ID NO:81:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

TCCGGTACCG CGGCCGCAGA TATTTGTTAG CTTCTGC    37

( 2 ) INFORMATION FOR SEQ ID NO:82:

( i ) SEQUENCE CHARACTERISTICS:
        ( A ) LENGTH: 33 base pairs
        ( B ) TYPE: nucleic acid
        ( C ) STRANDEDNESS: single ( D ) TOPOLOGY: linear ( x i ) SEQUENCE DESCRIPTION: SEQ ID NO:82:

| TCGCTCGAGT | AGGATACCTA | CCTACTACCT | ACG | | | 33 |

( 2 ) INFORMATION FOR SEQ ID NO:83:

( i ) SEQUENCE CHARACTERISTICS:
        ( A ) LENGTH: 7351 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

| AGATATTTGT | TAGCTTCTGC | CGGAGATACC | GTGAAAATCT | ATTTTCTGGA | AGGAAAGGGA | 60 |
| GGTCTTATCT | ATTCTGTCAG | CAGAGTAGGT | TCCTCTAATG | ACGAAGACAA | TAGTGAATAC | 120 |
| TTGCATGAAG | GTCACTGTGT | AGAGTTCAAA | ACTGATCATC | AGTGTTGAT | AACTCTAGCG | 180 |
| TGTACGAGTC | CTTCTAACAC | TGTGGTTTAT | TGGCTGGAAT | AAAAGGATAA | AGACACCTAT | 240 |
| ACTGATTCAT | TTTCATCTGT | CAACGTTTCT | CTAAGAGATT | CATAGGTATT | ATTATTACAT | 300 |
| CGATCTAGAA | GTCTAATAAC | TGCTAAGTAT | ATTATTGGAT | TTAACGCGCT | ATAAACGCAT | 360 |
| CCAAAACCTA | CAAATATAGG | AGAAGCTTCT | CTTATGAAAC | TTCTTAAAGC | TTTACTCTTA | 420 |
| CTATTACTAC | TCAAAAGAGA | TATTACATTA | ATTATGTGAT | GAGGCATCCA | ACATATAAAG | 480 |
| AAGACTAAAG | CTGTAGAAGC | TGTTATGAAG | AATATCTTAT | CAGATATATT | AGATGCATTG | 540 |
| TTAGTTCTGT | AGATCAGTAA | CGTATAGCAT | ACGAGTATAA | TTATCGTAGG | TAGTAGGTAT | 600 |
| CCTAAAATAA | ATCTGATACA | GATAATAACT | TTGTAAATCA | ATTCAGCAAT | TTCTCTATTA | 660 |
| TCATGATAAT | GATTAATACA | CAGCGTGTCG | TTATTTTTG | TTACGATAGT | ATTTCTAAAG | 720 |
| TAAAGAGCAG | GAATCCCTAG | TATAATAGAA | ATAATCCATA | TGAAAAATAT | AGTAATGTAC | 780 |
| ATATTTCTAA | TGTTAACATA | TTTATAGGTA | AATCCAGGAA | GGGTAATTTT | TACATATCTA | 840 |
| TATACGCTTA | TTACAGTTAT | TAAAAATATA | CTTGCAAACA | TGTTAGAAGT | AAAAAAGAAA | 900 |
| GAACTAATTT | TACAAAGTGC | TTTACCAAAA | TGCCAATGGA | AATTACTTAG | TATGTATATA | 960 |
| ATGTATAAAG | GTATGAATAT | CACAAACAGC | AAATCGGCTA | TTCCCAAGTT | GAGAAACGGT | 1020 |
| ATAATAGATA | TATTTCTAGA | TACCATTAAT | AACCTTATAA | GCTTGACGTT | TCCTATAATG | 1080 |
| CCTACTAAGA | AAACTAGAAG | ATACATACAT | ACTAACGCCA | TACGAGAGTA | ACTACTCATC | 1140 |
| GTATAACTAC | TGTTGCTAAC | AGTGACACTG | ATGTTATAAC | TCATCTTTGA | TGTGGTATAA | 1200 |
| ATGTATAATA | ACTATATTAC | ACTGGTATTT | TATTTCAGTT | ATATACTATA | TAGTATTAAA | 1260 |
| AATTATATTT | GTATAATTAT | ATTATTATAT | TCAGTGTAGA | AAGTAAAATA | CTATAAATAT | 1320 |
| GTATCTCTTA | TTTATAACTT | ATTAGTAAAG | TATGTACTAT | TCAGTTATAT | TGTTTTATAA | 1380 |
| AAGCTAAATG | CTACTAGATT | GATATAAATG | AATATGTAAT | AAATTAGTAA | TGTAGTATAC | 1440 |
| TAATATTAAC | TCACATTATG | AATACTACTA | ATCACGAAGA | ATGCAGTAAA | ACATATGATA | 1500 |
| CAAACATGTT | AACAGTTTTA | AAAGCCATTA | GTAATAAACA | GTACAATATA | ATTAAGTCTT | 1560 |
| TACTTAAAAA | AGATATTAAT | GTTAATAGAT | TATTAACTAG | TTATTCTAAC | GAAATATATA | 1620 |
| AACATTTAGA | CATTACATTA | TGTAATATAC | TTATAGAACG | TGCAGCAGAC | ATAAACATTA | 1680 |
| TAGATAAGAA | CAATCGTACA | CCGTTGTTTT | ATGCGGTAAA | GAATAATGAT | TATGATATGG | 1740 |
| TTAAACTCCT | ATTAAAAAAT | GGCGCGAATG | TAAATTTACA | AGATAGTATA | GGATATTCAT | 1800 |
| GTCTTCACAT | CGCAGGTATA | CATAATAGTA | ACATAGAAAT | AGTAGATGCA | TTGATATCAT | 1860 |
| ACAAACCAGA | TTTAAACTCC | CGCGATTGGG | TAGGTAGAAC | ACCGCTACAT | ATCTTCGTGA | 1920 |

```
TAGAATCTAA CTTTGAAGCT GTGAAATTAT TATTAAAGTC AGGTGCATAT GTAGGTTTGA    1980
AAGACAAATG TAAGCATTTT CCTATACACC ATTCTGTAAT GAAATTAGAT CACTTAATAT    2040
CAGGATTGTT ATTAAAATAT GGAGCAAATC CAAATACAAT TAACGGCAAT GGAAAAACAT    2100
TATTAAGCAT TGCTGTAACA TCTAATAATA CACTACTGGT AGAACAGCTG CTGTTATATG    2160
GAGCAGAAGT TAATAATGGT GGTTATGATG TTCCAGCTCC TATTATATCC GCTGTCAGTG    2220
TTAACAATTA TGATATTGTT AAGATACTGA TACATAATGG TGCGAATATA AATGTATCCA    2280
CGGAAGATGG TAGAACGTCT TTACATACAG CTATGTTTTG GAATAACGCT AAAATAATAG    2340
ATGAGTTGCT TAACTATGGA AGTGACATAA ACAGCGTAGA TACTTATGGT AGAACTCCGT    2400
TATCTTGTTA TCGTAGCTTA AGTTATGATA TCGCTACTAA ACTAATATCA CGTATCATTA    2460
TAACAGATGT CTATCGTGAA GCACCAGTAA ATATCAGCGG ATTTATAATT AATTTAAAAA    2520
CTATAGAAAA TAATGATATA TTCAAATTAA TTAAAGATGA TTGTATTAAA GAGATAAACA    2580
TACTTAAAAG TATAACCCTT AATAAATTTC ATTCATCTGA CATATTTATA CGATATAATA    2640
CTGATATATG TTTATTAACG AGATTTATTC AACATCCAAA GATAATAGAA CTAGACAAAA    2700
AACTCTACGC TTATAAATCT ATAGTCAACG AGAGAAAAAT CAAAGCTACT TACAGGTATT    2760
ATCAAATAAA AAAGTATTA ACTGTACTAC CTTTTCAGG ATATTTCTCT ATATTGCCGT    2820
TTGATGTGTT AGTATATATA CTTGAATTCA TCTATGATAA TAATATGTTG GTACTTATGA    2880
GAGCGTTATC ATTAAAATGA AATAAAAGC ATACAAGCTA TTGCTTCGCT ATCGTTACAA    2940
AATGGCAGGA ATTTTGTGTA AACTAAGCCA CATACTTGCC AATGAAAAA ATAGTAGAAA    3000
GGATACTATT TTAATGGGAT TAGATGTTAA GGTTCCTTGG GATTATAGTA ACTGGGCATC    3060
TGTTAACTTT TACGACGTTA GGTTAGATAC TGATGTTACA GATTATAATA ATGTTACAAT    3120
AAAATACATG ACAGGATGTG ATATTTTTCC TCATATAACT CTTGGAATAG CAAATATGGA    3180
TCAATGTGAT AGATTTGAAA ATTTCAAAAA GCAAATAACT GATCAAGATT TACAGACTAT    3240
TTCTATAGTC TGTAAAGAAG AGATGTGTTT TCCTCAGAGT AACGCCTCTA ACAGTTGGG    3300
AGCGAAAGGA TGCGCTGTAG TTATGAAACT GGAGGTATCT GATGAACTTA GAGCCCTAAG    3360
AAATGTTCTG CTGAATGCGG TACCCTGTTC GAAGGACGTG TTTGGTGATA TCACAGTAGA    3420
TAATCCGTGG AATCCTCACA TAACAGTAGG ATATGTTAAG GAGGACGATG TCGAAAACAA    3480
GAAACGCCTA ATGGAGTGCA TGTCCAAGTT TAGGGGGCAA GAAATACAAG TTCTAGGATG    3540
GTATTAATAA GTATCTAAGT ATTTGGTATA ATTATTAAA TAGTATAATT ATAACAAATA    3600
ATAAATAACA TGATAACGGT TTTTATTAGA ATAAATAGA GATAATATCA TAATGATATA    3660
TAATACTTCA TTACCAGAAA TGAGTAATGG AAGACTTATA AATGAACTGC ATAAAGCTAT    3720
AAGGTATAGA GATATAAATT TAGTAAGGTA TATACTTAAA AAATGCAAAT ACAATAACGT    3780
AAATATACTA TCAACGTCTT TGTATTTAGC CGTAAGTATT TCTGATATAG AAATGGTAAA    3840
ATTATTACTA GAACACGGTG CCGATATTTT AAAATGTAAA AATCCTCCTC TTCATAAAGC    3900
TGCTAGTTTA GATAATACAG AAATTGCTAA ACTACTAATA GATTCTGGCG CTGACATAGA    3960
ACAGATACAT TCTGGAAATA GTCCGTTATA TATTTCTGTA TATAGAAACA ATAAGTCATT    4020
AACTAGATAT TTATTAAAAA AAGGTGTTAA TTGTAATAGA TTCTTTCTAA ATTATTACGA    4080
TGTACTGTAT GATAAGATAT CTGATGATAT GTATAAAATA TTTATAGATT TAATATTGA    4140
TCTTAATATA CAAACTAGAA ATTTTGAAAC TCCGTTACAT TACGCTATAA AGTATAAGAA    4200
TATAGATTTA ATTAGGATAT TGTTAGATAA TAGTATTAAA ATAGATAAAA GTTTATTTTT    4260
GCATAAACAG TATCTCATAA AGGCACTTAA AAATAATTGT AGTTACGATA TAATAGCGTT    4320
```

```
ACTTATAAAT CACGGAGTGC CTATAAACGA ACAAGATGAT TTAGGTAAAA CCCCATTACA    4380
TCATTCGGTA ATTAATAGAA GAAAGATGT AACAGCACTT CTGTTAAATC TAGGAGCTGA    4440
TATAAACGTA ATAGATGACT GTATGGGCAG TCCCTTACAT TACGCTGTTT CACGTAACGA   4500
TATCGAAACA ACAAGACAC TTTTAGAAAG AGGATCTAAT GTTAATGTGG TTAATAATCA    4560
TATAGATACC GTTCTAAATA TAGCTGTTGC ATCTAAAAAC AAAACTATAG TAAACTTATT   4620
ACTGAAGTAC GGTACTGATA CAAAGTTGGT AGGATTAGAT AAACATGTTA TTCACATAGC   4680
TATAGAAATG AAAGATATTA ATATACTGAA TGCGATCTTA TTATATGGTT GCTATGTAAA   4740
CGTCTATAAT CATAAAGGTT TCACTCCTCT ATACATGGCA GTTAGTTCTA TGAAAACAGA   4800
ATTTGTTAAA CTCTTACTTG ACCACGGTGC TTACGTAAAT GCTAAAGCTA AGTTATCTGG   4860
AAATACTCCT TTACATAAAG CTATGTTATC TAATAGTTTT AATAATATAA AATTACTTTT   4920
ATCTTATAAC GCCGACTATA ATTCTCTAAA TAATCACGGT AATACGCCTC TAACTTGTGT   4980
TAGCTTTTTA GATGACAAGA TAGCTATTAT GATAATATCT AAAATGATGT TAGAAATATC   5040
TAAAAATCCT GAAATAGCTA ATTCAGAAGG TTTTATAGTA AACATGGAAC ATATAAACAG   5100
TAATAAAAGA CTACTATCTA TAAAGAATC ATGCGAAAAA GAACTAGATG TTATAACACA    5160
TATAAAGTTA AATTCTATAT ATTCTTTTAA TATCTTTCTT GACAATAACA TAGATCTTAT   5220
GGTAAAGTTC GTAACTAATC CTAGAGTTAA TAAGATACCT GCATGTATAC GTATATATAG   5280
GGAATTAATA CGGAAAAATA AATCATTAGC TTTTCATAGA CATCAGCTAA TAGTTAAAGC   5340
TGTAAAAGAG AGTAAGAATC TAGGAATAAT AGGTAGGTTA CCTATAGATA TCAAACATAT   5400
AATAATGGAA CTATTAAGTA ATAATGATTT ACATTCTGTT ATCACCAGCT GTTGTAACCC   5460
AGTAGTATAA AGTGATTTTA TTCAATTACG AAGATAAACA TTAAATTTGT TAACAGATAT   5520
GAGTTATGAG TATTTAACTA AGTTACTTT AGGTACAAAT AAAATATTAT GTAATATAAT    5580
AGAAAATTAT CTTGAGTCTT CATTTCCATC ACCGTCTAAA TTTATTATTA AACCTTATT    5640
ATATAAGGCT GTTGAGTTTA GAAATGTAAA TGCTGTAAAA AAAATATTAC AGAATGATAT   5700
TGAATATGTT AAAGTAGATA GTCATGGTGT CTCGCCTTTA CATATTATAG CTATGCCTTC   5760
AAATTTTTCT CTCATAGACG CTGACATGTA TTCAGAATTT AATGAAATTA GTAATAGACT   5820
TCAAAAATCT AAAGATAGTA ACGAATTTCA ACGAGTTAGT CTACTAAGGA CAATTATAGA   5880
ATATGGTAAT GATAGTGATA TTAATAAGTG TCTAACATTA GTAAAAACGG ATATACAGAG   5940
TAACGAAGAG ATAGATATTA TAGATCTTTT GATAAATAAA GGAATAGATA TAAATATTAA   6000
AGACGATTTA GGAAACACAG CTTTGCATTA CTCGTGTGAT TATGCTAAGG GATCAAAGAT   6060
AGCTAAAAAG TTACTAGATT GTGGAGCAGA TCCTAACATA GTTAATGATT TAGGTGTTAC   6120
ACCACTAGCG TGTGCCGTTA ATACTTGCAA CGAGATACTA GTAGATATTC TGTTAAATAA   6180
TGATGCGAAT CCTGATTCAT CTTCCTCATA TTTTTTAGGT ACTAATGTGT TACATACAGC   6240
CGTAGGTACC GGTAATATAG ATATTGTAAG ATCTTTACTT ACGGCTGGTG CCAATCCTAA   6300
TGTAGGAGAT AAATCTGGAG TTACTCCTTT GCACGTTGCT GCAGCTGATA AGACAGTTA    6360
TCTGTTAATG GAGATGCTAC TAGATAGCGG GGCAGATCCA AATATAAAAT GCGCAAACGG   6420
TTTTACTCCT TTGTTTAATG CAGTATATGA TCATAACCGT ATAAAGTTAT TATTTCTTTA   6480
CGGGGCTGAT ATCAATATTA CTGACTCTTA CGGAAATACT CCTCTTACTT ATATGACTAA   6540
TTTTGATAAT AAATATGTAA ATTCAATAAT TATCTTACAA ATATATCTAC TTAAAAAAGA   6600
ATATAACGAT GAAAGATTGT TTCCACCTGG TATGATAAAA AATTTAAACT TTATAGAATC   6660
AAACGATAGT CTTAAAGTTA TAGCTAAAAA GTGTAATTCG TTAATACGCT ATAAGAAAAA   6720
```

| | | | | | |
|---|---|---|---|---|---|
| TAAAGACATA | GATGCAGATA | ACGTATTATT | GGAGCTTTTA | GAGGAAGAGG | AAGAAGATGA | 6780 |
| AATAGACAGA | TGGCATACTA | CATGTAAAAT | ATCTTAAATA | GTAATTAAAT | CATTGAAATA | 6840 |
| TTAACTTACA | AGATGATCGA | GGTCACTTAT | TATACTCTTT | AATAATGGGT | ACAAAGAGTA | 6900 |
| TTCATACGTT | AGTTAAATCT | AACGATGTAA | TACGTGTTCG | TGAATTAATA | AAGGATGATA | 6960 |
| GATGTTTGAT | AAATAAAAGA | AATAGAAGAA | ATCAGTCACC | TGTATATATA | GCTATATACA | 7020 |
| AAGGACTTTA | TGAAATGACT | GAAATGTTAT | TGCTAAATAA | TGCAAGTCTA | GATACTAAAA | 7080 |
| TACCTTCTTT | AATTATAGCA | GCTAAAAATA | ATGACTTACC | TATGATAAAA | TTATTGATAC | 7140 |
| AATACGGGGC | AAAATTAAAT | GATATTTATT | TAAGGGACAC | AGCATTAATG | ATAGCTCTCA | 7200 |
| GAAATGGTTA | CCTAGATATA | GCTGAATATT | TACTTTCATT | AGGAGCAGAA | TTTGTTAAAT | 7260 |
| ACAGACATAA | GGTAATATAT | AAATATCTAT | CAAAGATGC | GTATGAATTA | CTTTTAGAT | 7320 |
| TTAATTATGA | CGTTAATATA | ATAGATTGAG | A | | | 7351 |

( 2 ) INFORMATION FOR SEQ ID NO:84:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

TCGCTCGAGC TTTCTTGACA ATAACATAG        29

( 2 ) INFORMATION FOR SEQ ID NO:85:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

TAGGAGCTCT TTATACTACT GGGTTACAAC        30

( 2 ) INFORMATION FOR SEQ ID NO:86:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

AATTCCTCGA GGGATCC        17

( 2 ) INFORMATION FOR SEQ ID NO:87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

CGGGATCCCT CGAGG        15

( 2 ) INFORMATION FOR SEQ ID NO:88:

( i ) SEQUENCE CHARACTERISTICS:
        ( A ) LENGTH: 39 base pairs (B) TYPE: nucleic acid
(C) STRANDEDNESS: single
(D) TOPOLOGY: linear (xi) SEQUENCE DESCRIPTION: SEQ ID NO:88:

TCGGGATCCG GGTTAATTAA TTAGTTATTA GACAAGGTG                           39

(2) INFORMATION FOR SEQ ID NO:89:

(i) SEQUENCE CHARACTERISTICS:
 (A) LENGTH: 41 base pairs
 (B) TYPE: nucleic acid
 (C) STRANDEDNESS: single
 (D) TOPOLOGY: linear (xi) SEQUENCE DESCRIPTION: SEQ ID NO:89:

TAGGAATTCC TCGAGTACGA TACAAACTTA AGCGGATATC G                        41

(2) INFORMATION FOR SEQ ID NO:90:

(i) SEQUENCE CHARACTERISTICS:
 (A) LENGTH: 3209 base pairs
 (B) TYPE: nucleic acid
 (C) STRANDEDNESS: single
 (D) TOPOLOGY: linear (xi) SEQUENCE DESCRIPTION: SEQ ID NO:90:

```
TGAATGTTAA ATGTTATACT TTGGATGAAG CTATAAATAT GCATTGGAAA AATAATCCAT      60
TTAAAGAAAG GATTCAAATA CTACAAAACC TAAGCGATAA TATGTTAACT AAGCTTATTC     120
TTAACGACGC TTTAAATATA CACAAATAAA CATAATTTTT GTATAACCTA ACAAATAACT     180
AAAACATAAA AATAATAAAA GGAAATGTAA TATCGTAATT ATTTACTCA GGAATGGGGT      240
TAAATATTTA TATCACGTGT ATATCTATAC TGTTATCGTA TACTCTTTAC AATTACTATT     300
ACGAATATGC AAGAGATAAT AAGATTACGT ATTTAAGAGA ATCTTGTCAT GATAATTGGG     360
TACGACATAG TGATAAATGC TATTTCGCAT CGTTACATAA AGTCAGTTGG AAAGATGGAT     420
TTGACAGATG TAACTTAATA GGTGCAAAAA TGTTAAATAA CAGCATTCTA TCGGAAGATA     480
GGATACCAGT TATATTATAC AAAAATCACT GGTTGGATAA AACAGATTCT GCAATATTCG     540
TAAAAGATGA AGATTACTGC GAATTTGTAA ACTATGACAA TAAAAAGCCA TTTATCTCAA     600
CGACATCGTG TAATTCTTCC ATGTTTTATG TATGTGTTTC AGATATTATG AGATTACTAT     660
AAACTTTTTG TATACTTATA TTCCGTAAAC TATATTAATC ATGAAGAAAA TGAAAAAGTA     720
TAGAAGCTGT TCACGAGCGG TTGTTGAAAA CAACAAAATT ATACATTCAA GATGGCTTAC     780
ATATACGTCT GTGAGGCTAT CATGGATAAT GACAATGCAT CTCTAAATAG GTTTTTGGAC     840
AATGGATTCG ACCCTAACAC GGAATATGGT ACTCTACAAT CTCCTCTTGA AATGGCTGTA     900
ATGTTCAAGA ATACCGAGGC TATAAAAATC TTGATGAGGT ATGGAGCTAA ACCTGTAGTT     960
ACTGAATGCA CAACTTCTTG TCTGCATGAT GCGGTGTTGA GAGACGACTA CAAAATAGTG    1020
AAAGATCTGT TGAAGAATAA CTATGTAAAC AATGTTCTTT ACAGCGGAGG CTTTACTCCT    1080
TTGTGTTTGG CAGCTTACCT TAACAAAGTT AATTTGGTTA AACTTCTATT GGCTCATTCG    1140
GCGGATGTAG ATATTTCAAA CACGGATCGG TTAACTCCTC TACATATAGC CGTATCAAAT    1200
AAAAATTTAA CAATGGTTAA ACTTCTATTG AACAAAGGTG CTGATACTGA CTTGCTGGAT    1260
AACATGGGAC GTACTCCTTT AATGATCGCT GTACAATCTG GAAATATTGA AATATGTAGC    1320
ACACTACTTA AAAAAAATAA AATGTCCAGA ACTGGGAAAA ATTGATCTTG CCAGCTGTAA    1380
TTCATGGTAG AAAAGAAGTG CTCAGGCTAC TTTTCAACAA AGGAGCAGAT GTAAACTACA    1440
```

```
TCTTTGAAAG AAATGGAAAA TCATATACTG TTTTGGAATT GATTAAAGAA AGTTACTCTG   1500
AGACACAAAA GAGGTAGCTG AAGTGGTACT CTCAAAATGC AGAACGATGA CTGCGAAGCA   1560
AGAAGTAGAG AAATAACACT TTATGACTTT CTTAGTTGTA GAAAAGATAG AGATATAATG   1620
ATGGTCATAA ATAACTCTGA TATTGCAAGT AAATGCAATA ATAAGTTAGA TTTATTTAAA   1680
AGGATAGTTA AAAATAGAAA AAAAGAGTTA ATTTGTAGGG TTAAAATAAT ACATAAGATC   1740
TTAAAATTTA TAAATACGCA TAATAATAAA AATAGATTAT ACTTATTACC TTCAGAGATA   1800
AAATTTAAGA TATTTACTTA TTTAACTTAT AAAGATCTAA AATGCATAAT TTCTAAATAA   1860
TGAAAAAAAA GTACATCATG AGCAACGCGT TAGTATATTT TACAATGGAG ATTAACGCTC   1920
TATACCGTTC TATGTTTATT GATTCAGATG ATGTTTAGA AAAGAAAGTT ATTGAATATG    1980
AAAACTTTAA TGAAGATGAA GATGACGACG ATGATTATTG TTGTAAATCT GTTTAGATG    2040
AAGAAGATGA CGCGCTAAAG TATACTATGG TTACAAAGTA TAAGTCTATA CTACTAATGG   2100
CGACTTGTGC AAGAAGGTAT AGTATAGTGA AAATGTTGTT AGATTATGAT TATGAAAAAC   2160
CAAATAAATC AGATCCATAT CTAAAGGTAT CTCCTTTGCA CATAATTTCA TCTATTCCTA   2220
GTTTAGAATA CTTTTCATTA TATTTGTTTA CAGCTGAAGA CGAAAAAAAT ATATCGATAA   2280
TAGAAGATTA TGTTAACTCT GCTAATAAGA TGAAATTGAA TGAGTCTGTG ATAATAGCTA   2340
TAATCAGAGA AGTTCTAAAA GGAAATAAAA ATCAACTGA TCAGGATATA AAAACATTGG    2400
CTGATGAAAT CAACAAGGAG GAACTGAATA TAGCTAAACT ATTGTTAGAT AGAGGGGCCA   2460
AAGTAAATTA CAAGGATGTT TACGGTTCTT CAGCTCTCCA TAGAGCTGCT ATTGGTAGGA   2520
AACAGGATAT GATAAAGCTG TTAATCGATC ATGGAGCTGA TGTAAACTCT TTAACTATTG   2580
CTAAAGATAA TCTTATTAAA AAAAAATAAT ATCACGTTTA GTAATATTAA AATATATTAA   2640
TAACTCTATT ACTAATAACT CCAGTGGATA TGAACATAAT ACGAAGTTTA TACATTCTCA   2700
TCAAAATCTT ATTGACATCA AGTTAGATTG TGAAAATGAG ATTATGAAAT TAAGGAATAC   2760
AAAAATAGGA TGTAAGAACT TACTAGAATG TTTTATCAAT AATGATATGA ATACAGTATC   2820
TAGGGCTATA AACAATGAAA CGATTAAAAA TTATAAAAAT CATTTCCCTA TATATAATAC   2880
GCTCATAGAA AAATTCATTT CTGAAAGTAT ACTAAGACAC GAATTATTGG ATGGAGTTAT   2940
AAATTCTTTT CAAGGATTCA ATAATAAATT GCCTTACGAG ATTCAGTACA TTATACTGGA   3000
GAATCTTAAT AACCATGAAC TAAAAAAAAT TTTAGATAAT ATACATTAAA AAGGTAAATA   3060
GATCATCTGT TATTATAAGC AAAGATGCTT GTTGCCAATA ATATACAACA GGTATTTGTT   3120
TTTATTTTTA ACTACATATT TGATGTTCAT TCTCTTTATA TAGTATACAC AGAAAATTCA   3180
TAATCCACTT AGAATTTCTA GTTATCTAG                                    3209
```

( 2 ) INFORMATION FOR SEQ ID NO:91:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

```
GACTATCCTA CTTCCCTTGG GATGGGGGTT ATCTTTGTA                          39
```

( 2 ) INFORMATION FOR SEQ ID NO:92:

( i ) SEQUENCE CHARACTERISTICS:
        ( A ) LENGTH: 44 base pairs
        ( B ) TYPE: nucleic acid
        ( C ) STRANDEDNESS: single -continued (D) TOPOLOGY: linear (x i) SEQUENCE DESCRIPTION: SEQ ID NO:92:

TATCCGTTAA GTTTGTATCG TAATGGGTCT CAAGGTGAAC GTCT    44

(2) INFORMATION FOR SEQ ID NO:93:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (x i) SEQUENCE DESCRIPTION: SEQ ID NO:93:

GGATCCCCGG G    11

What is claimed is:

1. A recombinant poxvirus comprising DNA coding for at least one flavivirus structural protein, wherein the flavivirus is Yellow Fever virus or Dengue virus and the poxvirus is selected from the group consisting of: an avipox virus, a vaccinia virus wherein the open reading frames for the thymidine kinase gene, a hemorrhagic region, an A type inclusion body region, a hemagglutinin gene, a host range gene region and a large subunit, ribonucleotide reductase have been deleted therefrom, a vaccinia virus wherein regions C7L-K1L, J2R, B13R+B14R, A26L, A56R, and I4L have been deleted therefrom, and a NYVAC vaccinia virus.

2. The recombinant poxvirus of claim 1 wherein the DNA comprises a part of the flavivirus open reading frame from c to NS2b.

3. The recombinant poxvirus of claim 1 wherein the DNA encodes protein M or a precursor to protein M, and flavivirus proteins E, NS1 and NS2A.

4. The recombinant poxvirus of claim 1 wherein the poxvirus is a vaccinia virus.

5. The recombinant poxvirus of claim 1 wherein the poxvirus is an avipox virus.

6. The recombinant poxvirus of claim 5 wherein the avipox virus is canarypox virus.

7. The recombinant poxvirus of claim 1 wherein the flavivirus is Yellow Fever virus.

8. The recombinant poxvirus of claim 1 wherein the flavivirus is Dengue virus.

9. The recombinant poxvirus of claim 6 wherein the canarypox virus is an ALVAC canarypox virus.

10. The recombinant poxvirus of claim 6 wherein the canarypox virus is attenuated through more than 200 serial passages on chick embryo fibroblasts, a master seed therefrom was subjected to four successive plaque purifications under agar, from which a plaque clone was amplified through five additional passages.

11. The recombinant poxvirus of claim 4 wherein in the vaccinia virus, the open reading frames for the thymidine kinase gene, a hemorrhagic region, an A type inclusion body region, a hemagglutinin gene, a host range gene region and a large subunit, ribonucleotide reductase have been deleted therefrom, or regions C7L-K1L, J2R, B13R+B14R, A26L, A56R, and I4L have been deleted therefrom.

12. The recombinant poxvirus of claim 4 wherein the vaccinia virus is a NYVAC vaccinia virus.

13. The recombinant poxvirus of claim 1 which is vCP127 or vCP107.

14. The recombinant poxvirus of claim 1 wherein the DNA comprises DNA encoding C-terminal amino acids of C.

15. The recombinant poxvirus of claim 1 wherein the DNA further comprises DNA encoding NS2b.

16. An immunological composition comprising a carrier and a recombinant poxvirus according to any one of claims 1–15, wherein the composition is effective to induce an immunological response in a a host.

17. A method for producing a flavivirus structural protein comprising introducing into a cell a recombinant poxvirus, transforming cell with the expression vector, cultivating the transformed cell under conditions which allow expression of the recombinant poxvirus, and further purifying the protein as claim in any one of claims 1–15.

* * * * *